(12) United States Patent
de la Chapelle et al.

(10) Patent No.: US 9,057,068 B1
(45) Date of Patent: Jun. 16, 2015

(54) METHODS AND COMPOSITIONS USING MIR-3151 IN THE DIAGNOSIS AND TREATMENT OF CANCER

(71) Applicant: The Ohio State University, Columbus, OH (US)

(72) Inventors: Albert de la Chapelle, Delaware, OH (US); Ann-Kathrin Eisfeld, Columbus, OH (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 13/854,643

(22) Filed: Apr. 1, 2013

Related U.S. Application Data

(60) Provisional application No. 61/618,833, filed on Apr. 1, 2012, provisional application No. 61/790,784, filed on Mar. 15, 2013.

(51) Int. Cl.
  C12N 15/11 (2006.01)
  C12Q 1/68 (2006.01)
  C12N 15/113 (2010.01)

(52) U.S. Cl.
  CPC ........ *C12N 15/113* (2013.01); *C12N 2310/141* (2013.01)

(58) Field of Classification Search
  None
  See application file for complete search history.

(56) References Cited

U.S. PATENT DOCUMENTS

| 7,455,995 | B2 | 11/2008 | Tanner et al. | |
| 2007/0213292 | A1* | 9/2007 | Stoffel et al. | 514/44 |
| 2009/0131367 | A1* | 5/2009 | Gore et al. | 514/64 |
| 2010/0035760 | A1* | 2/2010 | Plasterk et al. | 506/9 |
| 2012/0225426 | A1 | 9/2012 | Tanner et al. | |

OTHER PUBLICATIONS

Eisfeld et al, MiR-3151, a Novel MicroRNA Embedded in BAALC, Is Only Weakly Co-Expressed with Its Host Gene and Independently Impacts on the Clinical Outcome of Older Patients (Pts) with De Novo Cytogenetically Normal Acute Myeloid Leukemia (CN-AML), Nov. 2011, Blood, ASH Annual Meeting Abstracts, 118: Abstract 1462.*

Minderman et al, Bortezomib activity and in vitro interactions with anthracyclines and cytarabine in acute myeloid leukemia cells are independent of multidrug resistance mechanisms and p53 status, 2007, Cancer Chemother Pharmacol, 60: 245-255.*

Buda et al, Differential expression of microRNAs in aggressive and non-aggressive papillary thyroid carcinomas, Sep. 9, 2012, Head Neck Oncol., vol. 4, No. 2, 52:1-12.*

Schrama et al, BRAFV600E mutations in malignant melanoma are associated with increased expressions of BAALC, 2008, Journal of Carcinogenesis, 7: 1-6.*

Calin et al., "Small Gene, Big Number, Many Effects", Blood, 2012, vol. 120, pp. 240-241.

Eisfeld et al., "Heritable Polymorphism Predisposes to High BAALC Expression in Acute Myeloid Leukemia", PNAS, 2012, vol. 109, pp. 6668-6673.

Fatica, "Noncoding RNAs in Acute Myeloid Leukemia: From Key Regulators to Clinical Players", Hindawi Publishing Corporation, Scientifica, 2012, Article ID 925758, pp. 1-10.

Tanner, et al. "BAALC, the Human Member of a Novel Mammalian Neuroectoderm Gene Lineage, is Implicated in Hematopoiesis and Acute Leukemia", PNAS, 2001, vol. 98, No. 24, pp. 13901-13906.

* cited by examiner

*Primary Examiner* — Tracy Vivlemore
*Assistant Examiner* — Kate Poliakova
(74) *Attorney, Agent, or Firm* — MacMillan, Sobanski & Todd, LLC

(57) ABSTRACT

Compositions comprising therapeutic oligonucleotide compounds that target the expression of genes associated with tumorigenesis or cell transformation are provided. Methods are described to manipulate and treat the oncogenic deregulation of the TP53-associated apoptosis pathway. Markers for acute myeloid leukemia (AML) and uses thereof are described.

6 Claims, 61 Drawing Sheets
(10 of 61 Drawing Sheet(s) Filed in Color)

Clinical and molecular characteristics according to *miR-3151* expression status in CN-AML patients aged 60 years or older

| Characteristic | Low miR-3151[a] (n=90) | High miR-3151[a] (n=89) | P[b] |
|---|---|---|---|
| Age, y | | | .99 |
| Median | 68 | 68 | |
| Range | 60-79 | 60-81 | |
| Sex, no. (%) | | | .88 |
| Male | 48 (53) | 49 (55) | |
| Female | 42 (47) | 40 (45) | |
| Race, no. (%) | | | .10 |
| White | 79 (88) | 85 (95) | |
| Non-White | 11 (12) | 4 (5) | |
| Hemoglobin, g/dL | | | .47 |
| Median | 9.3 | 9.5 | |
| Range | 6.0-11.7 | 6.5-15.0 | |
| Platelet count, x10⁹/L | | | .38 |
| Median | 60 | 69 | |
| Range | 4-481 | 11-850 | |
| WBC count, x10⁹/L | | | .10 |
| Median | 28.3 | 38.7 | |
| Range | 1.4-450.0 | 1.1-434.1 | |
| Percent of blood blasts | | | .02 |
| Median | 65 | 39 | |
| Range | 0-98 | 0-99 | |
| Percent of bone marrow blasts | | | .52 |
| Median | 70 | 69 | |
| Range | 11-97 | 4-96 | |
| Extramedullary involvement, no. (%) | 21 (24) | 24 (28) | .73 |
| NPM1, no. (%) | | | <.001 |
| Mutated | 71 (79) | 43 (49) | |
| Wild-type | 19 (21) | 45 (51) | |
| FLT3-ITD, no. (%) | | | 1.00 |
| Present | 33 (37) | 33 (38) | |
| Absent | 57 (63) | 55 (63) | |
| CEBPA, no. (%) | | | .83 |
| Mutated | 12 (13) | 13 (15) | |
| Single mutated | 7 | 8 | |
| Double mutated | 5 | 5 | |
| Wild-type | 78 (87) | 76 (85) | |
| ELN Genetic Group, no. (%)[†] | | | .05 |
| Favorable | 50 (56) | 36 (40) | |
| Intermediate-I | 40 (44) | 53 (60) | |
| RUNX1, no. (%) | | | <.001 |
| Mutated | 4 (5) | 19 (24) | |
| Wild-type | 80 (95) | 59 (76) | |
| FLT3-TKD, no. (%) | | | 1.00 |
| Present | 7 (8) | 7 (8) | |
| Absent | 82 (92) | 79 (92) | |
| WT1, no. (%) | | | .08 |
| Mutated | 3 (3) | 9 (10) | |
| Wild-type | 87 (97) | 79 (90) | |
| TET2, no. (%) | | | .33 |
| Mutated | 24 (27) | 30 (35) | |
| Wild-type | 65 (73) | 56 (65) | |
| MLL-PTD, no. (%) | | | .50 |
| Present | 5 (6) | 8 (8) | |
| Absent | 83 (94) | 87 (92) | |

Figure 6

| | | | |
|---|---|---|---|
| IDH1, no. (%) | | | 1.00 |
| R132 mutated | 12 (13) | 10 (11) | |
| V71I mutated | 0 | 1 (1) | |
| Wild-type | 77 (87) | 76 (87) | |
| IDH2, no. (%) | | | .71 |
| IDH2 | 20 (22) | 17 (20) | |
| R140 mutated | 20 | 14 | |
| R172 mutated | 0 | 3 | |
| Wild-type | 69 (78) | 70 (80) | |
| ASXL1, no. (%) | | | .13 |
| Mutated | 9 (10) | 16 (19) | |
| Wild-type | 79 (90) | 69 (81) | |
| DNMT3A, no. (%) | | | .74 (mut vs wt) |
| Mutated | 27 (31) | 29 (35) | |
| R882 | 15 | 19 | .56 (R882 vs wt) |
| Non-R882 | 12 | 10 | 1.00 (Non-R882 vs wt) |
| Wild-type | 59 (69) | 55 (65) | |
| ERG expression group, no. (%)‡ | | | .40 |
| High | 42 (58) | 35 (50) | |
| Low | 31 (42) | 35 (50) | |
| BAALC expression group, no. (%)‡ | | | <.001 |
| High | 34 (39) | 56 (66) | |
| Low | 54 (61) | 29 (34) | |
| MN1 expression group, no. (%)‡ | | | .05 |
| High | 18 (37) | 31 (56) | |
| Low | 31 (63) | 24 (44) | |

FLT3-ITD indicates internal tandem duplication of the FLT3 gene; ELN, European LeukemiaNet; FLT3-TKD, tyrosine kinase domain mutation in the FLT3 gene; MLL-PTD, partial tandem duplication of the MLL gene.
‡The median expression value was used as the cutpoint.
*P-values for categorical variables are from Fisher's exact test. P-values for continuous variables are from Wilcoxon rank sum test.
†The ELN Favorable Genetic Group comprises patients with mutated CEBPA and those with mutated NPM1 without FLT3-ITD; the ELN Intermediate-I Genetic Group includes patients with CEBPA wild-type who are either FLT3-ITD-positive and NPM1-mutated, FLT3-ITD-negative and NPM1 wild-type or FLT3-ITD-positive and NPM1 wild-type.

Figure 6 cont.

Multivariable analysis for outcome according to the *miR-3151* expression status in older patients with CN-AML

| Endpoint | Variables in Final Models | OR/HR | 95% CI | P |
|---|---|---|---|---|
| CR* | *miR-3151*, high vs low | 0.56 | 0.27 to 1.19 | .13 |
|  | *BAALC*, high vs low | 0.23 | 0.10 to 0.52 | <.001 |
|  | WBC, continuous, 50-unit increase | 0.65 | 0.48 to 0.88 | .01 |
| DFS† | *miR-3151*, high vs low | 2.38 | 1.47 to 3.85 | <.001 |
|  | *FLT3*-TKD, positive vs no TKD | 0.28 | 0.11 to 0.73 | .009 |
|  | *ERG*, high vs low | 2.41 | 1.50 to 3.86 | <.001 |
| OS‡ | *miR-3151*, high vs low | 1.69 | 1.14 to 2.50 | .009 |
|  | *ERG*, high vs low | 1.71 | 1.16 to 2.53 | .007 |
|  | *DNMT3A* R882 v wild-type<br>Non-R882 vs wild-type | 1.66<br>1.11 | 1.04 to 2.66<br>0.61 to 2.01 | .04<br>.74 |
|  | *BAALC*, high vs low | 1.93 | 1.32 to 2.82 | <.001 |

Odds ratios greater than (less than) 1.0 mean higher (lower) CR rate for the higher values of the continuous variables and the first category listed for the categorical variables. Hazard ratios greater than (less than) 1.0 indicate higher (lower) risk for an event for the first category listed for the categorical variables.

CI indicates confidence interval; CR, complete remission; DFS, disease-free survival; OS, overall survival; OR, odds ratio; HR, hazard ratio; WBC, white blood count.

* Variables considered in the model based on univariable analyses were: *miR-3151* expression (high vs low; median cut), *BAALC* expression (high vs low; median cut), *ERG* expression (high vs low, median cut), *FLT3*-ITD (positive vs no ITD), *NPM1* (mutated vs wild-type), *WT1* (mutated vs wild-type), *MLL*-PTD (present vs absent), *ASXL1* (mutated vs wild-type), *RUNX1* (mutated vs wild-type), WBC (continuous, 50-unit increase), platelets (continuous, 50-unit increase) and age (continuous, 10-year increase).

† Variables considered in the model based on univariable analyses were: *miR-3151* expression (high vs low; median cut), *BAALC* expression (high vs low; median cut), *ERG* expression (high vs low; median cut), *FLT3*-ITD (positive vs no ITD), *FLT3*-TKD (positive vs no TKD), *NPM1* (mutated vs wild-type), *DNMT3A* (R882 vs Non-R882 vs wild-type), *RUNX1* (mutated vs wild-type), *WT1* (mutated vs wild-type) and WBC (continuous, log base 2).

‡ Variables considered in the model based on univariable analyses were: *miR-3151* expression (high vs low; median cut), *BAALC* expression (high vs low; median cut), *ERG* expression (high vs low; median cut), *FLT3*-ITD (positive vs no ITD), *NPM1* (mutated vs wild-type), *ASXL1* (mutated vs wild-type), *RUNX1* (mutated vs wild-type), *WT1* (mutated vs wild-type), *DNMT3A* (R882 vs Non-R882 vs wild-type), platelets (continuous, 50-unit increase) and WBC (continuous, 50-unit increase).

Figure 7

Bivariable models for outcome according to the expression status of *miR-3151* and *BAALC* in older patients with cytogenetically normal acute myeloid leukemia

A Complete Remission

| Variable | Categories | P-value | Odds Ratio* (95% CI) |
|---|---|---|---|
| miR-3151 expression | High vs Low (median cut) | <.001 | 0.47 (0.23, 0.96) |
| BAALC expression | High vs Low (median cut) | <.001 | 0.35 (0.14, 0.84) |

B Disease-Free Survival

| Variable | Categories | P-value | Hazard Ratio† (95% CI) |
|---|---|---|---|
| miR-3151 expression | High vs Low (median cut) | .01 | 1.68 (1.13, 2.48) |
| BAALC expression | High vs Low (median cut) | .003 | 1.92 (1.34, 2.89) |

C Overall Survival

| Variable | Categories | P-value | Hazard Ratio† (95% CI) |
|---|---|---|---|
| miR-3151 expression | High vs Low (median cut) | .002 | 1.69 (1.22, 2.36) |
| BAALC expression | High vs Low (median cut) | <.001 | 2.01 (1.45, 2.81) |

*An odds ratio>1 (<1) corresponds to a higher (lower) odds of achieving a CR for the first level listed of a dichotomous variable.

†A hazard ratio>1 (<1) corresponds to a higher (lower) risk for the first level listed of a dichotomous variable.

Figure 8

Outcome analysis according to miR-3151 expression status and ELN genetic group in older patients with cytogenetically normal acute myeloid leukemia

| Outcome | Favorable | | | Intermediate-I | | |
|---|---|---|---|---|---|---|
| | Low miR-3151 n=50 | High miR-3151 n=35 | P | Low miR-3151 n=40 | High miR-3151 n=52 | P |
| Complete remission rate, no. (%) | 42 (84) | 26 (74) | .29 | 31 (78) | 27 (52) | .02 |
| Disease-free Survival | | | .55 | | | <.001 |
| Median, y | 1.1 | 1.0 | | 1.1 | 0.6 | |
| Disease-free at 3 y, % (95% CI) | 29 (16-43) | 15 (5-31) | | 23 (10-38) | 0 | |
| Overall Survival | | | .18 | | | <.001 |
| Median, y | 1.5 | 1.4 | | 1.0 | 0.7 | |
| Alive at 3 y, % (95% CI) | 36 (23-49) | 20 (9-34) | | 28 (15-42) | 4 (1-12) | |

Abbreviations: y, years; CI, confidence interval.
* The ELN Favorable Genetic Group comprises patients with mutated CEBPA and those with mutated NPM1 without FLT3-ITD; the ELN Intermediate-I Genetic Group includes patients with CEBPA wild-type who are either FLT3-ITD-positive and NPM1-mutated, FLT3-ITD-negative and NPM1 wild-type or FLT3-ITD-positive and NPM1 wild-type.

Figure 9

Primer sequences and corresponding annealing temperatures for cloning and mutational sequence changes of the FBXL20 and USP40 3'-UTRs.

| Amplicon | Primer Sequence (5'-3') | Annealing Temperature |
|---|---|---|
| FBXL20 cloning F | cgtcgaattcGTTGCCTTGAAATCACTGTG | 58 °C |
| FBXL20 cloning R | cgtcgaattcATGCAAACTGTAAACACGAC | |
| FBXL20 mutation F | CTGTTGCTCCCCTTTACACTCTTG | 52 °C |
| FBXL20 mutation R | CAAGAGTGTAAAGGGGAGCAACAG | 52 °C |
| USP40 cloning F | cgtcgaattcGGCTTCTCACAGTGTCTCAG | 58 °C |
| USP40 cloning R | cgtcgaattcCTCGTGGAAAGAGCTCGCAC | |
| USP40 mutation F | GACTTCATGGCCTTTACTCGTTC | 52 °C |
| USP40 mutation R | GAACGAGTAAAGGCCATGAAGTC | 52 °C |

Figure 10

*miR-3151*-associated gene expression signature in CN-AML patients: Upregulated genes. High *miR-3151* expresser status was associated with the upregulation of 192 probe sets (116 annotated genes) out of 24,649 investigated (Global test *P*-value = .001).

| Probe set | Gene Symbol | Fold-change: miR-3151 High/Low | P-value |
|---|---|---|---|
| 202912_at | ADM | 2.81 | 1.00E-07 |
| 1566383_at | DNTT | 2.80 | 0.000311 |
| 219895_s_at | BAALC | 2.55 | 1.20E-06 |
| 210487_at | DNTT | 2.49 | 0.0003486 |
| 222780_s_at | BAALC | 2.44 | 1.00E-06 |
| 1562433_at | FLJ10489 | 2.08 | 4.19E-06 |
| 201540_at | FHL1 | 2.02 | 3.70E-06 |
| 205330_at | MN1 | 2.00 | 0.0001118 |
| 229390_at | FAM69B | 1.99 | 3.88E-05 |
| 230898_at | BEND4 | 1.91 | 0.0002137 |
| 204057_at | IRF8 | 1.91 | 0.0003164 |
| 243819_at |  | 1.88 | 7.27E-05 |
| 215078_at | SOD2 | 1.88 | 0.0001314 |
| 235994_at | CRHBP | 1.87 | 4.71E-05 |
| 209823_x_at | HLA-DQB1 | 1.87 | 0.000231 |
| 202283_at | SERPINF1 | 1.84 | 9.10E-05 |
| 210298_s_at | FHL1 | 1.81 | 1.23E-05 |
| 238378_at | GGTA1 | 1.80 | 8.50E-06 |
| 219648_at | MREG | 1.80 | 9.13E-05 |
| 229391_s_at | FAM69B | 1.77 | 3.80E-05 |
| 223467_at | RASD1 | 1.77 | 2.42E-05 |
| 213931_at |  | 1.76 | 4.39E-05 |
| 242814_at | SERPINB9 | 1.76 | 1.13E-05 |
| 224435_at | C10orf58 | 1.74 | 0.0001958 |
| 214505_s_at | FHL1 | 1.74 | 1.42E-05 |
| 209723_at | SERPINB9 | 1.74 | 0.0006185 |
| 1559425_at |  | 1.73 | 9.90E-06 |
| 233323_at |  | 1.73 | 1.01E-05 |
| 211858_x_at |  | 1.73 | 0.0005121 |
| 215990_s_at | BCL6 | 1.73 | 0.0006403 |
| 1554795_a_at | EMP1 | 1.73 | 0.0003695 |
| 243064_at | SDK2 | 1.73 | 1.21E-05 |
| 202388_at | RGS2 | 1.68 | 0.0001908 |

Figure 11

| | | | |
|---|---|---|---|
| 1552542_s_at | TAGAP | 1.67 | 4.19E-05 |
| 213506_at | F2RL1 | 1.66 | 0.0009492 |
| 210298_x_at | FHL1 | 1.65 | 0.0001137 |
| 211302_s_at | PDE4B | 1.65 | 0.0007491 |
| 239879_at | | 1.63 | 0.0001418 |
| 204794_at | DUSP3 | 1.63 | 8.77E-05 |
| 201539_s_at | FHL1 | 1.62 | 5.28E-05 |
| 209305_s_at | GADD45B | 1.62 | 0.0002034 |
| 200832_s_at | SCD | 1.61 | 7.79E-06 |
| 234823_at | MYLK | 1.60 | 0.0007962 |
| 215223_s_at | SOD2 | 1.60 | 0.0005505 |
| 228758_at | BCL6 | 1.59 | 0.0006752 |
| 207574_s_at | GADD45B | 1.59 | 0.000571 |
| 209304_x_at | GADD45B | 1.58 | 0.0003232 |
| 208937_s_at | ID1 | 1.58 | 0.0004095 |
| 223315_at | | 1.58 | 0.0001866 |
| 226878_at | HLA-DOA | 1.57 | 0.0008173 |
| 219016_at | NLRP3 | 1.57 | 0.0004723 |
| 1558208_at | CLEC2B | 1.54 | 0.0009631 |
| 203491_at | DHRS3 | 1.54 | 0.0005449 |
| 209457_at | DUSP5 | 1.54 | 0.0002858 |
| 209582_s_at | CD200 | 1.53 | 0.000115 |
| 229543_at | FAM26F | 1.53 | 0.0004945 |
| 202177_at | GAS6 | 1.53 | 3.66E-05 |
| 201566_x_at | ID2 | 1.53 | 0.000287 |
| 206682_at | CLEC10A | 1.52 | 0.0006437 |
| 203523_at | LSP1 | 1.52 | 0.0005851 |
| 227198_at | STARD9 | 1.52 | 0.000233 |
| 201565_s_at | ID2 | 1.51 | 0.0007525 |
| 236898_at | | 1.51 | 0.0008963 |
| 230212_at | SPRY1 | 1.51 | 0.0002888 |
| 201531_at | ZFP36 | 1.51 | 0.0009634 |
| 243485_at | | 1.50 | 0.0002234 |
| 202340_x_at | NR4A1 | 1.50 | 2.76E-05 |
| 219480_at | SNAI1 | 1.49 | 1.00E-07 |
| 204918_s_at | MLLT3 | 1.48 | 0.0003138 |
| 234650_at | TAGAP | 1.48 | 0.000567 |
| 235574_at | GBP4 | 1.47 | 0.0001037 |
| 208436_s_at | IRF7 | 1.46 | 0.0002375 |
| 209615_s_at | PAK1 | 1.46 | 0.000625 |
| 229864_at | C14orf181 | 1.46 | 4.38E-05 |

Figure 11 cont.

| | | | |
|---|---|---|---|
| 214537_at | HIST1H1D | 1.45 | 0.0004494 |
| 223217_s_at | NFKBIZ | 1.44 | 0.0009275 |
| 237478_at | SETBP1 | 1.43 | 0.0008673 |
| 214390_s_at | BCAT1 | 1.42 | 0.0004888 |
| 228818_at | PEAR1 | 1.42 | 0.0003346 |
| 235175_at | GBP4 | 1.41 | 5.53E-05 |
| 1566232_at | | 1.41 | 0.0001209 |
| 201841_s_at | HSPB1 | 1.40 | 0.0004139 |
| 202555_s_at | MYLK | 1.40 | 0.0007748 |
| 241387_at | | 1.40 | 0.0001784 |
| 215671_at | PDE4B | 1.40 | 0.0001311 |
| 212667_at | SPARC | 1.40 | 0.0003804 |
| 222773_s_at | GALNT12 | 1.39 | 0.0006944 |
| 233867_at | | 1.39 | 0.0001436 |
| 239901_at | | 1.39 | 0.0004709 |
| 1558411_at | C3orf50 | 1.38 | 0.0002312 |
| 231900_at | COL8A2 | 1.38 | 0.0006902 |
| 209722_s_at | SERPINB9 | 1.38 | 0.000104 |
| 235782_x_at | LOC284801 | 1.37 | 0.000939 |
| 223129_x_at | MYLIP | 1.37 | 9.50E-06 |
| 225775_at | TSPAN33 | 1.37 | 0.0007704 |
| 232239_at | hCG_2024094 | 1.36 | 0.0003539 |
| 228319_s_at | MYLIP | 1.36 | 4.56E-05 |
| 240671_at | | 1.36 | 0.0006524 |
| 202014_at | PPP1R15A | 1.36 | 0.0003242 |
| 233138_at | C18orf1 | 1.35 | 7.46E-05 |
| 235205_at | LOC346887 | 1.35 | 0.0007481 |
| 244087_at | | 1.35 | 0.0001114 |
| 221261_x_at | | 1.35 | 0.0001938 |
| 244878_at | | 1.35 | 0.0003286 |
| 223218_s_at | NFKBIZ | 1.35 | 0.0006108 |
| 227053_at | PACSIN1 | 1.35 | 3.24E-05 |
| 237006_at | PPP1R14A | 1.35 | 1.07E-05 |
| 207821_s_at | PTK2 | 1.35 | 0.0002505 |
| 238949_at | RNF145 | 1.35 | 0.0001135 |
| 1552541_at | TAGAP | 1.35 | 3.61E-05 |
| 1598_g_at | GAS6 | 1.34 | 7.70E-06 |
| 237571_at | | 1.34 | 0.0008857 |
| 37028_at | PPP1R15A | 1.34 | 0.0003758 |
| 1555579_s_at | PTPRM | 1.34 | 0.000581 |
| 242738_s_at | ZFHX3 | 1.34 | 0.0003128 |

Figure 11 cont.

| | | | |
|---|---|---|---|
| 223139_s_at | MYLIP | 1.33 | 9.49E-05 |
| 1565034_s_at | | 1.33 | 0.0001131 |
| 241577_at | | 1.33 | 0.0002603 |
| 234121_at | GAB0459 | 1.32 | 0.000358 |
| 206313_at | HLA-DOA | 1.31 | 0.0004987 |
| 231887_s_at | KIAA1274 | 1.31 | 0.0007634 |
| 210313_at | LILRA4 | 1.31 | 1.42E-05 |
| 243868_at | | 1.31 | 0.008714 |
| 218611_at | IER5 | 1.30 | 0.0008784 |
| 206439_at | F2RL1 | 1.29 | 0.0003935 |
| 1567224_at | HMGA2 | 1.29 | 0.0003882 |
| 232883_at | MREG | 1.29 | 0.0003514 |
| 229484_at | PPM1J | 1.29 | 1.18E-05 |
| 233379_at | PRR5L | 1.29 | 0.0008498 |
| 204713_s_at | F5 | 1.28 | 0.0008393 |
| 204454_at | LDOC1 | 1.28 | 0.0007596 |
| 226998_s_at | MYLIP | 1.28 | 0.0002199 |
| 1563357_at | | 1.28 | 0.0002197 |
| 243561_at | | 1.28 | 0.0007152 |
| 223839_s_at | SCD | 1.28 | 0.000563 |
| 202308_at | SREBF1 | 1.28 | 0.00045 |
| 212654_at | TPM2 | 1.28 | 1.80E-06 |
| 239272_at | MMP28 | 1.27 | 0.0009808 |
| 223313_s_at | | 1.27 | 0.0001821 |
| 223304_at | SLC37A3 | 1.27 | 0.0001288 |
| 237315_at | | 1.26 | 7.76E-05 |
| 238323_at | | 1.26 | 0.000848 |
| 230083_at | ARL9 | 1.25 | 0.0003144 |
| 223385_at | CYP2S1 | 1.25 | 4.60E-06 |
| 228283_at | GRASP | 1.25 | 0.0004894 |
| 1570362_at | LOC100288809 | 1.25 | 4.73E-05 |
| 223932_at | | 1.25 | 0.0002419 |
| 1557223_at | | 1.25 | 0.0005936 |
| 211143_x_at | NR4A1 | 1.25 | 9.76E-06 |
| 208779_x_at | DDR1 | 1.24 | 2.70E-06 |
| 210749_x_at | DDR1 | 1.24 | 3.86E-05 |
| 206896_s_at | GNG7 | 1.24 | 0.0009744 |
| 241877_at | | 1.24 | 1.87E-05 |
| 212838_at | | 1.24 | 5.65E-05 |
| 203338_at | PTPRM | 1.24 | 0.0001988 |
| 211708_s_at | SCD | 1.24 | 4.78E-05 |

Figure 11 cont.

| | | | |
|---|---|---|---|
| 1552391_a_at | CORO6 | 1.23 | 0.0005448 |
| 1559539_at | PTK2 | 1.23 | 0.000399 |
| 204811_s_at | CACNA2D2 | 1.22 | 0.0005027 |
| 239317_at | CEACAM21 | 1.23 | 0.0003981 |
| 239373_s_at | MMP28 | 1.23 | 0.0001338 |
| 224771_at | NAV1 | 1.23 | 0.0003001 |
| 224773_at | NAV1 | 1.23 | 0.000377 |
| 227486_at | NT5E | 1.22 | 0.0003518 |
| 40148_at | APBB2 | 1.21 | 0.0005348 |
| 214781_at | | 1.21 | 0.0002272 |
| 216478_x_at | | 1.21 | 0.0005018 |
| 236458_at | PRKCE | 1.21 | 0.0003985 |
| 1553483_a_at | TDH | 1.21 | 0.0004184 |
| 205494_at | ZNF821 | 1.21 | 0.0003261 |
| 212817_at | DNAJB5 | 1.20 | 0.0001555 |
| 228463_at | ENHO | 1.20 | 0.0003024 |
| 244439_at | | 1.20 | 0.0009389 |
| 227594_at | NAV1 | 1.20 | 0.0009954 |
| 208711_s_at | CCND1 | 1.19 | 0.0005108 |
| 207285_at | CEACAM4 | 1.19 | 0.0003577 |
| 52651_at | COL8A2 | 1.19 | 7.57E-05 |
| 205225_at | ESR1 | 1.19 | 0.0007582 |
| 212797_s_at | | 1.19 | 0.0002102 |
| 233398_at | | 1.19 | 0.0004165 |
| 209335_s_at | RGS16 | 1.19 | 0.0008462 |
| 209323_at | ADCY3 | 1.18 | 0.00048 |
| 202986_at | ARNT2 | 1.18 | 0.0004949 |
| 226865_at | FGD6 | 1.18 | 0.0007413 |
| 203726_s_at | LAMA3 | 1.18 | 5.14E-05 |
| 220008_at | CCDC48 | 1.17 | 0.0008158 |
| 236986_at | FLJ43663 | 1.17 | 0.0001125 |
| 236499_at | NRARP | 1.17 | 0.000448 |
| 203758_at | ARHGEF17 | 1.16 | 0.000781 |
| 220448_at | KCNK12 | 1.16 | 0.000976 |
| 1568795_at | | 1.16 | 0.0008143 |
| 225999_at | hcag7.1196 | 1.16 | 0.0008626 |

Figure 11 cont.

*miR-3151*-associated gene expression signature in CN-AML patients: Downregulated genes. High *miR-3151* expresser status was associated with the downregulation of 405 probe sets (258 annotated genes) out of 24,649 investigated (Global test P-value = .001). Seventy-three of the downregulated genes are *in-silico* predicted targets of *miR-3151* (microrna.org). Highlighted in grey are the six probe-sets corresponding to annotated genes of the *in-silico* targets which showed ≥25% downregulation with a P-value < .0001.

| Probe set | Gene Symbol | Fold-change: miR-3151 High/Low | P-value | miR-3151 in-silico predicted Target |
|---|---|---|---|---|
| 236882_s_at | hCG_2042068 | 0.44 | 0.0006833 | n.a.* |
| 1558871_at |  | 0.48 | 4.19E-05 |  |
| 219737_s_at | PCDH9 | 0.48 | 0.0003818 | no |
| 238784_at | DPY19L2 | 0.49 | 0.0003588 | yes |
| 204082_at | PBX3 | 0.53 | 5.30E-06 | no |
| 236781_at | hCG_2042068 | 0.54 | 0.0003422 | n.a. |
| 242172_at | MEIS1 | 0.55 | 0.000455 | yes |
| 215767_at | ZNF644 | 0.55 | 1.79E-05 | no |
| 242321_at |  | 0.55 | 0.0006437 |  |
| 205801_s_at | RASGRP3 | 0.56 | 0.0007374 | no |
| 240747_at |  | 0.57 | 9.46E-05 |  |
| 235195_at | HIST1H2BC | 0.58 | 0.00091 | no |
| 236743_at | hCG_2042068 | 0.59 | 0.0001059 | n.a. |
| 220416_at | ATP8B4 | 0.59 | 0.0002588 | no |
| 1559266_s_at | C10orf140 | 0.59 | 0.0004956 | no |
| 240773_at |  | 0.60 | 5.11E-05 |  |
| 205942_s_at | ACSM3 | 0.61 | 0.0007281 | no |
| 210377_at | ACSM3 | 0.63 | 0.0005425 | no |
| 234145_at | PBX3 | 0.64 | 2.22E-05 | no |
| 213006_at | WDFY3 | 0.64 | 0.0003492 | yes |
| 241497_at |  | 0.66 | 0.0002142 |  |
| 236915_at |  | 0.66 | 0.0008877 |  |
| 226736_at | CHURC1 | 0.67 | 0.0002595 | yes |
| 237367_at | SLC9A1 | 0.67 | 9.70E-05 | yes |
| 227031_at | SNX10 | 0.67 | 3.64E-05 | no |
| 243062_at |  | 0.67 | 0.0006293 |  |

Figure 12

| | | | | |
|---|---|---|---|---|
| 212651_at | RHOBTB1 | 0.68 | 0.0003549 | no |
| 239033_at | | 0.68 | 0.0001358 | |
| 1556818_at | | 0.68 | 0.0006934 | |
| 232412_at | FBXL20 | 0.68 | 8.32E-05 | yes |
| 227224_at | RALGPS2 | 0.68 | 2.38E-05 | no |
| 1568964_x_at | SPN | 0.68 | 0.0007393 | yes |
| 227533_at | | 0.68 | 4.39E-05 | |
| 1563596_at | | 0.68 | 0.0004858 | |
| 228108_at | | 0.68 | 0.0007252 | |
| 223513_at | CENPJ | 0.70 | 0.0006315 | no |
| 230195_at | KIAA1958 | 0.70 | 4.80E-05 | yes |
| 227036_at | RASAL2 | 0.70 | 0.0001915 | yes |
| 228695_at | SLC46A3 | 0.70 | 0.000363 | yes |
| 203899_at | USP46 | 0.70 | 0.0002598 | yes |
| 239482_x_at | ZNF708 | 0.70 | 8.72E-05 | no |
| 236003_at | | 0.70 | 5.46E-05 | |
| 233239_at | | 0.70 | 0.0001189 | |
| 1558805_at | | 0.70 | 0.0000699 | |
| 238043_at | | 0.70 | 0.0007307 | |
| 1563453_at | | 0.70 | 0.000981 | |
| 221522_at | ANKRD27 | 0.71 | 7.84E-05 | no |
| 225731_at | ANKRD50 | 0.71 | 0.0004392 | yes |
| 224943_at | BTBD7 | 0.71 | 7.40E-05 | no |
| 203783_at | DYNC2LI1 | 0.71 | 0.0001116 | no |
| 218618_s_at | FNDC3B | 0.71 | 0.0003878 | no |
| 222880_at | ITPR2 | 0.71 | 0.0004874 | yes |
| 235978_at | LCORL | 0.71 | 1.75E-05 | no |
| 240693_at | LCORL | 0.71 | 7.81E-05 | no |
| 235392_x_at | PDE6 | 0.71 | 9.44E-05 | yes |
| 232500_at | RALGAPA3 | 0.71 | 0.000644 | no |
| 1553148_x_at | SNX13 | 0.71 | 8.23E-05 | no |
| 243465_at | | 0.71 | 0.0005366 | |
| 232599_at | EXOC6 | 0.72 | 0.0005936 | no |
| 225832_at | FNDC3B | 0.72 | 2.80E-05 | no |
| 213392_at | IGCK | 0.72 | 0.0005833 | yes |
| 224726_at | MBD1 | 0.72 | 0.0004937 | no |
| 239408_at | ZNF193 | 0.72 | 0.0003446 | no |
| 235178_at | | 0.72 | 5.01E-05 | |
| 83625_at | ABHD2 | 0.73 | 0.0005065 | yes |
| 222255_at | C18orf2 | 0.73 | 0.0054003 | no |
| 1570571_at | CCDC91 | 0.73 | 0.0008321 | no |

Figure 12 cont.

| | | | | |
|---|---|---|---|---|
| 222587_s_at | GALNT7 | 0.73 | 0.00075 | no |
| 203955_at | KIAA0649 | 0.73 | 5.33E-05 | yes |
| 209225_at | CCNI | 0.73 | 0.0004003 | no |
| 222830_at | RPX7 | 0.73 | 0.0001535 | yes |
| 204833_s_at | RPS6KA5 | 0.73 | 0.0001815 | no |
| 226366_at | SHPRH | 0.73 | 0.0006594 | no |
| 228995_at | USP46 | 0.73 | 5.33E-05 | yes |
| 205828_at | ZNF443 | 0.73 | 0.0002221 | no |
| 204291_at | ZNF184 | 0.73 | 0.0006949 | no |
| 243003_at | | 0.73 | 0.0001094 | |
| 233713_at | | 0.73 | 0.000377 | |
| 242343_x_at | | 0.73 | 0.0006754 | |
| 241825_at | | 0.73 | 0.0008831 | |
| 244532_at | | 0.73 | 0.0009613 | |
| 213304_at | FAM179B | 0.74 | 0.0002543 | no |
| 218313_s_at | GALNT7 | 0.74 | 0.0009507 | no |
| 227831_at | INO80D | 0.74 | 0.0005218 | yes |
| 242488_at | RALGPS2 | 0.74 | 6.30E-05 | no |
| 217797_x_at | SMARCA2 | 0.74 | 0.0004349 | no |
| 230758_at | SNX14 | 0.74 | 3.23E-05 | no |
| 233382_at | TSHZ1 | 0.74 | 0.0006712 | yes |
| 235739_x_at | ZNF187 | 0.74 | 0.0006873 | no |
| 218307_at | ZNF529 | 0.74 | 0.0008217 | yes |
| 239731_at | | 0.74 | 0.0001179 | |
| 233226_at | | 0.74 | 0.0004784 | |
| 214826_at | BRWD1 | 0.75 | 0.0003918 | no |
| 225833_at | CPT1B | 0.75 | 0.0006495 | no |
| 235030_at | FAM55C | 0.75 | 0.0009935 | no |
| 224016_at | HIPK2 | 0.75 | 0.0009617 | yes |
| 214457_at | HOXA2 | 0.75 | 0.0002801 | no |
| 224725_at | MBI | 0.75 | 0.0002308 | no |
| 223464_at | MGAPL5 | 0.75 | 7.36E-05 | yes |
| 238880_at | PSMG1 | 0.75 | 0.0006195 | no |
| 203883_s_at | RAB11FIP2 | 0.75 | 4.17E-05 | no |
| 202086_at | SLC39A6 | 0.75 | 6.53E-05 | no |
| 238896_at | TBL1XR1 | 0.75 | 0.0004402 | no |
| 1553118_at | THEM4 | 0.75 | 0.0008283 | no |
| 238029_x_at | UBR3 | 0.75 | 0.0001777 | no |
| 228562_at | ZSCAN29 | 0.75 | 8.40E-05 | no |
| 237096_at | | 0.75 | 0.0003813 | |
| 240478_at | | 0.75 | 0.0002859 | |

Figure 12 cont.

| | | | | |
|---|---|---|---|---|
| 238385_at | | 0.75 | 0.0004943 | |
| 240625_at | | 0.75 | 0.0008147 | |
| 238694_at | | 0.75 | 0.0008299 | |
| 213288_at | ANKRD12 | 0.76 | 0.0002188 | no |
| 228901_at | C17orf58 | 0.76 | 0.0006842 | no |
| 223219_at | CHURC1 | 0.76 | 8.47E-05 | yes |
| 1554164_at | GOAP2 | 0.76 | 5.03E-05 | yes |
| 226191_at | GSK3B | 0.76 | 0.0001726 | yes |
| 212057_at | KIAA0182 | 0.76 | 0.0003039 | yes |
| 227568_at | LNX2 | 0.76 | 3.93E-05 | no |
| 239694_at | MAPK8 | 0.76 | 0.0003438 | no |
| 233813_at | PBRM1 | 0.76 | 1.57E-05 | no |
| 213288_at | PIK3CB | 0.76 | 0.0004898 | no |
| 219862_at | PYROXD1 | 0.76 | 0.0006364 | no |
| 228338_at | RALGPS2 | 0.76 | 0.0001818 | no |
| 227268_at | RNF7 | 0.76 | 0.0002385 | no |
| 204685_at | RPS6KA5 | 0.76 | 5.63E-05 | no |
| 213804_at | RSBN1 | 0.76 | 0.0006087 | yes |
| 212821_at | SMYD2 | 0.76 | 0.0001919 | no |
| 341731_x_at | ZNF440 | 0.76 | 1.51E-05 | no |
| 223028_at | ZNF45 | 0.76 | 0.0001861 | no |
| 1558432_at | | 0.76 | 8.87E-05 | |
| 233383_at | | 0.76 | 0.0001946 | |
| 226318_at | | 0.76 | 0.0008819 | |
| 243820_at | | 0.76 | 0.0006517 | |
| 226898_at | ACAD8 | 0.77 | 0.0001613 | yes |
| 212500_at | ADO | 0.77 | 8.56E-05 | yes |
| 221825_at | ANGEL2 | 0.77 | 0.0008628 | no |
| 212798_s_at | ANKMY2 | 0.77 | 0.0001812 | no |
| 393525_s_at | APC | 0.77 | 0.0003395 | no |
| 224945_at | BTBD7 | 0.77 | 0.0003606 | no |
| 219872_s_at | C14orf135 | 0.77 | 0.0008631 | no |
| 223863_s_at | C19orf12 | 0.77 | 4.56E-05 | yes |
| 238148_at | C7orf62 | 0.77 | 0.0001894 | no |
| 212981_s_at | FAM118A | 0.77 | 0.000427 | no |
| 202815_s_at | FAM20B | 0.77 | 1.01E-05 | no |
| 203271_at | FBXO8 | 0.77 | 0.0002158 | yes |
| 223215_s_at | JKAMP | 0.77 | 8.58E-05 | no |
| 218008_at | KDM6A | 0.77 | 0.0001783 | yes |
| 232112_at | RALGPS2 | 0.77 | 9.73E-05 | no |
| 218499_at | RP5-213H19.1 | 0.77 | 0.0005841 | no |

Figure 12 cont.

| | | | | |
|---|---|---|---|---|
| 222793_s_at | RCBN1 | 0.77 | 0.0002179 | yes |
| 204156_at | SIK3 | 0.77 | 6.02E-05 | yes |
| 238630_at | SP3 | 0.77 | 0.0002189 | no |
| 218521_s_at | UBE2W | 0.77 | 0.0007051 | no |
| 234952_at | UBR3 | 0.77 | 8.58E-05 | no |
| 220343_at | ZBTB44 | 0.77 | 0.0008628 | yes |
| 229022_at | ZFX | 0.77 | 0.0003904 | no |
| 204523_at | ZNF148 | 0.77 | 0.0008089 | no |
| 209982_at | ZNF268 | 0.77 | 0.000887 | no |
| 50794_f_at | ZNF814 | 0.77 | 0.0007418 | no |
| 218638_s_at | ZXDC | 0.77 | 4.19E-05 | yes |
| 233838_at | | 0.77 | 5.15E-05 | |
| 244458_at | | 0.77 | 8.90E-05 | |
| 1555325_s_at | | 0.77 | 0.0001963 | |
| 237341_at | | 0.77 | 0.0002063 | |
| 1559723_s_at | | 0.77 | 0.0003848 | |
| 1558308_at | | 0.77 | 0.0008414 | |
| 228882_at | | 0.77 | 0.000883 | |
| 223297_at | AMMECR1L | 0.78 | 0.0003393 | yes |
| 228594_at | C5orf33 | 0.78 | 0.0001585 | yes |
| 204373_s_at | CEP290 | 0.78 | 0.0005928 | no |
| 203276_at | CUL2 | 0.78 | 0.0001172 | no |
| 228632_s_at | DENND1B | 0.78 | 0.0008895 | no |
| 201535_at | BF58 | 0.78 | 6.36E-05 | yes |
| 1563483_at | FAM91A2 | 0.78 | 4.76E-05 | no |
| 201734_at | GALNT1 | 0.78 | 0.0002651 | no |
| 201722_s_at | GALNT1 | 0.78 | 0.0008337 | no |
| 240682_at | HBS1L | 0.78 | 0.0009194 | no |
| 203011_at | IMPA1 | 0.78 | 0.0005389 | no |
| 213056_at | KIAA0182 | 0.78 | 7.78E-05 | yes |
| 209255_at | KLHDC10 | 0.78 | 0.000236 | no |
| 227601_at | METTL14 | 0.78 | 3.83E-05 | no |
| 205408_at | MLLT10 | 0.78 | 0.0001961 | yes |
| 213483_at | NIPBL | 0.78 | 0.0001484 | no |
| 223238_s_at | PBRM1 | 0.78 | 0.0002493 | no |
| 218453_at | POLR3B | 0.78 | 0.0008418 | no |
| 213049_at | RALGAPA1 | 0.78 | 0.0003032 | no |
| 203775_at | SLC25A13 | 0.78 | 0.0002159 | no |
| 229881_at | SLC35A4 | 0.78 | 0.0007427 | yes |
| 202088_s_at | SLC39A6 | 0.78 | 0.0003745 | no |
| 204496_at | STRN3 | 0.78 | 0.0008479 | no |

Figure 12 cont.

| | | | | |
|---|---|---|---|---|
| 204087_at | SUOX | 0.78 | 0.0005078 | yes |
| 218882_s_at | WDR3 | 0.78 | 0.0004948 | no |
| 213402_at | ZC3H13 | 0.78 | 0.0001191 | no |
| 207304_at | ZNF45 | 0.78 | 0.0006085 | no |
| 233851_at | ZNF684 | 0.78 | 0.0005523 | no |
| 241348_at | ZNF654 | 0.78 | 0.0006109 | no |
| 228896_at | | 0.78 | 8.34E-05 | |
| 243951_at | | 0.78 | 0.000228 | |
| 242772_x_at | | 0.78 | 0.0005289 | |
| 239976_at | | 0.78 | 0.000831 | |
| 229936_at | | 0.78 | 0.0007208 | |
| 1570394_at | | 0.78 | 0.0007658 | |
| 203291_at | CNOT4 | 0.79 | 0.0003755 | no |
| 218328_s_at | COX52 | 0.79 | 4.48E-05 | no |
| 212909_at | DNAJC16 | 0.79 | 0.0002277 | yes |
| 203983_s_at | E2F3 | 0.79 | 0.00058 | no |
| 238379_at | EXOC2 | 0.79 | 0.0001111 | yes |
| 228752_at | FAM174A | 0.79 | 0.0006898 | no |
| 238223_s_at | FBXL33 | 0.79 | 0.0004155 | yes |
| 225022_at | GOPC | 0.79 | 0.0005823 | yes |
| 204176_at | KLHL22 | 0.79 | 0.0005873 | no |
| 225463_at | MED1 | 0.79 | 0.0005078 | yes |
| 230828_s_at | MGC2752 | 0.79 | 8.27E-05 | no |
| 229925_at | NAA35 | 0.79 | 0.0002797 | no |
| 212829_s_at | PKN2 | 0.79 | 0.0004352 | no |
| 208396_at | PPM1B | 0.79 | 0.0005847 | no |
| 231173_at | PYROXD1 | 0.79 | 0.0005597 | no |
| 228298_at | RUNDC1 | 0.79 | 0.0008396 | yes |
| 1554666_s_at | SETD6 | 0.79 | 0.0001971 | no |
| 213034_at | SH3 | 0.79 | 9.10E-05 | yes |
| 229776_at | SLCO3A1 | 0.79 | 0.0001185 | yes |
| 226663_at | SOCS7 | 0.79 | 0.0006709 | yes |
| 201449_at | TIA1 | 0.79 | 0.0007791 | no |
| 203890_at | TUBGCP3 | 0.79 | 0.000182 | no |
| 218098_s_at | WDR11 | 0.79 | 2.52E-05 | no |
| 234881_at | ZXDC | 0.79 | 0.0003871 | yes |
| 227947_at | | 0.79 | 3.70E-05 | |
| 232963_at | | 0.79 | 6.99E-05 | |
| 223060_at | | 0.79 | 0.0003081 | |
| 243997_x_at | | 0.79 | 0.0006987 | |
| 238434_at | | 0.79 | 0.0007433 | |

Figure 12 cont.

| | | | | |
|---|---|---|---|---|
| 225543_at | | 0.79 | 0.0008825 | |
| 219494_s_at | AACS | 0.88 | 0.0006918 | no |
| 203526_s_at | APC | 0.88 | 9.69E-05 | no |
| 200831_x_at | APPBP2 | 0.88 | 0.0008198 | yes |
| 201878_at | ARIH1 | 0.88 | 0.0002333 | no |
| 201888_at | ARL1 | 0.88 | 1.86E-05 | no |
| 203486_s_at | ARMC8 | 0.88 | 0.000141 | no |
| 232515_at | ASB3 | 0.88 | 0.0008273 | no |
| 227777_at | C10orf18 | 0.88 | 0.0003238 | no |
| 217814_at | CCDC47 | 0.88 | 0.0001197 | no |
| 212911_at | DNAJC16 | 0.88 | 0.0008991 | yes |
| 243888_at | FAM55C | 0.88 | 0.0008953 | no |
| 1555871_s_at | FBX038 | 0.88 | 0.000018 | yes |
| 202272_s_at | FBXO28 | 0.88 | 0.0003735 | yes |
| 230494_at | IC41L | 0.88 | 0.0008581 | yes |
| 229429_x_at | LOC728855 | 0.88 | 0.0008025 | no |
| 225883_at | MLLT10 | 0.88 | 9.73E-05 | yes |
| 203237_s_at | MTFR1 | 0.88 | 0.0008093 | no |
| 218887_at | PJA1 | 0.88 | 0.0001821 | no |
| 213838_at | PKN2 | 0.88 | 0.0001519 | no |
| 227354_at | POU6F1 | 0.88 | 0.0003115 | no |
| 203288_x_at | PPP5K2 | 0.88 | 0.0001918 | yes |
| 213878_at | PYROXD1 | 0.88 | 0.0002706 | no |
| 208828_s_at | RAB14 | 0.88 | 0.0004482 | no |
| 214855_s_at | RALGAPA1 | 0.88 | 0.0007877 | no |
| 224616_at | ROD1 | 0.88 | 0.0000432 | yes |
| 238005_s_at | SAN34 | 0.88 | 0.0002709 | yes |
| 234288_at | SLC2413 | 0.88 | 1.56E-05 | no |
| 219057_at | SMG1 | 0.88 | 0.000428 | yes |
| 203310_at | STXBP3 | 0.88 | 0.0005135 | no |
| 238045_at | TMEM65 | 0.88 | 0.0002501 | no |
| 235401_at | TMEM878 | 0.88 | 0.0008145 | no |
| 208883_at | UBR5 | 0.88 | 0.0008899 | no |
| 235511_at | | 0.88 | 0.0001419 | |
| 1563347_at | | 0.88 | 0.0001514 | |
| 225543_at | | 0.88 | 0.0002055 | |
| 240618_at | | 0.88 | 0.000288 | |
| 1563867_at | | 0.88 | 0.0006839 | |
| 217358_at | | 0.88 | 0.0007146 | |
| 212832_at | ADO | 0.81 | 0.0003888 | yes |
| 201888_at | ARIH1 | 0.81 | 0.0001679 | no |

Figure 12 cont.

| | | | | |
|---|---|---|---|---|
| 225853_s_at | C19orf12 | 0.81 | 0.0001051 | yes |
| 217873_at | CAB39 | 0.81 | 7.94E-05 | no |
| 203533_s_at | CUL5 | 0.81 | 0.000121 | no |
| 203531_at | CUL5 | 0.81 | 0.0001771 | no |
| 228422_at | ERGIC2 | 0.81 | 0.0004973 | no |
| 218818_at | FAM13B | 0.81 | 0.0007344 | no |
| 244398_at | G3BP1 | 0.81 | 0.000399 | no |
| 243381_at | IMMT | 0.81 | 3.65E-05 | no |
| 212834_at | KIAA0776 | 0.81 | 0.000578 | no |
| 228446_at | KIAA2026 | 0.81 | 0.0008978 | no |
| 225288_at | KPNA4 | 0.81 | 0.0002119 | yes |
| 225387_at | KPNA4 | 0.81 | 0.0003595 | yes |
| 203238_s_at | MTFR1 | 0.81 | 8.72E-05 | no |
| 218382_at | NA435 | 0.81 | 0.0001986 | no |
| 203813_s_at | PAFAH1B1 | 0.81 | 0.0006456 | no |
| 202239_at | PARP4 | 0.81 | 0.0001985 | no |
| 220356_s_at | PBRM1 | 0.81 | 0.0003828 | no |
| 209438_at | PHKA2 | 0.81 | 0.0003692 | no |
| 227178_at | SLC2A13 | 0.81 | 0.0008984 | no |
| 228354_at | STAM2 | 0.81 | 4.34E-05 | no |
| 1554387_at | TRIM4 | 0.81 | 0.000183 | yes |
| 225088_at | USP40 | 0.81 | 0.0002582 | yes |
| 227541_at | WDR33 | 0.81 | 0.000149 | no |
| 237208_at | WDR61 | 0.81 | 0.0006387 | no |
| 235819_at | | 0.81 | 8.33E-05 | |
| 1560049_at | | 0.81 | 0.000208 | |
| 243895_at | | 0.81 | 0.0004244 | |
| 240277_at | | 0.81 | 0.0004582 | |
| 235893_at | | 0.81 | 0.0005443 | |
| 1554565_at | | 0.81 | 0.0005942 | |
| 1555580_a_at | | 0.81 | 0.0005325 | |
| 1555653_at | | 0.81 | 0.0005687 | |
| 227815_at | | 0.81 | 0.0005967 | |
| 202828_at | APPBP2 | 0.82 | 0.0005883 | yes |
| 212819_at | A2B1 | 0.82 | 0.0007887 | yes |
| 211484_x_at | C4BP8 | 0.82 | 0.0008133 | no |
| 223331_s_at | CCDC82 | 0.82 | 0.0008498 | no |
| 208996_at | DDX18 | 0.82 | 0.0005821 | no |
| 230974_at | DDX19B | 0.82 | 0.0005995 | no |
| 230647_x_at | FAM35A | 0.82 | 0.0001437 | no |
| 1557113_at | LOC283588 | 0.82 | 8.24E-05 | n.a. |

Figure 12 cont.

| | | | | |
|---|---|---|---|---|
| 235884_at | LOC644794 | 0.82 | 9.42E-05 | n.a. |
| 228085_at | LOC651280 | 0.82 | 0.000645 | n.a. |
| 1557985_at | MTERFD2 | 0.82 | 0.0003913 | no |
| 212885_at | OSBPL8 | 0.82 | 0.000683 | no |
| 215596_s_at | RNF160 | 0.82 | 0.0008331 | no |
| 223788_at | SEBN1 | 0.82 | 0.0002172 | yes |
| 224844_at | SLAIN2 | 0.82 | 9.05E-05 | no |
| 235241_at | SLC38A9 | 0.82 | 0.000683 | no |
| 202277_at | SPTLC1 | 0.82 | 1.73E-05 | no |
| 339465_x_at | TMEM168 | 0.82 | 0.0008555 | yes |
| 224734_at | TNRC6A | 0.82 | 0.0008564 | yes |
| 338494_at | TRAF3IP1 | 0.82 | 0.0007158 | no |
| 228945_at | ZNF655 | 0.82 | 0.0007733 | no |
| 1558762_a_at | | 0.82 | 7.42E-05 | |
| 1561783_at | | 0.82 | 0.0002281 | |
| 241997_at | | 0.82 | 0.0003381 | |
| 243253_at | | 0.82 | 0.0008888 | |
| 248023_at | | 0.82 | 0.0008719 | |
| 202818_s_at | FAM208 | 0.83 | 0.0008988 | no |
| 204703_at | IFT88 | 0.83 | 0.0002237 | no |
| 228387_at | KDM5A | 0.83 | 0.0005378 | yes |
| 228919_at | LYRM2 | 0.83 | 0.0003668 | no |
| 243833_at | MAP6D1 | 0.83 | 0.0002232 | no |
| 203427_at | MED1 | 0.83 | 0.000444 | yes |
| 223115_at | MED17 | 0.83 | 0.0003178 | no |
| 235552_at | METTL14 | 0.83 | 0.0003697 | no |
| 213594_at | PDCD4 | 0.83 | 0.0002948 | no |
| 201803_at | PPP1R12A | 0.83 | 0.0004048 | no |
| 334817_at | ROD1 | 0.83 | 0.0003319 | yes |
| 203734_s_at | RREB1 | 0.83 | 0.0003739 | yes |
| 226217_at | SLC30A7 | 0.83 | 0.0007446 | no |
| 214965_at | SPATA5 | 0.83 | 0.0004362 | yes |
| 218941_s_at | TAF1B | 0.83 | 0.0008691 | yes |
| 203733_at | TRIP4 | 0.83 | 0.0001738 | no |
| 233246_at | UHRF1BP1 | 0.83 | 0.0007008 | yes |
| 213128_at | UHRF1BP1L | 0.83 | 0.0001856 | no |
| 234639_at | UNQ1887 | 0.83 | 0.0003873 | no |
| 202745_at | USP8 | 0.83 | 0.0008862 | no |
| 313387_at | XAPAL | 0.83 | 0.0004036 | no |
| 212343_at | YIPF6 | 0.83 | 0.00823 | no |
| 202778_s_at | ZMYM2 | 0.83 | 0.0008663 | no |

Figure 12 cont.

| | | | | |
|---|---|---|---|---|
| 228145_s_at | ZNF398 | 0.83 | 0.0006652 | no |
| 235448_at | ZXDC | 0.83 | 3.30E-05 | yes |
| 1568171_at | | 0.83 | 0.0003508 | |
| 226137_at | | 0.83 | 0.0002751 | |
| 241184_x_at | | 0.83 | 0.0007178 | |
| 241152_at | | 0.83 | 0.0007838 | |
| 213382_at | APOOL | 0.84 | 0.0003949 | no |
| 218116_s_at | DCUN1D2 | 0.84 | 0.0007572 | no |
| 201786_at | DDX42 | 0.84 | 0.0003828 | yes |
| 212375_at | EP400 | 0.84 | 0.0002293 | yes |
| 218297_at | FAM188A | 0.84 | 0.0007626 | no |
| 224743_at | IMP4D1 | 0.84 | 0.0007519 | yes |
| 204177_s_at | KLHL23 | 0.84 | 9.15E-05 | no |
| 222506_at | LMBR1 | 0.84 | 0.0006385 | no |
| 223400_s_at | PBRM1 | 0.84 | 0.0007319 | no |
| 201493_s_at | PUM2 | 0.84 | 0.0003849 | no |
| 222445_at | SLC39A9 | 0.84 | 0.0002853 | no |
| 208623_at | TAF2 | 0.84 | 0.0005199 | no |
| 211987_at | TOP2B | 0.84 | 0.0009433 | no |
| 213031_s_at | WDR73 | 0.84 | 0.0004611 | yes |
| 212837_s_at | WWP1 | 0.84 | 0.0005733 | no |
| 1553693_at | ZNF101 | 0.84 | 8.42E-05 | no |
| 226002_at | ZNF398 | 0.84 | 0.0009908 | no |
| 217822_at | | 0.84 | 0.0004547 | |
| 221079_s_at | | 0.84 | 0.0008952 | |
| 228893_at | ABL2 | 0.85 | 0.0007314 | yes |
| 212547_at | BRD3 | 0.85 | 0.0005158 | no |
| 218660_at | C13orf3 | 0.85 | 0.000418 | yes |
| 231895_at | C9orf82 | 0.85 | 0.0007857 | no |
| 225747_at | C2CD4 | 0.85 | 0.0006502 | yes |
| 223956_s_at | DNAL1 | 0.85 | 0.0004634 | no |
| 201056_at | GOLGB1 | 0.85 | 0.0004708 | no |
| 208254_at | KLHDC10 | 0.85 | 0.0005505 | no |
| 1557086_at | LUC7L | 0.85 | 0.0003932 | no |
| 213224_s_at | NCAM1KKK1 | 0.85 | 0.0001294 | n.a. |
| 208231_s_at | OSBPL2 | 0.85 | 0.0009461 | no |
| 226073_at | PPHLN1 | 0.85 | 0.0001844 | no |
| 226527_at | RPRD2 | 0.85 | 0.0007514 | yes |
| 204587_at | SLC25A14 | 0.85 | 0.0009359 | no |
| 217786_s_at | TM9SF3 | 0.85 | 0.0001844 | yes |
| 234734_s_at | TNRC6A | 0.85 | 0.0009336 | yes |

Figure 12 cont.

| | | | | |
|---|---|---|---|---|
| 219163_at | ZNF562 | 0.85 | 0.0006627 | yes |
| 1553388_at | | 0.85 | 0.0004834 | |
| 241887_at | | 0.85 | 0.0005134 | |
| 237332_at | | 0.85 | 0.0005919 | |
| 212755_at | MON2 | 0.86 | 0.0006051 | no |
| 226835_at | THOC3 | 0.86 | 0.0006281 | no |
| 208773_s_at | | 0.86 | 0.000152 | |
| 238458_at | | 0.86 | 0.000897 | |
| 236334_at | | 0.86 | 0.0006251 | |
| 238552_at | | 0.87 | 0.0007782 | |

*The gene is not listed in the microrna.org database

Figure 12 cont.

Pathway analysis of the *miR-3151*-associated gene expression signature. Listed are the top ranking components of the categories biological functions and molecular/cellular functions.

| Biological Functions | P-value |
|---|---|
| Gene Expression (Transcriptional Regulation) | 3.56E-07-1.95E-02 |
| Cellular Development | 8.86E-07-2.57E-02 |
| Connective Tissue Development and Function | 8.86E-07-1.95E-02 |
| Cancer | 1.16E-06-3.61E-02 |
| Cell Cycle | 2.16E-05-2.57E-02 |
| Cellular Function and Maintenance | 2.91E-05-3.41E-02 |
| Skeletal and Muscular System Development and Function | 2.91E-05-2.2E-02 |
| Reproductive System Development and Function | 7.17E-05-1.95E-02 |
| Amino Acid Metabolism | 1.06E-04-1.95E-02 |
| Post-Translational Modification | 1.06E-04-1.99E-02 |
| Molecular and Cellular Functions | P-value |
| Gene Expression (Transcriptional Regulation) | 3.56E-07 - 1.95E-02 |
| Cellular Development | 8.86E-07 - 2.57E-02 |
| Cell Cycle | 2.16E-05 - 2.57E-02 |
| Cellular Function and Maintenance | 2.91E-05 - 3.41E-02 |
| Amino Acid Metabolism | 1.06E-04 - 1.95E-02 |

Figure 13

| Ingenuity Canonical Pathways | P-value | Ratio |
|---|---|---|
| p53 Signaling | 8.51E-05 | 9/96, 9.38E-02 |
| Cdc42 Signaling | 1.32E-04 | 10/180, 5.56E-02 |
| ERK/MAPK Signaling | 2.26E-04 | 12/204, 5.88E-02 |
| Breast Cancer Regulation by Stathmin1 | 3.9E-04 | 12/210, 5.71E-02 |
| B Cell Development | 2.02E-03 | 4/37, 1.08E-01 |

Fig. 26

| Primer name | sequence | Annealing temperature |
|---|---|---|
| TP53 ORF clon F (NheI) | gcgtgctagccATGGAGGAGCCGCAGTCAG | 64C |
| TP53 ORF clon R (BamHI) | gcgtggatccTCAGTCTGAGTCAG | |
| SP1 ORF clon F (NheI) | gcgtgctagcCACCATGAGCGACCAAGATC | 60C |
| SP1 ORF clon R (XhoI) | gcgtctcgagTCTCAGAAGCCATTGCCACTG | |
| miR-3151 stemloop cloning F | gcgtgctagcTGCAACAACTTTTGGACTAG | 58C |
| miR-3151 stemloop cloning R | gcgtggatccATCACAGGTGGTGTTACTAG | |
| RUNX1 ORF clon F (NheI) | gcaggctagcAGGAAGCGATGGCTTCAGAC | 60C |
| RUNX1 ORF clon R (EcoRI) | cgtcgaattcCGCCTCAGTAGGGCCTCCAC | |
| BAALC 1-6-8 ORF clon R (NheI) | gcgtgctagcGGATGGGCTGCGGCGGGAG | 58C |
| BAALC 1-6-8 ORF clon R (BamHI) | gcgtggatccGTTGACACAGTTCTTTGTGATTC | |

Fig. 27

| Primer name | sequence | Annealing temperature |
|---|---|---|
| TP53 miR-3151F (EcoRI) | cgtcgaattcGCAAGCACATCTGCATTTTC | 56C |
| TP53 miR-3151mut F (EcoRI) | cgtcgaattcGCAAGCACATCTGCATTTTCATTTCAC | |
| TSS-3151 clon F (KpnI) | gcacggtaccGTAGTCAGAGCGGTGGGATG | 58C |
| TSS-3151 clon R (SacI) | gtgcgagctcCAGAATGAGACAGACCTGAG | |
| TSS-3151 mut F2 | gcacggtaccGCGGTtttATtttTTGTCTAAATGTAC | 52C |
| TSS-3151 mut F1 | gcacggtaccAACACAGCTACGACCTCATG | |
| TSS-3151 mut R1 | gcacgagctcGAGTTCCAAAaaaaAaaaaACTGCTCAC | 52C |
| TSS-3151 mut R2 | gcacgagctcACAGAAGCTAGCAATCCATG | |
| TSS-BAALC clon F (KpnI) | gcacggtaccCTTGCTCACTTGGTTTATAG | 58C |
| TSS-BAALC clon R (SacI) | gtgcgagctcAGCTAGAGCTTGGTGAGCAC | |

Fig. 28

| Oligo name | sequence |
|---|---|
| BAALC promoter SP1 F EMSA | 5'/5Biosg/CCAGGATACCCCTCCACTTC |
| BAALC promoter SP1 R EMSA | 5'/5Biosg/GAAGTGGAGGGGTATCCTGG |
| miR3151 promoter NFKB F EMSA | 5'/5Biosg/CCTGTGGTCTTTCCTGTACA |
| miR3151 promoter NFKB R EMSA | 5'/5Biosg/GGACACCAGAAAGGACATGT |
| miR3151 promoter SP1 F EMSA | 5'/5Biosg/GCAGTGGGGTGGGGTTTGGA |
| miR3151 promoter SP1 R EMSA | 5'/5Biosg/TCCAAACCCCACCCCACTGC |

Fig. 29

SEQUENCE LISTING

<160> NUMBER OF SEQ ID NOS: 37

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgtcgaattc gttgccttga aatcactgtg                                    30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgtcgaattc atgcaaactg taaacacgac                                    30

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctgttgctcc cctttacact cttg                                          24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caagagtgta aaggggagca acag                                          24

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic

```
                                                       primer

<400> SEQUENCE: 5
cgtcgaattc ggcttctcac agtgtctcag                                   30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgtcgaattc ctcgtggaaa gagctcgcac                                   30

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gacttcatgg cctttactcg ttc                                          23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gaacgagtaa aggccatgaa gtc                                          23

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcgtgctagc catggaggag ccgcagtcag                                   30

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcgtggatcc tcagtctgag tcag                                         24

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 11
gcgtgctagc caccatgagc gaccaagatc                                30

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcgtctcgag tctcagaagc cattgccact g                              31

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcgtgctagc tgcaacaact tttggactag                                30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcgtggatcc atcacaggtg gtgttactag                                30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcaggctagc aggaagcgat ggcttcagac                                30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgtcgaattc cgcctcagta gggcctccac                                30

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 17
gcgtgctagc ggatgggctg cggcgggag                                    29

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcgtggatcc gttgacacag ttctttgtga ttc                               33

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgtcgaattc gcaagcacat ctgcattttc                                   30

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cgtcgaattc gcaagcacat ctgcattttc atttcac                           37

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcacggtacc gtagtcagag cggtgggatg                                   30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtgcgagctc cagaatgaga cagacctgag                                   30

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
```

```
gcacggtacc gcggttttat tttttgtcta aatgtac                                37
```

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
gcacggtacc aacacagcta cgacctcatg                                        30
```

<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
gcacgagctc gagttccaaa aaaaaaaaaa ctgctcac                               38
```

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
gcacgagctc acagaagcta gcaatccatg                                        30
```

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
gcacggtacc cttgctcact tggtttatag                                        30
```

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
gtgcgagctc agctagagct tggtgagcac                                        30
```

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ccaggatacc cctccacttc					20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gaagtggagg ggtatcctgg					20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cctgtggtct ttcctgtaca					20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggacaccaga aaggacatgt					20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gcagtggggt ggggtttgga					20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tccaaacccc accccactgc					20

<210> SEQ ID NO 35
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ggatccgggt ggggtaatgg gataagatct tcctgtcaga cctgatccca ttgccccacc		60

-continued tttttgaatt c                                                          71

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tggactaggg taacggggtg g                                               21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
acctgatccc attgccccac c                                               21

METHODS AND COMPOSITIONS USING MIR-3151 IN THE DIAGNOSIS AND TREATMENT OF CANCER

CROSS-REFERENCE TO RELATED APPLICATIONS

This is non-provisional application which claims the benefit of U.S. Provisional Application Nos. 61/618,833, filed Apr. 1, 2012, and 61/790,784, filed Mar. 15, 2013 the entire disclosures of which are expressly incorporated herein by reference for all purposes.

STATEMENT REGARDING FEDERALLY SPONSORED RESEARCH

This invention was made with government support under Grant Nos. CA101140, CA114725, CA140158, CA31946, CA33601, CA16058, CA77658 and CA129657, awarded by the National Institutes of Health. The government has certain rights in the invention.

SEQUENCE LISTING

The instant application contains a Sequence Listing which has been submitted via EFS-web and is hereby incorporated by reference in its entirety. The ASCII copy, created on Apr. 1, 2013, is named 604__53695_SEQ_LIST_11126.txt, and is 8881 bytes in size.

FIELD OF THE INVENTION

This invention relates generally to the fields of cancer and molecular biology. The invention provides methods for predicting increased risk of developing cancer, particularly leukemia, methods of determining prognosis, and methods of treating cancers, including leukemia, melanoma, and thyroid cancer.

BACKGROUND

Overexpression of the brain and acute leukemia, cytoplasmic (BAALC) gene is implicated in myeloid leukemogenesis and associated with poor outcome in both acute myeloid leukemia (AML) and acute lymphoblastic leukemia (ALL) patients. Additionally, high BAALC expression occurs in glioblastoma, melanoma, and childhood gastrointestinal stroma tumors.

Acute myeloid leukemia (AML) is a cytogenetically and molecularly heterogeneous disease. AML is characterized by clonal proliferation of myeloid precursors and maturation arrest of myeloid cells in the bone marrow. Despite cytogenetic- and molecular-based stratification in risk-adapted therapies, 20% to 30% of younger (<60 years) AML patients never achieve a complete remission (CR) and 50% of those who achieve CR later experience disease relapse. Older AML patients fare much worse with a two-year median overall survival (OS) of approximately 6%. These numbers show that despite recent advances in understanding AML pathogenesis, overall prognosis remains poor.

Conventional approaches to treating cancer, including hematologic malignancies, and to predicting and assessing cancer and cancer cell responses to specific treatment regimens rely on properly classifying the type of tumor present. Proper classification, in turn, relies primarily on clinical features, tumor cell morphology, tumor cell immunophenotype and, to a lesser extent, on tumor cell chromosomal abnormalities. However, even within a given tumor type, response to specific treatment regimens can be variable, and analyses at the molecular level reveal that the tumor types defined by conventional classification schemes are, often, quite heterogeneous.

Recent efforts to classify tumors, including hematologic malignancies, have, therefore, focused on identifying the specific genetic abnormalities or molecular triggers that drive the growth or pathology of specific tumor types. Such genetic abnormalities or molecular triggers can then serve as markers of disease and/or as targets for therapy.

Tumor protein 53, (also known as tp53, p53, and protein 53), is a tumor suppressor protein that is encoded by the TP53 gene. It is important in cancer suppression, and plays a role in apoptosis, genomic stability, and inhibition of angiogenesis.

It would be desirable and advantageous to have one or a combination of biomarkers which could be used to determine a subject's risk of disease, response to an agent, or the suitability of a subject to treatment with one or more agents using various doses and dose regimens.

In addition, there is a need in the art for methods of down-regulating the expression of genes associated with tumorigenesis or cell transformation to treat or prevent cancer. It would be desirable to have additional therapeutic compounds for treating leukemia and other cancers.

SUMMARY

The inventions described and claimed herein have many attributes and embodiments including, but not limited to, those set forth or described or referenced in this Summary. It is not intended to be all-inclusive and the inventions described and claimed herein are not limited to or by the features or embodiments identified in this Summary, which is included for purposes of illustration only and not restriction.

In a broad aspect, there is provided herein a method of diagnosing whether a subject has a poor prognostic outcome for acute myeloid leukemia.

In another broad respect, there are provided treatment options for leukemia patients with deregulated miR-3151/BAALC and ultimately TP53 expression levels. In another broad respect, there are provided treatment options for melanoma. Compositions comprising therapeutic oligonucleotide compounds that target the expression of genes associated with tumorigenesis or cell transformation are provided.

Methods are described to manipulate and treat the oncogenic deregulation of the TP53-associated apoptosis pathway associated with leukemogenesis.

The therapeutic use of proteasome inhibitors is described.

In another broad respect, there are provided treatment options for thyroid cancer.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

(FIG. 1A) Disease-free survival, and (FIG. 1B) Overall survival.

(FIG. 2A) Disease-free survival, and (FIG. 2B) Overall survival.

(FIG. 3A) Disease-free survival, and (FIG. 3B) Overall survival.

FIG. 4A. GEP. Upregulated and downregulated genes that are mentioned in the text are indicated along the side.

FIG. 4B. MEP. Upregulated and downregulated microRNAs are indicated along the side.

FIG. 5C shows the validation of increased miR-3151 expression levels after lentiviral infection. FIG. 5D shows a Western Blot of FBXL20 expression comparing miR-3151 infected KG1 cells versus scramble control. miR-3151 expression results in elimination of the FBXL20 protein. The effect of miR-3151 on luciferase activity is shown for the FBXL20 and USP40 3*-UTRs (cloned 3* of the luciferase gene) in FIG. 5E and FIG. 5F, respectively. Addition of miR-3151 resulted in a decreased of luciferase activity compared relative to scramble control of 54% for FBXL20 and of 33% for USP40 (±s.d., both P≤0.001). This effect was abrogated after mutation of the respective binding sequences of the predicted miR-3141 binding sites.

FIG. 6—Table: Clinical and molecular characteristics according to miR-3151 expression status in CN-AML patients aged 60 years and older.

FIG. 7—Table: Multivariable analysis for outcome according to the miR-3151 expression status in older patients with cytogenetically normal acute myeloid leukemia (CN-AML).

FIG. 8—Table: Bivariable models for outcome according to the expression status of miR-3151 and BAALC in older patients with CN-AML.

FIG. 9—Table: Outcome analysis according to miR-3151 expression status and ELN genetic group in older patients with CN-AML.

FIG. 10—Table: Primer sequences and corresponding annealing temperatures for cloning and mutational sequence changes of the FBXL20 and USP40 3'-UTRs, [SEQ ID NOS: 1-8].

FIG. 11—Table: miR-3151-associated gene expression signature in CN-AML patients: Upregulated genes. High miR-3151 expresser status was associated with the upregulation of 192 probe sets (116 annotated genes) out of 24,649 investigated (Global test P-value=0.001).

FIG. 12—Table: miR-3151-associated gene expression signature in CNAML patients: Downregulated genes. High miR-3151 expresser status was associated with the downregulation of 405 probe sets (258 annotated genes) out of 24,649 investigated (Global test P-value=0.001). Seventy-three of the downregulated genes are in-silico predicted targets of miR-3151 (microma.org). Highlighted in grey are the probe-sets corresponding to annotated genes of the in-silico targets which showed ≥25% downregulation with a P-value <0.0001.

FIG. 13—Table: Pathway analysis of the miR-3151-associated gene expression signature. Listed are the top ranking components of the categories biological functions and molecular/cellular functions.

FIG. 21. miR-3151 deregulates the TP53 pathway and directly targets TP53.

FIG. 23. Forced miR-3151 expression leads to increased growth and viability of AML cells and is potentiated by co-infection with its host gene BAALC.

FIG. 26. Canonical pathway analysis of the miR-3151-associated gene expression signature. Listed are the top ranking components of the canonical pathway category. TP53 signaling was identified as the top canonical pathway (Ratio: 9/96 [0.094], P=8.51E-05).

FIG. 27. Primer sequences for overexpression constructs. In order of appearance, SEQ ID NOS: 9-18.

FIG. 28. Primer sequences for luciferase constructs. In order of appearance, SEQ ID NOS: 19-28.

FIG. 29. Oligo sequences for Electrophoretic Mobility Shift Assays. In order of appearance, SEQ ID NOS: 29-34.

DETAILED DESCRIPTION

Figure 1A:
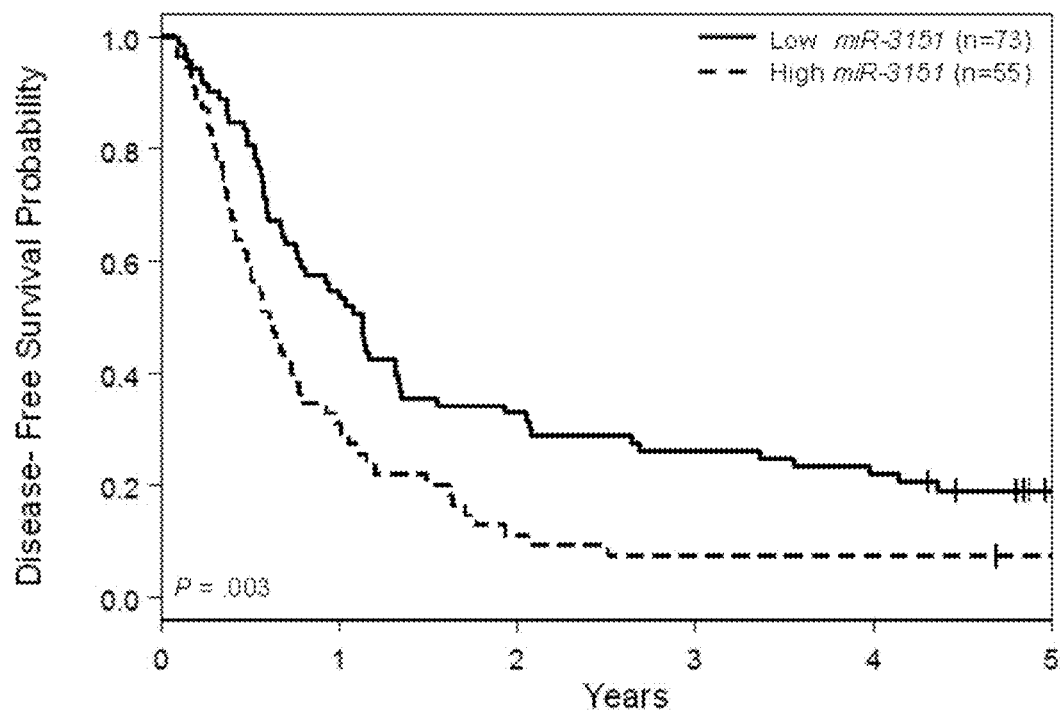
FIG. 1A-FIG. 1B. Outcome of cytogenetically normal (CN-AML) patients 60 years of age or older with respect to miR-3151 expression.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

miRNAs

As used herein interchangeably, a "miR gene product," "microRNA," "miR," or "miRNA" refers to the unprocessed (e.g., precursor) or processed (e.g., mature) RNA transcript from a miR gene. As the miR gene products are not translated into protein, the term "miR gene products" does not include proteins. The unprocessed miR gene transcript is also called a "miR precursor" or "miR prec" and typically comprises an RNA transcript of about 70-100 nucleotides in length. The miR precursor can be processed by digestion with an RNAse (for example, Dicer, Argonaut, or RNAse III (e.g., E. coli RNAse III)) into an active 19-25 nucleotide RNA molecule. This active 19-25 nucleotide RNA molecule is also called the "processed" miR gene transcript or "mature" miRNA.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having been processed from the miR precursor. When a microRNA is referred to herein by name, the name corresponds to both the precursor and mature forms, unless otherwise indicated.

Measuring miRNAs

The level of at least one miR gene product can be measured in a biological sample (e.g., cells, tissues) obtained from the subject. For example, a blood sample can be removed from the subject, and blood cells (e.g., white blood cells) can be isolated for DNA extraction by standard techniques. The blood or tissue sample is preferably obtained from the subject prior to initiation of radiotherapy, chemotherapy or other therapeutic treatment. A corresponding control tissue or blood sample can be obtained from unaffected tissues of the subject, from a normal human individual or population of normal individuals, or from cultured cells corresponding to the majority of cells in the subject's sample. The control tissue or blood sample is then processed along with the sample from the subject, so that the levels of miR gene product produced from a given miR gene in cells from the subject's sample can be compared to the corresponding miR gene product levels from cells of the control sample. A reference miR expression standard for the biological sample can also be used as a control.

An alteration (e.g., an increase or decrease) in the level of a miR gene product in the sample obtained from the subject, relative to the level of a corresponding miR gene product in a control sample, is indicative of the presence of a leukemia in the subject. Unless otherwise specified, "control" indicates a non-cancerous type control.

A cancerous reference, like a non-cancerous control, may be obtained from a tissue sample or tumor of known type. A cancerous reference may include a reference signature which defines a standard expression level for each gene, mRNA, and/or miRNA and a significant change direction for a particular disease state. A match (e.g. a similar value within a range) in the level of a mRNA and/or miR gene product in the sample obtained from the subject, relative to the level of a corresponding mRNA and/or miR gene product in a cancerous reference sample, is indicative of the presence of a cancer-related disease in the subject.

In one embodiment, the level of the at least one miR gene product in the test sample is greater than the level of the corresponding miR gene product in the control sample (i.e., expression of the miR gene product is "up-regulated"). As used herein, expression of a miR gene product is "up-regulated" when the amount of miR gene product in a cell or tissue sample from a subject is greater than the amount of the same gene product in a control cell or tissue sample.

In another embodiment, the level of the at least one miR gene product in the test sample is less than the level of the corresponding miR gene product in the control sample (i.e., expression of the miR gene product is "down-regulated"). As used herein, expression of a miR gene is "down-regulated" when the amount of miR gene product produced from that gene in a cell or tissue sample from a subject is less than the amount produced from the same gene in a control cell or tissue sample.

The relative miR gene expression in the control and normal samples can be determined with respect to one or more RNA expression standards. The standards can comprise, for example, a zero miR gene expression level, the miR gene expression level in a standard cell line, the miR gene expression level in unaffected tissues of the subject, or the average level of miR gene expression previously obtained for a population of normal human controls.

The level of a miR gene product in a sample can be measured using any technique that is suitable for detecting RNA expression levels in a biological sample. Suitable techniques (e.g., Northern blot analysis, RT-PCR, in situ hybridization) for determining RNA expression levels in a biological sample (e.g., cells, tissues) are well known to those of skill in the art. In a particular embodiment, the level of at least one miR gene product is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

Suitable probes for Northern blot hybridization of a given miR gene product can be produced from the nucleic acid sequences provided in the figures and include, but are not limited to, probes having at least about 70%, 75%, 80%, 85%, 90%, 95%, 98%, 99% or complete complementarity to a miR gene product of interest. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are incorporated herein by reference.

For example, the nucleic acid probe can be labeled with, e.g., a radionuclide, such as $^3$H, $^{32}$P, $^{33}$P, $^{14}$C, or $^{35}$S; a heavy metal; a ligand capable of functioning as a specific binding pair member for a labeled ligand (e.g., biotin, avidin or an antibody); a fluorescent molecule; a chemiluminescent molecule; an enzyme or the like.

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylyated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. Suitable probes for in situ hybridization of a given miR gene product can be produced from the nucleic acid sequences, and include, but are not limited to, probes having at least about 70%, 75%, 80%, 85%, 90%, 95%, 98%, 99% or complete complementarity to a miR gene product of interest, as described above.

The relative number of miR gene transcripts in cells can also be determined by reverse transcription of miR gene transcripts, followed by amplification of the reverse-transcribed transcripts by polymerase chain reaction (RT-PCR). The levels of miR gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). Methods for performing quantitative and semi-quantitative RT-PCR, and variations thereof, are well known to those of skill in the art.

In some instances, it may be desirable to simultaneously determine the expression level of a plurality of different miR gene products in a sample. In other instances, it may be desirable to determine the expression level of the transcripts of all known miR genes correlated with a cancer. Assessing cancer-specific expression levels for hundreds of miR genes or gene products is time consuming and requires a large amount of total RNA (e.g., at least 20 μg for each Northern blot) and autoradiographic techniques that require radioactive isotopes.

To overcome these limitations, an oligolibrary, in microchip format (i.e., a microarray), may be constructed containing a set of oligonucleotide (e.g., oligodeoxynucleotides) probes that are specific for a set of miR genes. Using such a microarray, the expression level of multiple microRNAs in a biological sample can be determined by reverse transcribing the RNAs to generate a set of target oligodeoxynucleotides, and hybridizing them to probe the oligonucleotides on the microarray to generate a hybridization, or expression, profile. The hybridization profile of the test sample can then be compared to that of a control sample to determine which microRNAs have an altered expression level in cancer cells. As used herein, "probe oligonucleotide" or "probe oligodeoxynucleotide" refers to an oligonucleotide that is capable of hybridizing to a target oligonucleotide. "Target oligonucleotide" or "target oligodeoxynucleotide" refers to a molecule to be detected (e.g., via hybridization). By "miR-specific probe oligonucleotide" or "probe oligonucleotide specific for a miR" is meant a probe oligonucleotide that has a sequence selected to hybridize to a specific miR gene product, or to a reverse transcript of the specific miR gene product.

Expression Profile

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal cells may be distinguished from cancerous cells, and within cancerous cells, different prognosis states (for example, good or poor long term survival prospects) may be determined. By comparing expression profiles of cancer cells in different states, information regarding which genes are important (including both up- and down-regulation of genes) in each of these states is obtained. The identification of sequences that are differentially expressed in cancer cells, as well as differential expression resulting in different prognostic outcomes, allows the use of this information in a number of ways. For example, a particular treatment regime may be evaluated (e.g., to determine whether a chemotherapeutic drug acts to improve the long-term prognosis in a particular patient) Similarly, diagnosis may be done or confirmed by comparing patient samples with known expression profiles. Furthermore, these gene expression profiles (or individual genes) allow screening of drug candidates that suppress the cancer expression profile or convert a poor prognosis profile to a better prognosis profile.

Accordingly, the invention provides methods of diagnosing whether a subject has, or is at risk for developing, a AML and/or ALL cancer, comprising reverse transcribing RNA from a test sample obtained from the subject to provide a set of target oligodeoxynucleotides, hybridizing the target oligodeoxynucleotides to a microarray comprising miRNA-specific probe oligonucleotides to provide a hybridization profile for the test sample, and comparing the test sample hybridization profile to a hybridization profile generated from a control sample or reference standard, wherein an alteration in the signal of at least one miRNA is indicative of the subject either having, or being at risk for developing, a leukemia.

Microarrays

In one embodiment, the microarray comprises miRNA-specific probe oligonucleotides for a substantial portion of all known human miRNAs.

In a particular embodiment, the microarray comprises miRNA-specific probe oligonucleotides for miR-3151 (miR Base Accession for hsa-miR-3151 stem-loop: MI0014178; miR Base Accession for hsa-miR-3151 mature sequence: MIMAT0015024).

The microarray can be prepared from gene-specific oligonucleotide probes generated from known miRNA sequences. The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs or other RNAs (e.g., rRNAs, mRNAs) from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/30% formamide at 25° C. for 18 hours, followed by washing in 0.75×TNT (Tris HCl/NaCl/Tween 20) at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRs, in the patient sample. According to one embodiment, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding miR in the patient sample.

The use of the array has several advantages for miRNA expression detection. First, the global expression of several hundred genes can be identified in the same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 μg of total RNA. The relatively limited number of miRNAs (a few hundred per species) allows the construction of a common microarray for several species, with distinct oligonucleotide probes for each. Such a tool would allow for analysis of trans-species expression for each known miR under various conditions.

Microchips

In addition to use for quantitative expression level assays of specific miRs, a microchip containing miRNA-specific probe oligonucleotides corresponding to a substantial portion of the miRNome, preferably the entire miRNome, may be employed to carry out miR gene expression profiling, for analysis of miR expression patterns. Distinct miR signatures can be associated with established disease markers, or directly with a disease state.

According to the expression profiling methods described herein, total RNA from a sample from a subject suspected of having a cancer (e.g., AML and/or ALL) is quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal). More preferably, the profile recorded includes the intensity of the signal from each hybridization. The profile is compared to the hybridization profile generated from a normal, i.e., noncancerous, control sample. An alteration in the signal is indicative of the presence of, or propensity to develop, cancer in the subject.

Other techniques for measuring miR gene expression are also within the skill in the art, and include various techniques for measuring rates of RNA transcription and degradation.

The invention also provides methods of determining the prognosis of a subject with AML and/or ALL, comprising measuring the level of at least one miR gene product, which is associated with a particular prognosis (e.g., a good or positive prognosis, a poor or adverse prognosis), in a test sample from the subject. According to these methods, an alteration in the level of a miR gene product that is associated with a particular prognosis in the test sample, as compared to the level of a corresponding miR gene product in a control sample, is indicative of the subject having a cancer with a particular prognosis.

In one embodiment, the miR gene product is associated with an adverse (i.e., poor) prognosis. Examples of an adverse prognosis include, but are not limited to, low survival rate and rapid disease progression. In certain embodiments, the level of the at least one miR gene product is measured by reverse transcribing RNA from a test sample obtained from the subject to provide a set of target oligodeoxynucleotides, hybridizing the target oligodeoxynucleotides to a microarray that comprises miRNA-specific probe oligonucleotides to provide a hybridization profile for the test sample, and comparing the test sample hybridization profile to a hybridization profile generated from a control sample.

Without wishing to be bound by any one theory, it is believed that alterations in the level of one or more miR gene products in cells can result in the deregulation of one or more intended targets for these miRs, which can lead to the formation of leukemias such as AML and ALL.

Therefore, altering the level of the miR gene product (e.g., by decreasing the level of a miR gene product that is up-regulated in cancer cells, by increasing the level of a miR gene product that is down-regulated in cancer cells) may successfully treat the leukemias.

Accordingly, the present invention encompasses methods of inhibiting leukemias in a subject who has, or is suspected of having, a leukemia wherein at least one miR gene product is deregulated (e.g., down-regulated, up-regulated) in the cancer cells of the subject.

When the at least one isolated miR gene product is up-regulated in the cancer cells, the method comprises administering to the subject an effective amount of at least one compound for inhibiting expression of the at least one miR gene product, referred to herein as miR gene expression-inhibition compounds, such that proliferation of cancer cells is inhibited.

The isolated miR gene product that is administered to the subject can be identical to the endogenous wild-type miR gene product that is up-regulated in the cancer cell or it can be a variant or biologically-active fragment thereof. As defined herein, a "variant" of a miR gene product refers to a miRNA that has less than 100% identity to a corresponding wild-type miR gene product and possesses one or more biological activities of the corresponding wild-type miR gene product. Examples of such biological activities include, but are not limited to, inhibition of expression of a target RNA molecule (e g, inhibiting translation of a target RNA molecule, modulating the stability of a target RNA molecule, inhibiting processing of a target RNA molecule) and inhibition of a cellular process associated with leukemias (e.g., cell differentiation, cell growth, cell death). These variants include species variants and variants that are the consequence of one or more mutations (e.g., a substitution, a deletion, an insertion) in a miR gene. In certain embodiments, the variant is at least about 70%, 75%, 80%, 85%, 90%, 95%, 98%, or 99% identical to a corresponding wild-type miR gene product.

As defined herein, a "biologically-active fragment" of a miR gene product refers to an RNA fragment of a miR gene product that possesses one or more biological activities of a corresponding wild-type miR gene product. As described above, examples of such biological activities include, but are not limited to, inhibition of expression of a target RNA molecule and inhibition of a cellular process associated with cancer. In certain embodiments, the biologically-active fragment is at least about 5, 7, 10, 12, 15, or 17 nucleotides in length. In a particular embodiment, an isolated miR gene product can be administered to a subject in combination with one or more additional anti-cancer treatments. Suitable anti-cancer treatments include, but are not limited to, chemotherapy, radiation therapy and combinations thereof (e.g., chemoradiation).

A miR gene expression-inhibiting compound can be administered to a subject in combination with one or more additional anti-cancer treatments. Suitable anti-cancer treatments include, but are not limited to, chemotherapy, radiation therapy and combinations thereof (e.g., chemoradiation).

The terms "treat", "treating" and "treatment", as used herein, refer to ameliorating symptoms associated with a disease or condition, including preventing or delaying the onset of the disease symptoms, and/or lessening the severity or frequency of symptoms of the disease or condition. The terms "subject", "patient" and "individual" are defined herein to include animals, such as mammals, including, but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

As used herein, an "effective amount" of an isolated miR gene product is an amount sufficient to inhibit proliferation of a cancer cell in a subject suffering from a leukemia.

One skilled in the art can readily determine an effective amount of a miR gene product to be administered to a given subject, by taking into account factors, such as the size and weight of the subject; the extent of disease penetration; the age, health and sex of the subject; the route of administration; and whether the administration is regional or systemic.

An effective amount of an isolated miR gene product can also be based on the approximate or estimated body weight of a subject to be treated. Preferably, such effective amounts are administered parenterally or enterally, as described herein. For example, an effective amount of the isolated miR gene product is administered to a subject can range from about 5-3000 micrograms/kg of body weight, from about 700-1000 micrograms/kg of body weight, or greater than about 1000 micrograms/kg of body weight.

One skilled in the art can also readily determine an appropriate dosage regimen for the administration of an isolated miR gene product to a given subject. For example, a miR gene product can be administered to the subject once (e.g., as a single injection or deposition). Alternatively, a miR gene product can be administered once or twice daily to a subject for a period of from about three to about twenty-eight days, more particularly from about seven to about ten days. In a particular dosage regimen, a miR gene product is administered once a day for seven days. Where a dosage regimen comprises multiple administrations, it is understood that the effective amount of the miR gene product administered to the subject can comprise the total amount of gene product administered over the entire dosage regimen.

Isolated miR Gene Products

As used herein, an "isolated" miR gene product is one that is synthesized, or altered or removed from the natural state through human intervention. For example, a synthetic miR gene product, or a miR gene product partially or completely separated from the coexisting materials of its natural state, is considered to be "isolated." An isolated miR gene product can exist in substantially-purified form, or can exist in a cell into which the miR gene product has been delivered. Thus, a miR gene product that is deliberately delivered to, or expressed in, a cell is considered an "isolated" miR gene product. A miR gene product produced inside a cell from a miR precursor molecule is also considered to be an "isolated" molecule. According to the invention, the isolated miR gene products described herein can be used for the manufacture of a medicament for treating a leukemia in a subject (e.g., a human).

Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

Inhibiting miR Expression

In other embodiments of the treatment methods of the invention, an effective amount of at least one compound that inhibits miR expression can be administered to the subject. As used herein, "inhibiting miR expression" means that the production of the precursor and/or active, mature form of miR gene product after treatment is less than the amount produced prior to treatment. One skilled in the art can readily determine whether miR expression has been inhibited in a cancer cell, using, for example, the techniques for determining miR transcript level discussed above for the diagnostic method. Inhibition can occur at the level of gene expression (i.e., by inhibiting transcription of a miR gene encoding the miR gene product) or at the level of processing (e.g., by inhibiting processing of a miR precursor into a mature, active miR).

As used herein, an "effective amount" of a compound that inhibits miR expression is an amount sufficient to inhibit proliferation of a cancer cell in a subject suffering from a leukemia. One skilled in the art can readily determine an effective amount of a miR expression-inhibition compound to be administered to a given subject, by taking into account factors, such as the size and weight of the subject; the extent of disease penetration; the age, health and sex of the subject; the route of administration; and whether the administration is regional or systemic.

For example, an effective amount of the expression-inhibition compound can be based on the estimated body weight of a subject to be treated. One skilled in the art can also readily determine an appropriate dosage regimen for administering a compound that inhibits miR expression to a given subject. The compound may, for example, antagonize miR expression or miR activity. In one embodiment, a compound that inhibits miR expression is an antagomiR containing the complementary sequence to miR-3151.

Suitable compounds for inhibiting miR gene expression include double-stranded RNA, antisense nucleic acids, and enzymatic RNA molecules, such as ribozymes. Each of these compounds can be targeted to a given miR gene product and interfere with the expression of (e.g., inhibit translation of, induce cleavage or destruction of) the target miR gene product.

The term "interfering RNA" or "RNAi" or "interfering RNA sequence" as used herein includes single-stranded RNA (e.g., mature miRNA, ssRNAi oligonucleotides, ssDNAi oligonucleotides), double-stranded RNA (i.e., duplex RNA such as siRNA, Dicer-substrate dsRNA, shRNA, aiRNA, or pre-miRNA), a DNA-RNA hybrid, or a DNA-DNA hybrid, that is capable of reducing or inhibiting the expression of a target gene or sequence. RNA interference (RNAi) is an evolutionarily conserved process in which recognition of double-stranded RNA (dsRNA) ultimately leads to posttranscriptional suppression of gene expression. RNAi provides a useful approach to downregulate or silence the transcription and translation of a gene of interest. In particular, for the treatment of neoplastic disorders such as cancer, RNAi may be used to modulate the expression of certain genes, such as: an anti-apoptotic molecule, a growth factor, a growth factor receptor, a mitotic spindle protein, a cell cycle protein, an angiogenic factor, an oncogene, an intracellular signal transducer, a molecular chaperone, and combinations thereof.

Inducing RNA Interference

Expression of a given miR gene can be inhibited, for example, by inducing RNA interference of the miR gene with an isolated double-stranded RNA ("dsRNA") molecule which has at least 90%, for example at least 95%, at least 98%, at least 99%, or 100%, sequence homology with at least a portion of the miR gene product. In a particular embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence that is substantially identical to a nucleic acid sequence contained within the target miR gene product.

As used herein, a nucleic acid sequence in an siRNA which is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in certain embodiments, the siRNA comprises at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above for the isolated miR gene products.

Antisense

Expression of a given miR gene can also be inhibited by an antisense nucleic acid. As used herein, an "antisense nucleic acid" refers to a nucleic acid molecule that binds to target RNA by means of RNA-RNA, RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, peptide nucleic acid (PNA)) that generally comprise a nucleic acid sequence complementary to a contiguous nucleic acid sequence in a miR gene product. The antisense nucleic acid can comprise a nucleic acid sequence that is 50-100% complementary, 75-100% complementary, or 95-100% complementary to a contiguous nucleic acid sequence in a miR gene product.

Nucleic acid sequences for the miR gene products are described in the Examples and Figures. Without wishing to be bound by any theory, it is believed that the antisense nucleic acids activate RNase H or another cellular nuclease that digests the miR gene product/antisense nucleic acid duplex.

Antisense nucleic acids can also contain modifications to the nucleic acid backbone or to the sugar and base moieties (or their equivalent) to enhance target specificity, nuclease resistance, stability, hybridization, solubility, delivery or other properties related to efficacy of the molecule. Such modifications include cholesterol moieties, duplex intercalators, such as acridine, or one or more nuclease-resistant groups. An antisense oligonucleotide can be, for example, about 5, 10, 15, 20, 25, 30, 35, 40, 45, or 50 or more nucleotides in length. An antisense oligonucleotide can be constructed using chemical synthesis and enzymatic ligation reactions using procedures known in the art. Antisense nucleic acids can be produced chemically or biologically, or can be expressed from a recombinant plasmid or viral vector, as described above for the isolated miR gene products.

Enzymatic Nucleic Acids

Expression of a given miR gene can also be inhibited by an enzymatic nucleic acid. As used herein, an "enzymatic nucleic acid" refers to a nucleic acid comprising a substrate binding region that has complementarity to a contiguous nucleic acid sequence of a miR gene product, and which is able to specifically cleave the miR gene product. The enzymatic nucleic acid substrate binding region can be, for example, 50-100% complementary, 75-100% complementary, or 95-100% complementary to a contiguous nucleic acid sequence in a miR gene product. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described below for the isolated miR gene products.

Plasmids

Alternatively, the miR gene products can be expressed from recombinant circular or linear DNA plasmids using any suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also comprise inducible or regulatable promoters for expression of the miR gene products in cancer cells.

The miR gene products that are expressed from recombinant plasmids can be isolated from cultured cell expression systems by standard techniques. The miR gene products that are expressed from recombinant plasmids can also be delivered to, and expressed directly in, the cancer cells.

The miR gene products can be expressed from a separate recombinant plasmid, or they can be expressed from the same recombinant plasmid. In one embodiment, the miR gene products are expressed as RNA precursor molecules from a single plasmid, and the precursor molecules are processed into the functional miR gene product by a suitable processing system, including, but not limited to, processing systems extant within a cancer cell. Other suitable processing systems include, e.g., the in vitro *Drosophila* cell lysate system (e.g., as described in U.S. Published Patent Application No. 2002/0086356 to Tuschl et al., the entire disclosure of which is incorporated herein by reference) and the *E. coli* RNAse III system (e.g., as described in U.S. Published Patent Application No. 2004/0014113 to Yang et al., the entire disclosure of which is incorporated herein by reference).

Selection of plasmids suitable for expressing the miR gene products, methods for inserting nucleic acid sequences into the plasmid to express the gene products, and methods of delivering the recombinant plasmid to the cells of interest are within the skill in the art. See, for example, Zeng et al. (2002), *Molecular Cell* 9:1327-1333; Tuschl (2002), *Nat. Biotechnol,* 20:446-448; Brummelkamp et al. (2002), *Science* 296:550-553; Miyagishi et al. (2002), *Nat. Biotechnol.* 20:497-500; Paddison et al. (2002), *Genes Dev.* 16:948-958; Lee et al. (2002), *Nat. Biotechnol.* 20:500-505; and Paul et al. (2002), *Nat. Biotechnol.* 20:505-508, the entire disclosures of which are incorporated herein by reference.

In one embodiment, a plasmid expressing the miR gene products comprises a sequence encoding a miR precursor RNA under the control of the CMV intermediate-early promoter. As used herein, "under the control" of a promoter means that the nucleic acid sequences encoding the miR gene product are located 3' of the promoter, so that the promoter can initiate transcription of the miR gene product coding sequences.

Vectors

The miR gene products can also be expressed from recombinant viral vectors. It is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in cancer cells.

The recombinant viral vectors of the invention comprise sequences encoding the miR gene products and any suitable promoter for expressing the RNA sequences. Suitable promoters include, but are not limited to, the U6 or H1 RNA pol III promoter sequences, or the cytomegalovirus promoters. Selection of other suitable promoters is within the skill in the art. The recombinant viral vectors of the invention can also comprise inducible or regulatable promoters for expression of the miR gene products in a cancer cell.

Any viral vector capable of accepting the coding sequences for the miR gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

Inhibiting Proliferation

Administration of at least one miR gene product, or at least one compound for inhibiting miR expression, will inhibit the proliferation of cancer cells in a subject. As used herein, to "inhibit the proliferation of a cancer cell" means to kill the cell, or permanently or temporarily arrest or slow the growth of the cell Inhibition of cancer cell proliferation can be inferred if the number of such cells in the subject remains constant or decreases after administration of the miR gene products or miR gene expression-inhibition compounds. An inhibition of cancer cell proliferation can also be inferred if the absolute number of such cells increases, but the rate of tumor growth decreases.

The number of cancer cells in a subject can be measured by immunohistological methods, flow cytometry, or other techniques designed to detect characteristic surface markers of cancer cells.

The miR gene products or miR gene expression-inhibition compounds can be administered to a subject by any means suitable for delivering these compounds to cancer cells of the subject. For example, the miR gene products or miR expression-inhibition compounds can be administered by methods suitable to transfect cells of the subject with these compounds, or with nucleic acids comprising sequences encoding these compounds. In one embodiment, the cells are transfected with a plasmid or viral vector comprising sequences encoding at least one miR gene product or miR gene expression-inhibition compound.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor-mediated nucleic acid delivery, bioballistic or particle acceleration; calcium phosphate precipitation, and transfection mediated by viral vectors.

Administration

A miR gene product or miR gene expression-inhibition compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and direct injection into the tumor.

In the present methods, a miR gene product or miR gene product expression-inhibition compound can be administered to the subject either as naked RNA, in combination with a delivery reagent, or as a nucleic acid (e.g., a recombinant plasmid or viral vector) comprising sequences that express the miR gene product or miR gene product expression-inhibition compound. Suitable delivery reagents include, e.g., the Minis Transit TKO lipophilic reagent; lipofectin; lipofectamine; cellfectin; polycations (e.g., polylysine), and liposomes.

Recombinant plasmids and viral vectors comprising sequences that express the miR gene products or miR gene expression-inhibition compounds, and techniques for delivering such plasmids and vectors to cancer cells, are discussed herein and/or are well known in the art.

In a particular embodiment, liposomes are used to deliver a miR gene product or miR gene expression-inhibition compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. The liposomes for use in the present methods can comprise a ligand molecule that targets the liposome to cancer cells. Ligands that bind to receptors prevalent in cancer cells, such as monoclonal antibodies that bind to tumor cell antigens, are preferred.

Pharmaceutical Compositions

The miR gene products or miR gene expression-inhibition compounds can be formulated as pharmaceutical compositions, sometimes called "medicaments," prior to administering them to a subject, according to techniques known in the art. Accordingly, the invention encompasses pharmaceutical compositions for treating a leukemia. In one embodiment, the pharmaceutical composition comprises at least one isolated miR gene product, or an isolated variant or biologically-active fragment thereof, and a pharmaceutically-acceptable carrier.

In a particular embodiment, the pharmaceutical compositions of the invention comprise at least one miR expression-inhibition compound. In a particular embodiment, the at least one miR gene expression-inhibition compound is specific for a miR gene whose expression is greater in cancer cells than control cells. In certain embodiments, the miR gene expression-inhibition compound is specific for a miR-3151 gene product.

Pharmaceutical compositions of the present invention are characterized as being at least sterile and pyrogen-free. As used herein, "pharmaceutical compositions" include formulations for human and veterinary use. Methods for preparing pharmaceutical compositions of the invention are within the skill in the art, for example as described in Remington's Pharmaceutical Science, 17th ed., Mack Publishing Company, Easton, Pa. (1985), the entire disclosure of which is incorporated herein by reference.

The present pharmaceutical compositions comprise at least one miR gene product or miR gene expression-inhibition compound (or at least one nucleic acid comprising sequences encoding them) (e.g., 0.1 to 90% by weight), or a physiologically-acceptable salt thereof, mixed with a pharmaceutically-acceptable carrier. In certain embodiments, the pharmaceutical compositions of the invention additionally comprise one or more anti-cancer agents (e.g., chemotherapeutic agents). The pharmaceutical formulations of the invention can also comprise at least one miR gene product or miR gene expression-inhibition compound (or at least one nucleic acid comprising sequences encoding them), which are encapsulated by liposomes and a pharmaceutically-acceptable carrier. Especially suitable pharmaceutically-acceptable carriers are water, buffered water, normal saline, 0.4% saline, 0.3% glycine, hyaluronic acid and the like.

In a particular embodiment, the pharmaceutical compositions of the invention comprise at least one miR gene product or miR gene expression-inhibition compound (or at least one nucleic acid comprising sequences encoding them) that is resistant to degradation by nucleases. One skilled in the art can readily synthesize nucleic acids that are nuclease resistant, for example, by incorporating one or more ribonucleotides modified at the 2'-position into the miR gene product. Suitable 2'-modified ribonucleotides include those modified at the 2'-position with fluoro, amino, alkyl, alkoxy, and O-allyl.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one miR gene product or miR gene expression-inhibition compound (or at least one nucleic acid comprising sequences encoding them). A pharmaceutical composition for aerosol (inhalational) administration can comprise 0.01-20% by weight, preferably 1%-10% by weight, of the at least one miR gene product or miR gene expression-inhibition compound (or at least one nucleic acid comprising sequences encoding them) encapsulated in a liposome as described above, and a propellant. A carrier can also be included as desired; e.g., lecithin for intranasal delivery.

The pharmaceutical compositions can further comprise one or more anti-cancer agents. In a particular embodiment, the compositions comprise at least one miR gene product or miR gene expression-inhibition compound (or at least one nucleic acid comprising sequences encoding them) and at least one additional therapeutic agent. In one embodiment the therapeutic agent is a chemotherapeutic agent. In an embodiment the therapeutic agent is a proteasome inhibitor.

Proteasome Inhibitors

Therapeutic agents for use in the methods of the invention include a class of therapeutic agents known as proteasome inhibitors. "Proteasome inhibitor" shall mean any substance which directly or indirectly inhibits the 20S or 26S proteasome or the activity thereof.

The examples described herein entail use of the proteasome inhibitor N-pyrazinecarbonyl-L-phenylalanine-L-leucineboronic acid, bortezomib (Velcade™). The language "proteasome inhibitor" is intended to include bortezomib, compounds which are structurally similar to bortezomib and/or analogs of bortezomib. "Proteasome inhibitor" can also include "mimics". "Mimics" is intended to include compounds which may not be structurally similar to bortezomib but mimic the therapeutic activity of bortezomib or structurally similar compounds in vivo.

Proteasome inhibitors for use in the practice of the invention include additional peptide boronic acids such as those disclosed in Adams et al., U.S. Pat. No. 5,780,454 (1998), U.S. Pat. No. 6,066,730 (2000), U.S. Pat. No. 6,083,903 (2000), U.S. Pat. No. 6,548,668 (2003), and Siman et al. WO 91/13904, each of which is hereby incorporated by reference in its entirety, including all compounds and formulae disclosed therein. Additionally, proteasome inhibitors include peptide aldehyde proteasome inhibitors such as those disclosed in Stein et al. U.S. Pat. No. 5,693,617 (1997), and International patent publications WO 95/24914 published Sep. 21, 1995 and Siman et al. WO 91/13904 published Sep. 19, 1991; Iqbal et al. J. Med. Chem. 38:2276-2277 (1995), as well as Bouget et al. Bioorg Med Chem 17:4881-4889 (2003) each of which is hereby incorporated by reference, including all compounds and formulae disclosed therein. Further, proteasome inhibitors include lactacystin and lactacycstin analogs which have been disclosed in Fentany et al, U.S. Pat. No. 5,756,764 (1998), and U.S. Pat. No. 6,147,223 (2000), Schreiber et al U.S. Pat. No. 6,645,999 (2003), and Fenteany et al. Proc. Natl. Acad. Sci. USA (1994) 91:3358, each of which is hereby incorporated by reference, including all compounds and formulae disclosed therein. Additionally, synthetic peptide vinyl sulfone proteasome inhibitors and epoxyketone proteasome inhibitors have been disclosed and are useful in the methods of the invention. See, e.g., Bogyo et al., Proc. Natl. Acad. Sci. 94:6629 (1997); Spaltenstein et al. Tetrahedron Lett. 37:1343 (1996); Meng L, Proc. Natl. Acad Sci 96: 10403 (1999); and Meng L H, Cancer Res 59: 2798 (1999). Still further, naturally occurring compounds have been recently shown to have proteasome inhibition activity can be used in the present methods. For example, TMC-95A, a cyclic peptide, or Gliotoxin, both fungal metabolites or polyphenols compounds found in green tea have been identified as proteasome inhibitors. See, e.g., Koguchi Y, Antibiot (Tokyo) 53:105. (2000); Kroll M, Chem Biol 6:689 (1999); and Nam S, J. Biol Chem 276: 13322 (2001).

Inhibitors of Leukemias

The invention also encompasses methods of identifying an inhibitor of leukemias comprising providing a test agent to a cell and measuring the level of at least one miR gene product in the cell. In one embodiment, the method comprises providing a test agent to a cell and measuring the level of at least one miR gene product associated with decreased expression levels in cancer cells. A decrease in the level of the miR gene product in the cell after the agent is provided, relative to a suitable control cell (e.g., agent is not provided), is indicative of the test agent being an inhibitor of AML and/or ALL. The agents tested in the methods can be a single agent or a combination of agents. For example, the present methods can be used to determine whether a single chemotherapeutic agent, such as methotrexate, can be used to treat a cancer or whether a combination of two or more agents can be used in combination with a proteasome inhibitor (e.g., bortezomib).

Suitable agents include, but are not limited to drugs (e g., small molecules, peptides), and biological macromolecules (e.g., proteins, nucleic acids). The agent can be produced recombinantly, synthetically, or it may be isolated (i.e., purified) from a natural source. Various methods for providing such agents to a cell (e.g., transfection) are well known in the art, and several of such methods are described hereinabove. Methods for detecting the expression of at least one miR gene product (e.g., Northern blotting, in situ hybridization, RT-PCR, expression profiling) are also well known in the art.

The diagnostic and therapeutic methods described in the Examples can be used as an alternative to or in combination with further treatments. Such treatments may involve chemotherapy, radiation therapy, hormone treatments, bone marrow transplantation, stem cell therapy, induced growth arrest, interferon therapy, and other treatments known in the art. The composition of the invention may further comprise one or more additional compound selected from anti-cancer agents or therapeutics, anti-mitotic agents, apoptotic agents or antibodies, or immune modulators. A composition of embodiments of the invention may be administered alone or in combination with other treatments, therapeutics or agents, either simultaneously or sequentially dependent upon the condition to be treated. In some embodiments, the method includes administration of compositions comprising the one or more specific miR antagonist/antagomir herein described and other agents or therapeutics such as proteasome inhibitors, anti-cancer agents or therapeutics (e.g. cytarabine, daunorubicin, idarubicin, all-trans-retinoic acid (ATRA)), anti-mitotic agents, apoptotic agents or antibodies, or immune modulators. The anti-cancer agents may be tyrosine kinase inhibitors (e.g. imatinib, sunitinib) or phosphorylation cascade inhibitors, post-translational modulators, cell growth or division inhibitors (e.g. anti-mitotics), inhibitors or signal transduction inhibitors. Other treatments or therapeutics may include the administration of suitable doses of pain relief drugs such as non-steroidal anti-inflammatory drugs (e.g. aspirin, acetaminophen, ibuprofen, or ketoprofen) or opiates such as morphine, or anti-emetics. In addition, the composition may be administered with immune modulators, such as interleukins, tumor necrosis factor (TNF) or other growth factors, colony stimulating factors, cytokines or hormones such as dexamethasone which stimulate the immune response and reduction or elimination of cancer cells or tumors. The composition may also be administered with anti-tumor antigen antibodies.

Methods for Analyzing

It will be appreciated that diagnostic, prognostic, and therapeutic methods described herein can be performed in conjunction with an analysis of other non-genetic factors known to be associated with a subject's likely response to an agent. Such factors include epidemiological risk factors associated with poor response or resistance to an agent. These risk factors can be used to augment an analysis of one or more polymorphisms as herein described when assessing a subject's response to an agent.

As described herein, the effect of more than one responsive or restrictive polymorphisms can be combined to more accurately predict or determine a subject's response to an agent, or their suitability to a treatment regime.

Also described herein are methods for predicting or determining a subject's response to an agent, and to methods for determining a subject's suitability to a treatment regime or intervention. The methods comprise the analysis of polymorphism/s herein shown to be associated with responsiveness to an agent, or the analysis of results obtained from such an analysis. The use of polymorphisms herein shown to be associated with responsiveness to an agent in the assessment of a subject's suitability to a treatment regime or intervention are also provided, as are nucleotide probes and primers, kits, and microarrays suitable for such assessment. Methods of treating subjects having the polymorphisms herein described are also provided. Methods for screening for compounds able to modulate the expression of genes associated with the polymorphisms herein described are also provided.

In addition to identifying responsive or unresponsive subjects, it is possible to segment a population to define a subgroup of the population that is suitable to undergo an intervention. Such an intervention may be a diagnostic intervention, such as imaging test, other screening or diagnostic test (e.g., biochemical or RNA based test), or may be a therapeutic intervention, such as a chemopreventive or chemotherapeutic therapy, or a preventive lifestyle modification (such as stopping smoking or increasing exercise).

In defining such a clinical threshold, people can be prioritized to a particular intervention in such a way to minimize costs or minimize risks of that intervention (for example, the costs of image-based screening or expensive preventive treatment or risk from drug side-effects or risk from radiation exposure).

In determining this threshold, one might aim to maximize the ability of the test to detect the majority of cases (maximize sensitivity) but also to minimize the number of people at low risk that require, or may be are otherwise eligible for, the intervention of interest.

Accordingly, there is also provided herein a method of assessing a subject's suitability for an intervention diagnostic of or therapeutic for AML, the method comprising: a) providing the result of one or more genetic tests of a sample from the subject, and b) analyzing the result for the presence or absence of one or more responsive polymorphisms or for the presence or absence of one or more resistance polymorphisms, or one or more polymorphisms which are in linkage disequilibrium with any one or more of the polymorphisms; wherein the presence of one or more responsive polymorphisms is indicative of the subject's suitability for the intervention, and wherein the absence of one or more responsive polymorphisms or the presence of one or more resistance polymorphisms is indicative of the subject's unsuitability for the intervention. The results of tests and risk factors may be communicated to patients, specialists, and care providers.

The intervention may be a diagnostic test for the disease, such as a blood test for AML. In certain embodiments, a method for analyzing includes the steps of: a) analyzing a sample from a subject with a SNP detection assay to determine that the subject has at least one polymorphism in the BAALC gene, thereby generating a genetic analysis result; b) inputting the genetic analysis result into a system, wherein the system comprises: i) a computer processor for receiving, processing, and communicating data, ii) a storage component for storing data which contains a reference genetic database of results of at least one genetic analysis with respect to response to an agent, and iii) a computer program, embedded within the computer processor, which is configured to process the genetic analysis result in the context of the reference database to determine, as an outcome, that the subject will be responsive to the agent; c) processing the genetic analysis result with the computer program in the context of the reference database to determine, as an outcome, that the subject is responsive to the agent; d) communicating the outcome from the computer program; and e) modulating therapy being administering to the subject.

The implementation of the methods in computer systems and programs as described herein, the data produced by such methods, and the use of such data in the prediction or determination of a subject's response to an agent, or in the determination of a subject's suitability or unsuitability for an intervention diagnostic or therapeutic of a disease or condition associated with AML are also contemplated.

As used herein, the phrase "assessing a subject's suitability for an intervention" or grammatical equivalents thereof means one or more determinations of whether a given subject is or should be a candidate for an intervention or is not or should not be a candidate for an intervention.

As used herein the term "intervention" includes medical tests, analyses, and treatments, including diagnostic, therapeutic and preventative treatments, and psychological or psychiatric tests, analyses and treatments, including counseling and the like.

Computer-Related Embodiments

It will also be appreciated that the methods described herein are amenable to use with and the results analyzed by computer systems, software and processes. Computer systems, software and processes to identify and analyze genetic polymorphisms are well known in the art. Similarly, implementation of the algorithm utilized to generate a SNP score as described herein in computer systems, software and processes is also contemplated. For example, the results of one or more genetic analyses as described herein may be analyzed using a computer system and processed by such a system utilizing a computer-executable example of the analyses described herein.

Both the SNPs and the results of an analysis of the SNPs may be "provided" in a variety of mediums to facilitate use thereof. As used in this section, "provided" refers to a manufacture, other than an isolated nucleic acid molecule, that contains SNP information. Such a manufacture provides the SNP information in a form that allows a skilled artisan to examine the manufacture using means not directly applicable to examining the SNPs or a subset thereof as they exist in nature or in purified form. The SNP information that may be provided in such a form includes any of the SNP information provided herein such as, for example, polymorphic nucleic acid and/or amino acid sequence information, information about observed SNP alleles, alternative codons, populations, allele frequencies, SNP types, and/or affected proteins, identification as a responsive SNP or a resistance SNP, weightings (for example for use in an combined analysis as described herein), or any other information provided.

In one application of this embodiment, the SNPs and the results of an analysis of the SNPs utilized can be recorded on a computer readable medium. As used herein, "computer readable medium" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable media can be used to create a manufacture comprising computer readable medium having recorded thereon SNP information.

As used herein, "recorded" refers to a process for storing information on computer readable medium. A skilled artisan can readily adopt any of the presently known methods for recording information on computer readable medium to generate manufactures comprising the SNP information.

A variety of data storage structures are available to a skilled artisan for creating a computer readable medium having recorded thereon SNP information. The choice of the data storage structure will generally be based on the means chosen to access the stored information. In addition, a variety of data processor programs and formats can be used to store the SNP information on computer readable medium. For example, sequence information can be represented in a word processing text file, formatted in commercially-available software such as WordPerfect and Microsoft Word, represented in the form of an ASCII file, or stored in a database application, such as OB2, Sybase, Oracle, or the like. A skilled artisan can readily adapt any number of data processor structuring formats (e.g., text file or database) in order to obtain computer readable medium having recorded thereon the SNP information.

By providing the SNPs and/or the results of an analysis of the SNPs utilized in computer readable form, a skilled artisan can routinely access the SNP information for a variety of purposes. Computer software is publicly available which allows a skilled artisan to access sequence information provided in a computer readable medium. Examples of publicly available computer software include BLAST (Altschul et at, J. Mol. Biol. 215:403-410 (1990)) and BLAZE (Brutlag et at, Comp. Chem. 17:203-207 (1993)) search algorithms.

Also provided herein are systems, particularly computer-based systems, which contain the SNP information described herein. Such systems may be designed to store and/or analyze information on, for example, a number of SNP positions, or information on SNP genotypes from a number of subjects. The SNP information represents a valuable information source. The SNP information stored/analyzed in a computer-based system may be used for such applications as predicting a subject's likely responsiveness to an agent, in addition to computer-intensive applications as determining or analyzing SNP allele frequencies in a population, mapping disease genes, genotype-phenotype association studies, grouping SNPs into haplotypes, correlating SNP haplotypes with response to particular drugs, or for various other bioinformatic, pharmacogenomic, drug development, or human identification/forensic applications.

As used herein, "a computer-based system" refers to the hardware, software, and data storage used to analyze the SNP information. The minimum hardware of the computer-based systems can include a central processing unit (CPU), an input, an output, and data storage. A skilled artisan can readily appreciate that any one of the currently available computer-based systems are suitable for use. Such a system can be changed into a system by utilizing the SNP information without any experimentation.

As used herein, "data storage" refers to memory which can store SNP information, or a memory access facility which can access manufactures having recorded thereon the SNP information.

The one or more programs or algorithms are implemented on the computer-based system to identify or analyze the SNP information stored within the data storage. For example, such programs or algorithms can be used to determine which nucleotide is present at a particular SNP position in a target sequence, to analyze the results of a genetic analysis of the SNPs described herein, or to derive a SNP score as described herein. As used herein, a "target sequence" can be any DNA sequence containing the SNP position(s) to be analyzed, searched or queried.

A variety of structural formats for the input and output can be used to input and output the information in the computer-based systems. An exemplary format for an output is a display that depicts the SNP information, such as the presence or absence of specified nucleotides (alleles) at particular SNP positions of interest. Such presentation can provide a rapid, binary scoring system for many SNPs or subjects simultaneously. It will be appreciated that such output may be accessed remotely, for example over a LAN or the internet. For example, given the nature of SNP information, such remote accessing of such output or of the computer system itself is available only to verified users so that the security of the SNP information and/or the computer system is maintained Methods to control access to computer systems and the data residing thereon are well-known in the art, and are amenable to the embodiments described herein.

Accordingly, there is provided herein a system for determining a subject's response to an agent, the system comprising: computer processor means for receiving, processing and communicating data; storage means for storing data including a reference genetic database of the results of at least one genetic analysis with respect to response to an agent or with respect to a disease or condition associated with AML, and optionally a reference non-genetic database of non-genetic risk factors for a disease or condition associated with AML; and, a computer program embedded within the computer processor which, once data consisting of or including the result of a genetic analysis for which data is included in the reference genetic database is received, processes the data in the context of the reference databases to determine, as an outcome, the subject's response to an agent, the outcome being communicable once known, preferably to a user having input the data.

The manner of therapeutic intervention or treatment will be predicated by the nature of the polymorphism/s and the biological effect of the polymorphism/s. For example, where a resistance polymorphism is associated with a change in the expression of a gene, intervention or treatment may be directed to the restoration of normal expression of the gene, by, for example, administration of an agent capable of modulating the expression of the gene. Where a polymorphism is associated with decreased expression of a gene, therapy can involve administration of an agent capable of increasing the expression of the gene, and conversely, where a polymorphism is associated with increased expression of a gene, therapy can involve administration of an agent capable of decreasing the expression of the gene.

For example, in situations where a polymorphism is associated with upregulated expression of a gene, therapy utilizing, for example, RNAi or antisense methodologies can be implemented to decrease the abundance of mRNA and so decrease the expression of the gene. Alternatively, therapy can involve methods directed to, for example, modulating the activity of the product of the gene, thereby compensating for the abnormal expression of the gene.

Where a resistance polymorphism is associated with decreased gene product function or decreased levels of expression of a gene product, therapeutic intervention or treatment can involve augmenting or replacing of the function, or supplementing the amount of gene product within the subject for example, by administration of the gene product or a functional analogue thereof. For example, where a polymorphism is associated with decreased enzyme function, therapy can involve administration of active enzyme or an enzyme analogue to the subject. Similarly, where a polymorphism is associated with increased gene product function, therapeutic intervention or treatment can involve reduction of the function, for example, by administration of an inhibitor of the gene product or an agent capable of decreasing the level of the gene product in the subject. For example, where a SNP allele or genotype is associated with increased enzyme function, therapy can involve administration of an enzyme inhibitor to the subject.

Likewise, when a responsive polymorphism is associated with upregulation of a particular gene or expression of an enzyme or other protein, therapies can be directed to mimic such upregulation or expression in a subject lacking the resistive genotype, and/or delivery of such enzyme or other protein to such subject.

Further, when a responsive polymorphism is associated with downregulation of a particular gene, or with diminished or eliminated expression of an enzyme or other protein, desirable therapies can be directed to mimicking such conditions in a subject that lacks the responsive genotype.

The method can further include transmitting the report to a patient or to a medical practitioner.

Design of Therapeutic Agents

The relationship between the various polymorphisms identified and the responsiveness of a subject to an agent, or susceptibility (or otherwise) of a subject to a disease or condition associated with AML also has application in the design and/or screening of candidate therapeutics. This is particularly the case where the association between a resistance polymorphism is manifested by either an upregulation or downregulation of expression of a gene. In such instances, the effect of a candidate therapeutic on such upregulation or downregulation is readily detectable.

Similarly, where the polymorphism is one which when present results in a physiologically active concentration of an expressed gene product outside of the normal range for a subject (adjusted for age and sex), and where there is an available prophylactic or therapeutic approach to restoring levels of that expressed gene product to within the normal range, subject subjects can be screened to determine the likelihood of their benefiting from that restorative approach. Such screening involves detecting the presence or absence of the polymorphism in the subject by any of the methods described herein, with those subjects in which the polymorphism is present being identified as subjects likely to benefit from treatment.

Kits

Also provided herein are kits useful for screening nucleic acid isolated from one or more subjects for allelic variation of any one of the mitochondrial transcription factor genes, and in particular for any of the SNPs described herein, wherein the kits may comprise at least one oligonucleotide selectively hybridizing to a nucleic acid comprising any one of the one or more of which are SNPs described herein and instructions for using the oligonucleotide to detect variation in the nucleotide corresponding to the SNP of the isolated nucleic acid.

Also provided is a diagnostic kit for detecting one or more polymorphisms in a genetic sample from a human subject refractory to statin treatment, further comprising a polymerase chain reaction (PCR) primer set for amplifying nucleic acid fragments corresponding to the at least one probe. In non-limiting examples, the probe has a label capable of being detected, the label is detected by electrical, fluorescent or radioactive means, the probe is selected from the group of sense, anti-sense, and naturally occurring mutants, of the at least one probe; and/or, the probe is affixed to a substrate.

The kit can comprise one or more of the following: at least one primer and/or probe for determining a single polymorphism in a chromosomal copy of the gene, wherein the polymorphism is associated with the AML; at least one primer and/or probe for determining a single polymorphism in two chromosomal copies of the gene, wherein the polymorphism is associated with AML; a combination of primers and/or probes for determining a combination of polymorphisms in a chromosomal copy of the gene, wherein the combination of polymorphisms is associated with AML; a combination of primers and/or probes for determining a combination of polymorphisms in two chromosomal copies of the gene, wherein the combination of polymorphisms is associated with AML; and/or, an enzyme for primer elongation, nucleotides and/or labeling groups. In certain embodiments, diagnostic kit further comprises computer software to analyze information of a hybridization of the at least one probe in the diagnostic kit.

One embodiment provides an oligonucleotide that specifically hybridizes to the isolated nucleic acid molecule, and wherein the oligonucleotide hybridizes to a portion of the isolated nucleic acid molecule comprising any one of the polymorphic sites in the BAALC gene.

Suitable kits include various reagents for use in suitable containers and packaging materials, including tubes, vials, and shrink-wrapped and blow-molded packages. Materials suitable for inclusion in an exemplary kit comprise one or more of the following: gene specific PCR primer pairs (oligonucleotides) that anneal to DNA or cDNA sequence domains that flank the genetic polymorphism/s of interest, reagents capable of amplifying a specific sequence domain in either genomic DNA or cDNA without the requirement of performing PCR; reagents required to discriminate between the various possible alleles in the sequence domains amplified by PCR or non-PCR amplification (e.g., restriction endonucleases, oligonucleotide that anneal preferentially to one allele of the polymorphism, including those modified to contain enzymes or fluorescent chemical groups that amplify the signal from the oligonucleotide and make discrimination of alleles more robust); reagents required to physically separate products derived from the various alleles (e.g. agarose or polyacrylamide and a buffer to be used in electrophoresis, HPLC columns, SSCP gels, formamide gels or a matrix support for MALDI-TOF).

The specific methods described herein are representative of various embodiments or preferred embodiments and are exemplary only and not intended as limitations on the scope of the invention. Other objects, aspects, examples and embodiments will occur to those skilled in the art upon consideration of this specification, and are encompassed within the spirit of the invention as defined by the scope of the claims. It will be readily apparent to one skilled in the art that varying substitutions and modifications can be made to the invention disclosed herein without departing from the scope and spirit of the invention.

The invention will now be illustrated by the following non-limiting examples.

EXAMPLES

Certain embodiments of the present invention are defined in the Examples herein. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Diagnostic Methods

Example 1

The BAALC gene is located on chromosome 8q22.3. miR-3151 is embedded in intron 1 of BAALC. As described herein, miR-3151 is co-expressed with BAALC and contributes to poor prognostic impact in older CN-AML.

Methods

Patients, Treatment, and Cytogenetic Studies

One-hundred-seventy-nine patients aged 60 years or more with de novo CN-AML, who were treated with intensive cytarabine/daunorubicin-based regimens on Cancer and Leukemia Group B (CALGB) front-line clinical protocols were included. All protocols received IRB approval at the participating institutions. Cytogenetic analyses were performed on pretreatment bone marrow (BM) samples by CALGB-approved institutional cytogenetic laboratories as part of CALGB 8461, a prospective cytogenetic companion study. The diagnosis of normal cytogenetics was based on the analysis of ≥20 BM metaphase cells and confirmed by central karyotype review. All patients gave informed consent for the research use of their specimens, in accordance with the Declaration of Helsinki.

Molecular Analyses

Pretreatment peripheral blood (PB) samples were analyzed for miR-3151 and BAALC expression levels by real-time reverse transcription polymerase chain reaction (RT-PCR). The TaqMan assays were carried out for each sample in triplicate using Taqman Primer-Probe sets for BAALC and miR-3151 and the respective house-keeping genes 18S and RNU44 (Life Technologies Corporation/Applied Biosystems, Carlsbad, Calif.) according to protocol instructions.

Additional molecular markers were analyzed centrally in pretreatment BM or PB samples and included: FLT3-ITD,29 FLT3 tyrosine kinase domain mutations (FLT3-TKD), partial tandem duplication of the myeloid/lymphoid or mixed-lineage leukemia (trithorax homolog, Drosophila) gene (MLL-PTD), mutations in the NPM1, CEBPA, tet methylcytosine dioxygenase 2 (TET2), additional sex combs like 1 (Drosophila) (ASXL1), DNA (cytosine-5-)-methyltransferase 3 alpha (DNMT3A), 8 runt-related transcription factor 1 (RUNX1), Wilms tumor 1 (WT1), and isocitrate dehydrogenase 1 (NADP+), soluble (IDH1) and isocitrate dehydrogenase 2 (NADP+), mitochondrial (IDH2)4 genes, and expression levels of the v-ets erythroblastosis virus E26 oncogene homolog (avian) (ERG) and meningioma (disrupted in balanced translocation) 1 (MN1) genes.

Gene-expression profiling (GEP) and microRNA-expression profiling (MEP) Gene-expression of samples was profiled using the Affymetrix U133 plus 2.0 array (Affymetrix, Santa Clara, Calif.) and microRNA expression was profiled using The Ohio State University custom microRNA array (OSU_CCC version 4.0).

Validation of FBXL20 and USP40 as Direct miR-3151 Targets

For stable expression of miR-3151, the miR-3151 stem-loop was cloned into a lentiviral expression vector, using lentiviral miR-scramble as the respective control for all experiments. To analyze the effects of forced miR-3151 expression on the predicted target genes, the expression of FBXL20 and USP40 on mRNA levels was assessed and compared to the effects of cells infected with scramble control using Real-Time PCR. Western Blotting to test the effects of miR-3151 on protein level was performed. The 3'-untranslated regions (UTRs) of FBXL20 and USP40 were cloned into a luciferase reporter vector (wild-type vs mutated miR-3151 binding sequence, see FIG. 10) and luciferase activity was assessed.

Definition of Clinical Endpoints and Statistical Analysis

The prognostic impact on clinical outcome was evaluated in older CN-AML patients of miR-3151 expression alone and in combination with its host gene BAALC. Median expression levels of miR-3151 and BAALC were used to define low and high miR-3151 and BAALC expressers, respectively, for all analyses.

Definitions of clinical endpoints (i.e., complete remission [CR], disease-free [DFS] and overall survival [OS]) and details of statistical analyses, including variable selection for statistical modeling, are provided in the Example 2 below.

Associations between patients with low and high expression of miR-3151 for baseline demographic, clinical, and molecular features were compared using the Fisher's exact and Wilcoxon rank-sum tests for categorical and continuous variables, respectively. Estimated probabilities of DFS and OS were calculated using the Kaplan-Meier method, and the log-rank test evaluated differences between survival distributions. Multivariable logistic regression models were constructed to analyze factors related to the probability of achieving CR using a limited backward selection procedure. Multivariable proportional hazards models were constructed for DFS and OS to evaluate the impact of miR-3151 expression by adjusting for other variables using a limited backward selection procedure. For achievement of CR, estimated odds ratios (OR), and for survival endpoints, hazard ratios (HR) with their corresponding 95% confidence intervals were obtained for each significant prognostic factor.

For the GEP and MEP, summary measures of gene and microRNA expression, respectively, were computed, normalized, and filtered (see Example 2). The profiles were derived by comparing gene expression between low and high miR-3151 expressers. Univariable significance levels of 0.001 for GEP (0.005 for MEP) were used to determine the probe sets (probes) that comprised the signatures.

Results

Associations of miR-3151 expression with clinical and molecular characteristics Patients with high miR-3151 expression had lower percentages of circulating blasts (P=0.02), and were more likely to be NPM1 wild-type (P<0.001), belong to the European LeukemiaNet (ELN) Intermediate-I Genetic Group11 and harbor mutations of RUNX1 (P<0.001) than low expressers (P=0.05; FIG. 6).

Also, high miR-3151 expression was associated with high expression levels of its host gene BAALC (P<0.001) and MN1 (P=0.05). About two thirds of the patients had a concordant expresser status for miR-3151 and BAALC expression levels, while one third of the patients exhibited upregulation of only one of the two markers.

Prognostic Value of miR-3151 Expression in CN-AML

Patients with high miR-3151 expression had a lower CR rate (P=0.005, 62% vs 81%) compared with low expressers. With a median follow-up time for living patients of 5.1 years (range: 4.1-11.6), high miR-3151 expressers had a shorter DFS (P=0.003, HR=1.76; FIG. 1A).

Figure 1B:
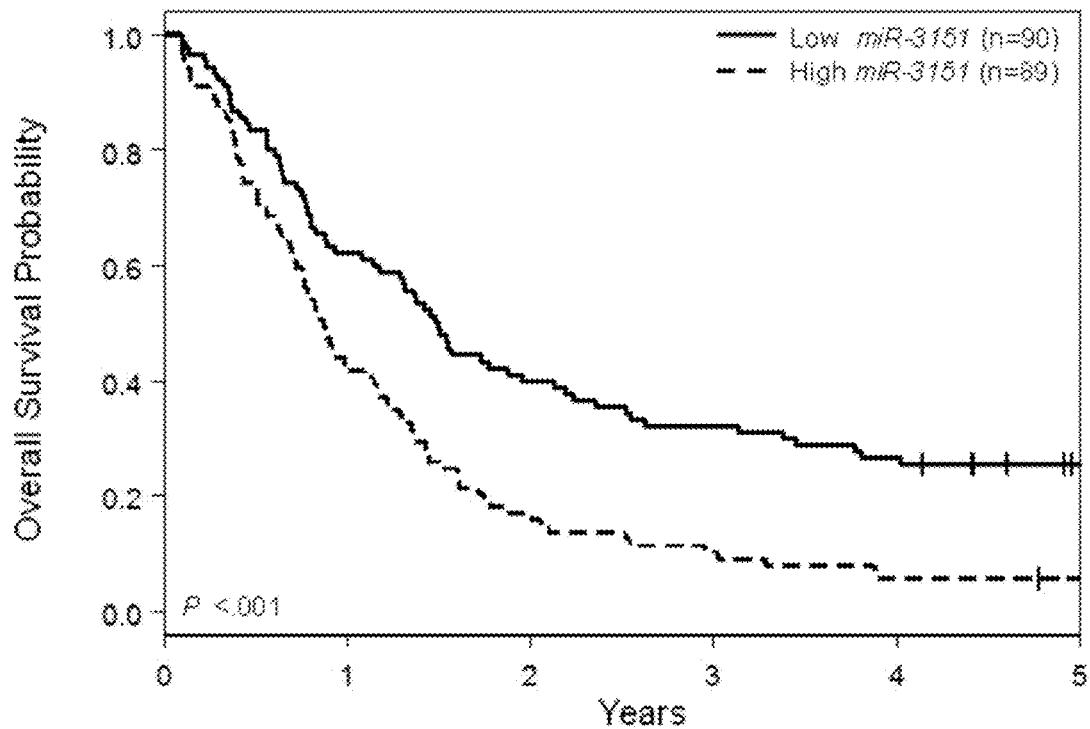

At 3 years after CR achievement, only 7% of high miR-3151-expressing patients were disease-free compared with 26% of low expressers. High miR-3151 expressers also had a shorter OS (P<0.001, HR=1.86; FIG. 1B). Three years after diagnosis, 10% of high miR-3151 expressers were still alive compared with 32% of low expressers.

Since miR-3151 expression levels were associated with the expression levels of its host gene BAALC, we analyzed the impact on outcome endpoints of both genes using bi-variable models. Analyses showed that high expression levels of either marker had significant adverse impact on CR (miR-3151: P<0.001, OR=0.47; BAALC: P<0.001, OR=0.3), DFS (miR-3151: P=0.01, HR=1.68; BAALC: P=0.003, HR=1.82) and OS (miR3151: P=0.002, HR=1.68; BAALC: P<0.001, HR=2.01). Thus both miR-3151 and BAALC independently added information for determination of all outcome endpoints (FIG. 8).

Despite the strong association of miR-3151 and BAALC expression levels, approximately one third of patients were discordant in expresser status of the two markers (FIG. 6).

Figure 2A:
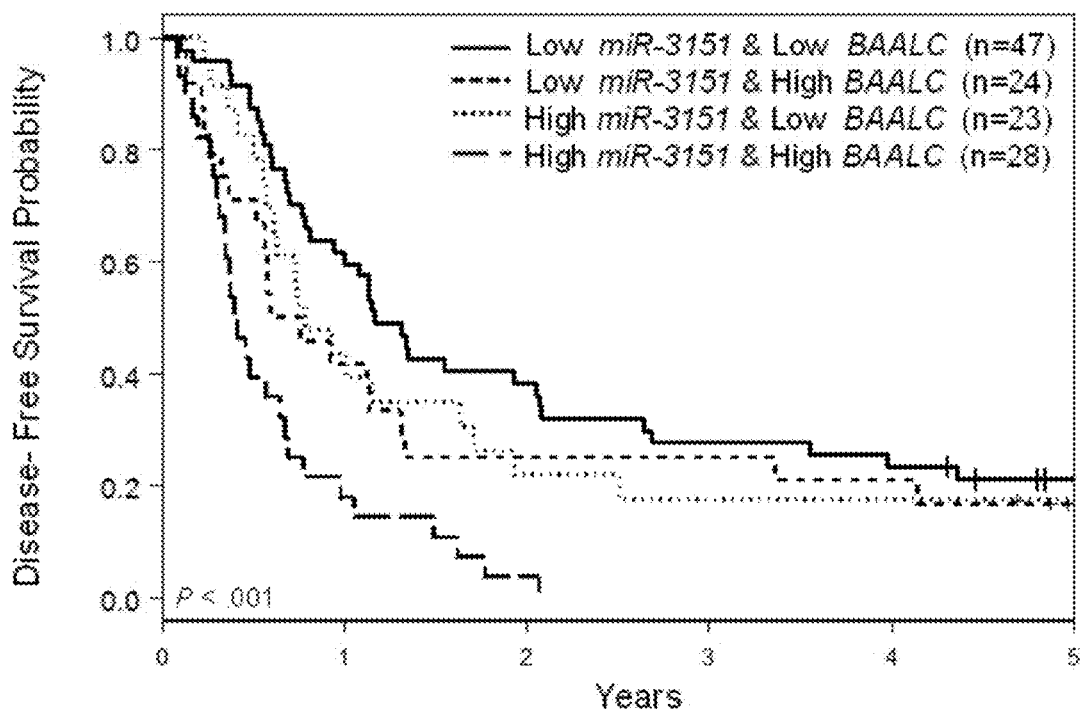
FIG. 2A-FIG. 2B. Outcome of CN-AML patients aged 60 years of age or older with respect to miR-3151 and BAALC expression.
Figure 2B:
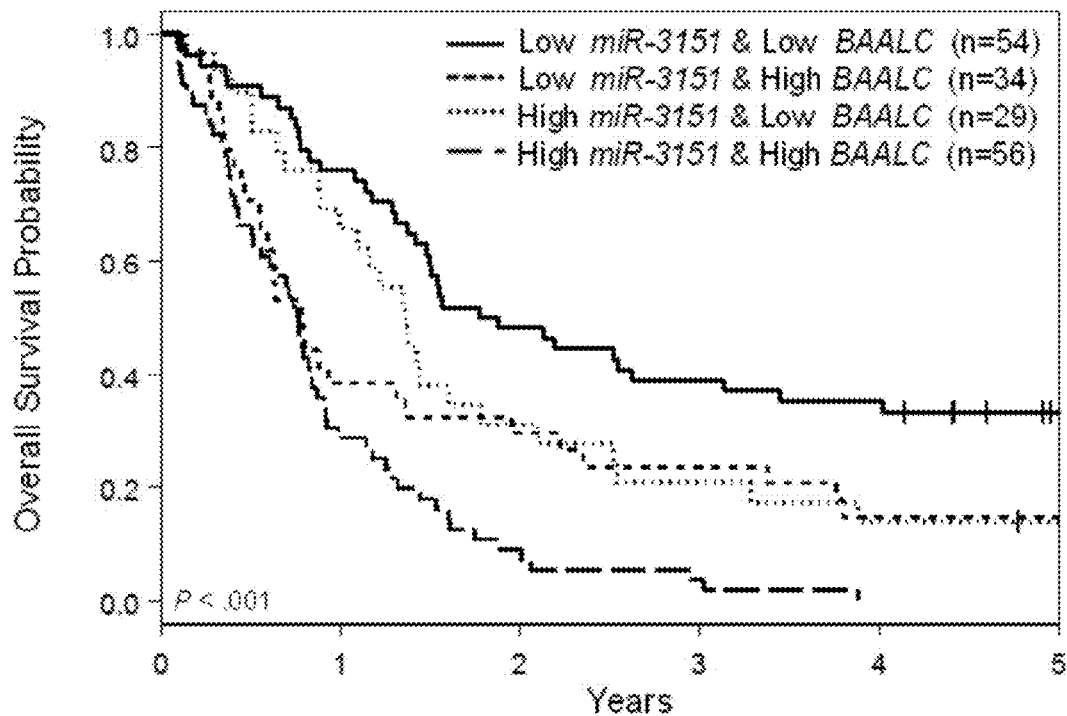

Consequently, the inventors next investigated whether their combination (miR-3151/BAALC: high/high, high/low, low/high, low/low) would reveal differences in impact on outcome endpoints. Patients who had high expression of both miR-3151 and BAALC demonstrated the lowest CR rates (50%), whereas patients that highly expressed only one of the two markers had intermediate CR rates (low miR-3151/high BAALC: 71%; high miR-3151/low BAALC: 79%), and low expressers of both markers had the highest CR rate (87%, P<0.001). Patients with high expression of both miR-3151 and BAALC had significantly shorter DFS and OS than those expressing both markers at low levels (P<0.001 for both DFS and OS; FIG. 2A and FIG. 2B) or those who exhibited high expression of only one of the markers (DFS: P=0.03, OS: P=0.01). Of patients who expressed both the miR and its host gene at high levels, only one survived longer than three years after diagnosis.

In multivariable analyses (FIG. 7), after adjustment for BAALC expression status and white blood count (WBC), patients with high miR-3151 expression had a trend towards a lower CR rate (P=0.13, OR=0.56). High miR-3151 expressers had shorter DFS (P<0.001, HR=2.38), after adjustment for FLT3-TKD, and ERG expression status, and shorter OS (P=0.009, HR=1.69), after adjustment for DNMT3A R882 mutations and ERG and BAALC expression status.

miR-3151 Expression in the Context of ELN Genetic Groups

The ELN Genetic Groups are associated with outcome in older CN-AML patients. The addition of selected new molecular markers can further improve prognostication within the ELN Genetic Groups. The inventors then determined whether miR-3151 expression levels can improve outcome prediction within those ELN Genetic Groups that include CN-AML. Within the ELN Favorable Genetic Group, there were no differences in outcome between high and low miR-3151-expressing patients.

Figure 3A:
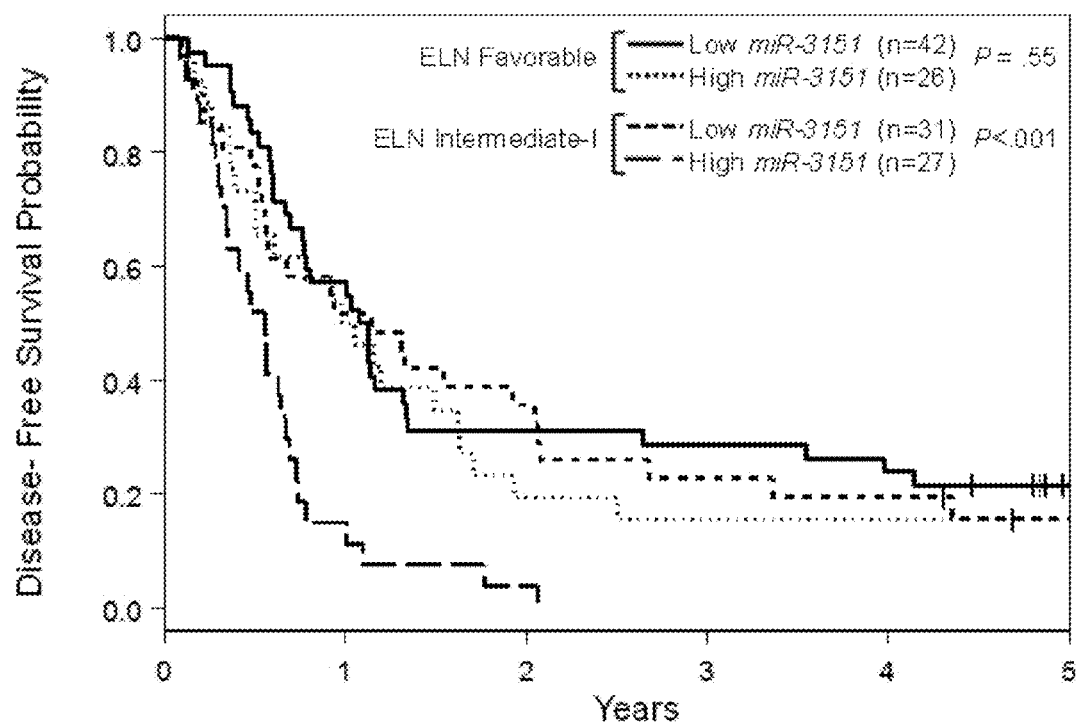
FIG. 3A-FIG. 3B. Outcome of CN-AML patients aged 60 years of age or older with respect to miR-3151 expression and ELN Genetic Group.
Figure 3B:
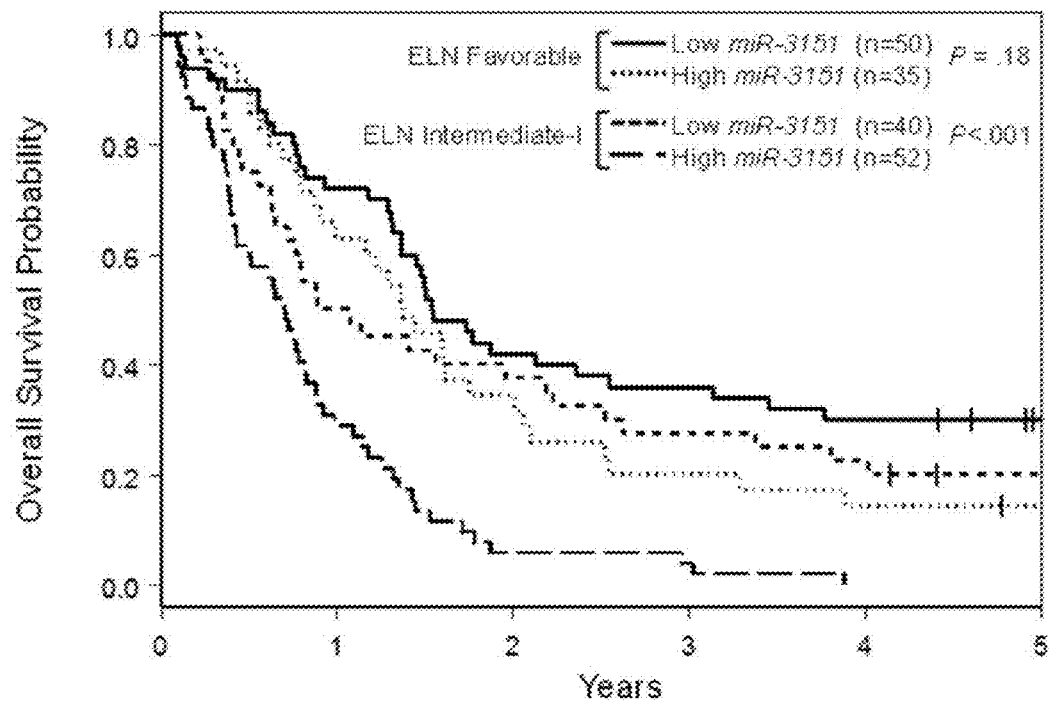

However, in the ELN Intermediate-I Genetic Group, high miR-3151 expression levels identified patients with particularly poor prognosis for all three outcome endpoints. Only 52% of high miR-3151 expressers in this ELN Group achieved a CR, compared with 78% of low miR-3151 expressers (P<0.001). Likewise, patients with high miR-3151 expression levels had significantly shorter DFS (<0.001; FIG. 3A) and OS (P<0.001; FIG. 3B) compared with low miR-3151 expressers. For all three endpoints, the outcome of the low miR-3151 expressers classified in the ELN Intermediate-I group was similar to that of both high and low miR-3151-expressing patients in the ELN Favorable Genetic Group (FIG. 3A, FIG. 3B, and FIG. 9).

Biologic Insights

Figure 4A:
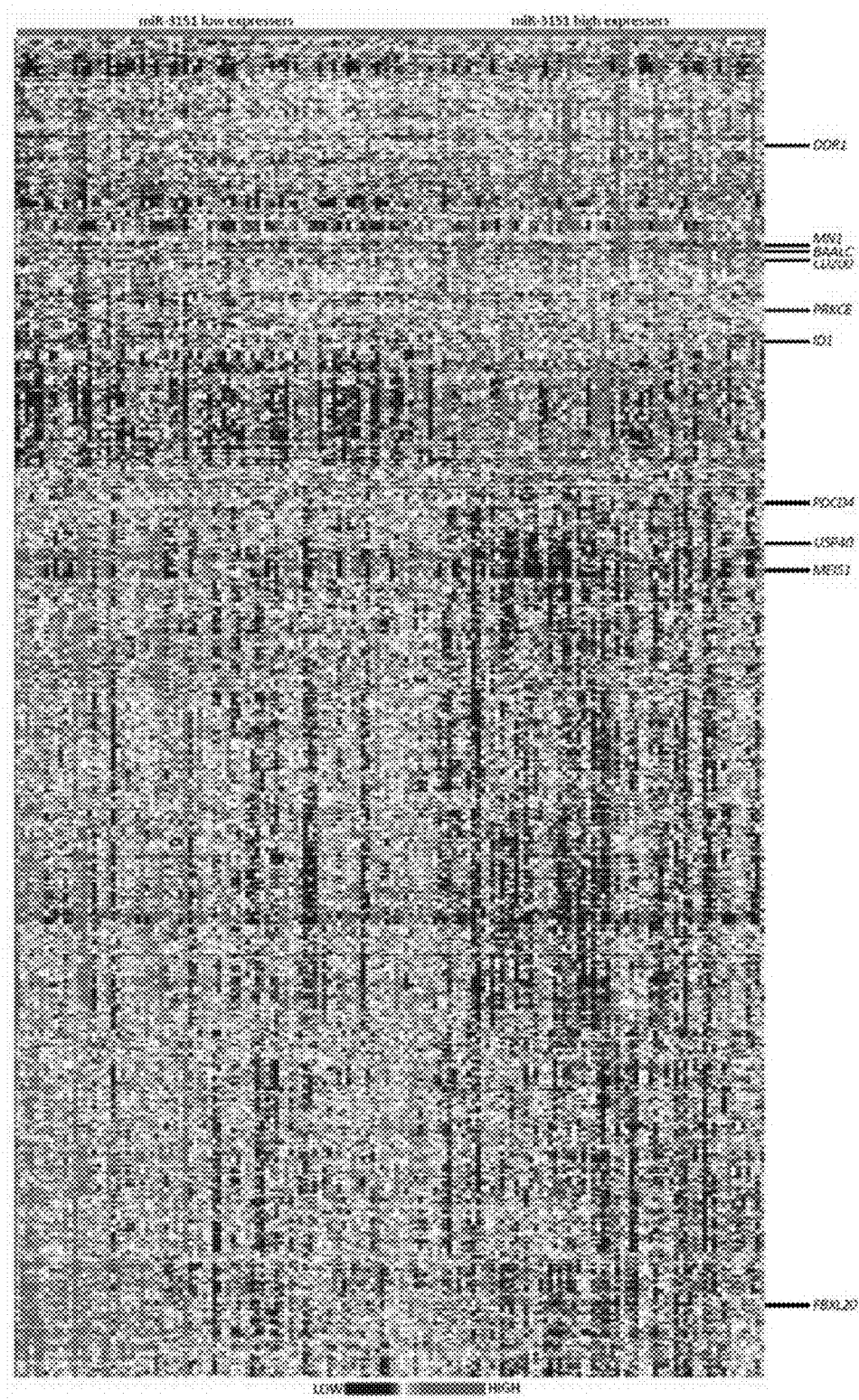
FIG. 4A-FIG. 4B. Heat map of the derived gene- and microRNA expression signature associated with miR-3151 expression in CN-AML patients 60 years of age or older. Expression values of the probe-sets (probes) are represented by color, with blue indicating expression less than and red indicating expression greater than the median value for the given probe-set (probe).

To gain biologic insights into miR-3151-associated leukemia, a gene-expression signature comparing high versus low miR-3151 expressers was derived. High miR-3151 expresser status was associated with the differential expression of 597 probe sets, representing 374 annotated genes. Of these, 192 probe sets (116 annotated genes) were upregulated and 405 probe sets (258 annotated genes) were downregulated (FIG. 4A, FIG. 11, and FIG. 12).

High miR-3151 expressers exhibited upregulation of genes previously associated with worse outcome in CN-AML, including the transcriptional co-regulator MN1,34 the dominant negative helix-loop-helix protein ID1,37 the miR-3151 host BAALC and the surface marker CD200. Additionally, the inventors observed upregulation of genes encoding several kinases, such as DDR1, is important for cell growth and differentiation by activation of NOTCH1, and PRKCE, which is involved in apoptosis and several cellular signaling pathways.

Among the most downregulated genes in high miR-3151 expressers was the HOX co-factor MEIS1, which is a key regulator in developmental processes and whose absence causes disturbances in the colony-forming ability of hematopoietic stem cells, and the tumor suppressor PDCD4, which contributes to retinoic acid-induced granulocytic differentiation. Furthermore, downregulation of 23 genes encoding different zinc finger proteins (ZNFs), which are involved in transcriptional regulation, was found in high miR-3151 expressers. Of the 258 downregulated genes, 73 were in-silico predicted targets of miR-3151 (FIG. 12).

Pathway analysis of the miR-3151-associated-expression signature showed an enrichment of genes involved in transcriptional regulation, post-translational modification, cell cycle control, cellular development, and cancer pathways, showing evidence of an impact of miR-3151 on basic regulatory functions (FIG. 13).

Figure 4B:
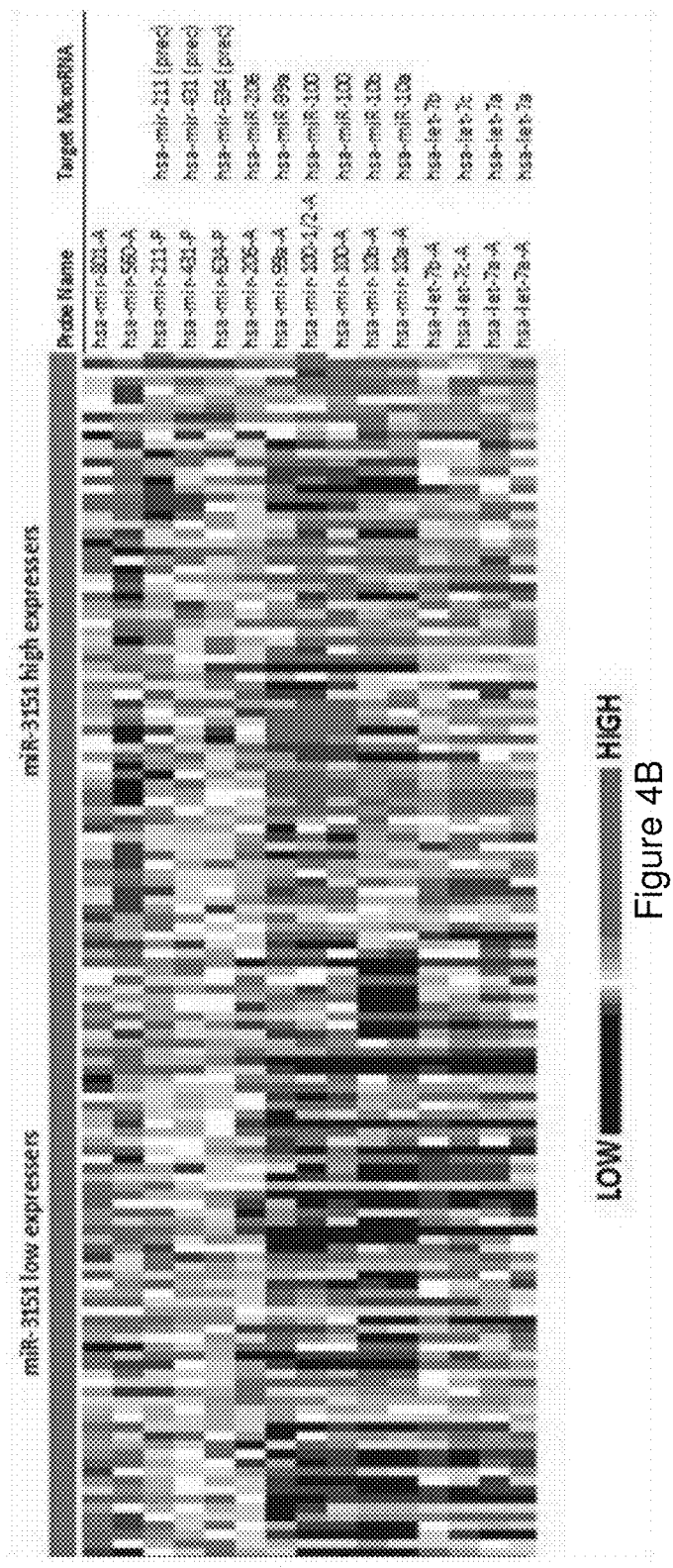

To determine the networking processes of known miRs in which miR-3151 might be involved, the inventors derived microRNA-expression signatures associated with miR-3151 expresser status (FIG. 4B).

Fifteen (15) differentially expressed probes were discovered, representing 14 miRs, 5 upregulated and 9 downregulated in high compared with low miR-3151 expressers.

Among the downregulated miRs were let-7a, let-7b and let-7c, which suppress tumorigenesis by being crucial actors in many cell proliferation pathways and whose downregulation is associated with AML leukemogenesis.

Also observed was the downregulation of miR-10a and miR-10b, which are microRNAs embedded in HOX gene clusters, and miR-99a and miR-100, whose reduced expression has been implicated in tumor progression of cervical and prostate cancer.

To determine the downstream effects of high miR-3151 expression, the inventors validated one or two of the downregulated genes in the miR-3151-associated gene expression signature as direct targets of miR-3151. For identification of potential candidate genes, the inventors searched among the in-silico predicted targets for probe-sets of annotated genes which showed at least a 25% downregulation with a P-value <0.0001. Only six of the 73 genes fulfilled these criteria (see FIG. 12, highlighted in grey).

Among these, the inventors selected as candidates those function is associated with the pathways shown to be preferentially involved (FIG. 13).

Strikingly, two of the six genes, the F-box and leucine-rich repeat protein 20 (FBXL20) and the ubiquitin-specific protease 40 (USP40), are involved in the ubiquitination pathway, showing an impact of miR-3151 on this important post-translational regulatory process. FBXL20 is a member of the F-box gene family. As a part of the SCF (Skp, Cullin, F-box containing) ubiquitin ligase complex it is responsible for the ubiquitination of proteins, thereby labeling them for consecutive proteasomal degradation. USP40 belongs to the family of cysteine proteases that function as deubiquitinating enzymes.

Figure 5A:
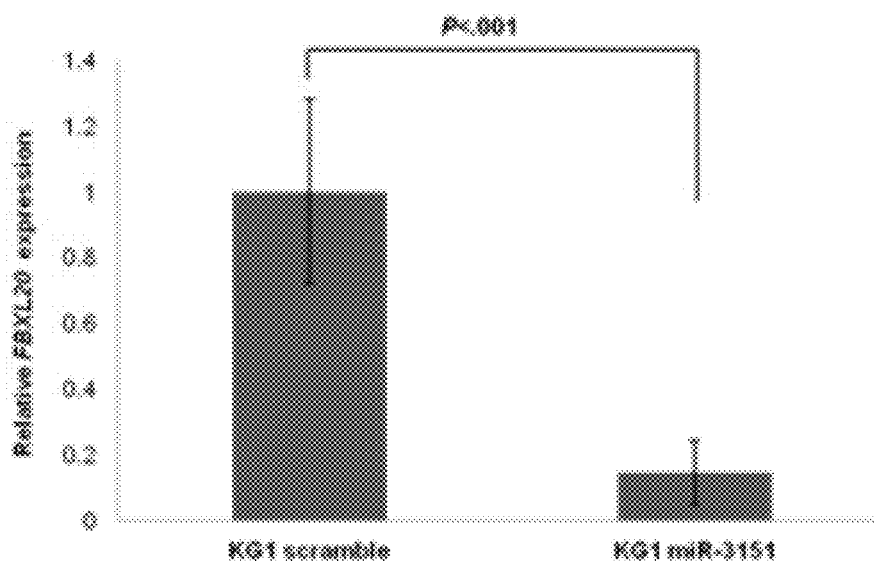
FIG. 5A-FIG. 5F. Validation of FBXL20 and USP40 as direct targets of miR-3151. Expression levels of FBXL20 and USP40 as determined by RT-PCR in KG1 cells infected in triplicate with miR-3151 compared relative to scramble control are shown. Forced miR-3151 expression resulted in an 85% decrease of FBXL20 (±standard deviation [s.d.], FIG. 5A) and a 66% decrease of USP40 expression levels (±s.d., FIG. 5B, both P<0.001; expression levels are displayed relative to scramble control).
Figure 5B:
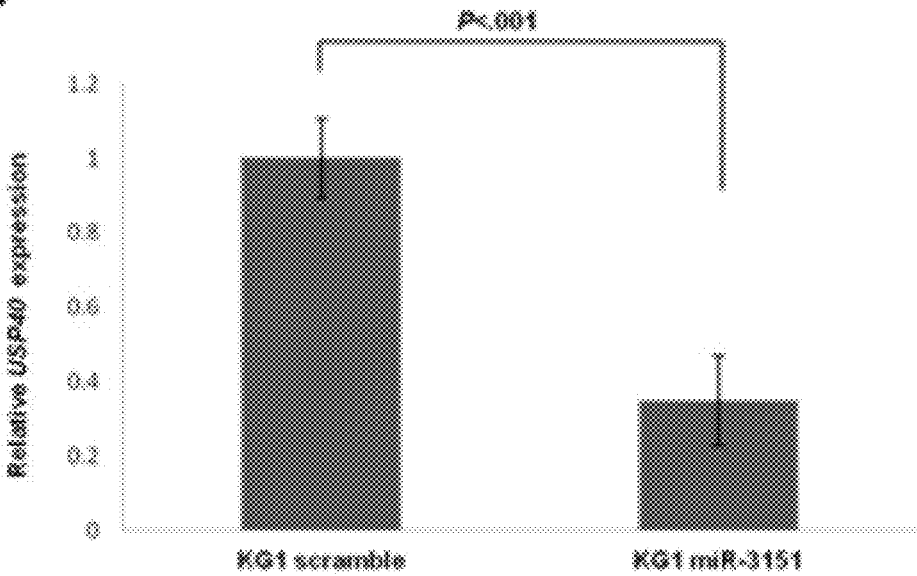
Figure 5C:
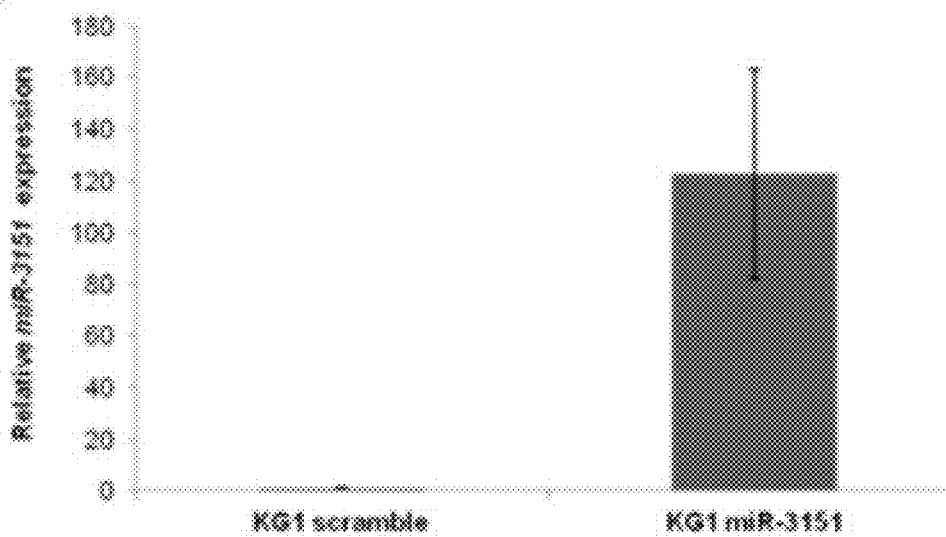
Figure 5D:
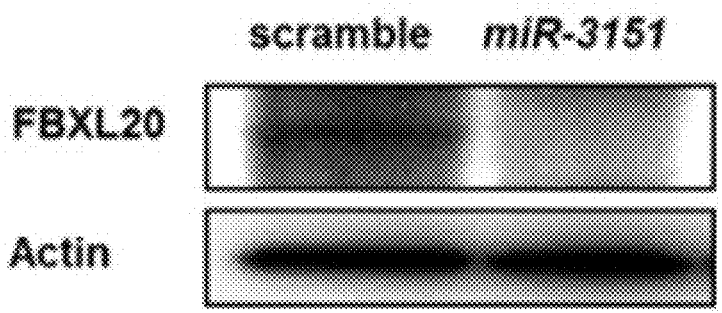
Figure 5E:
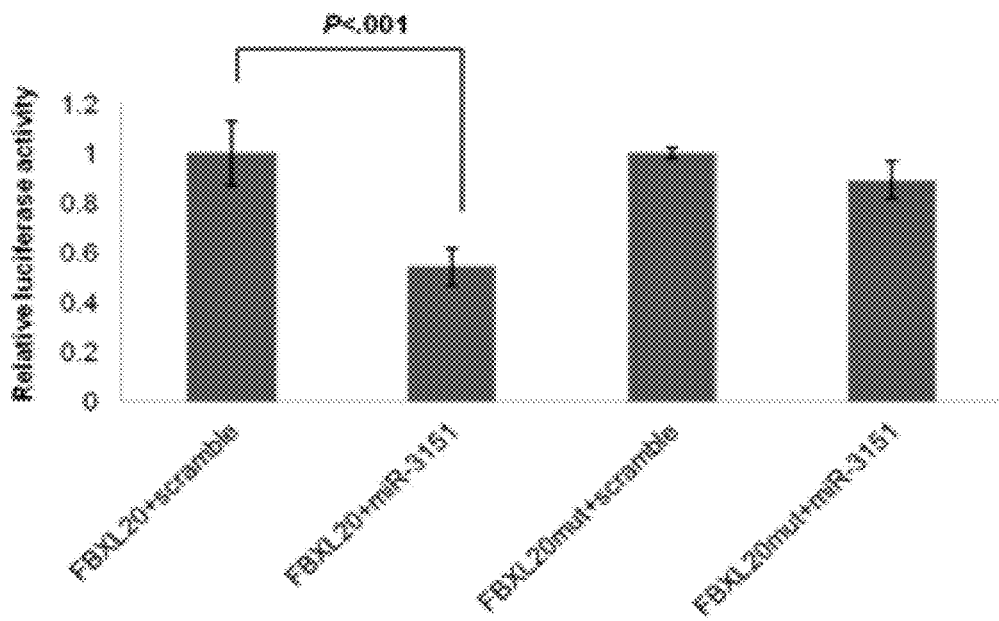
Figure 5F:
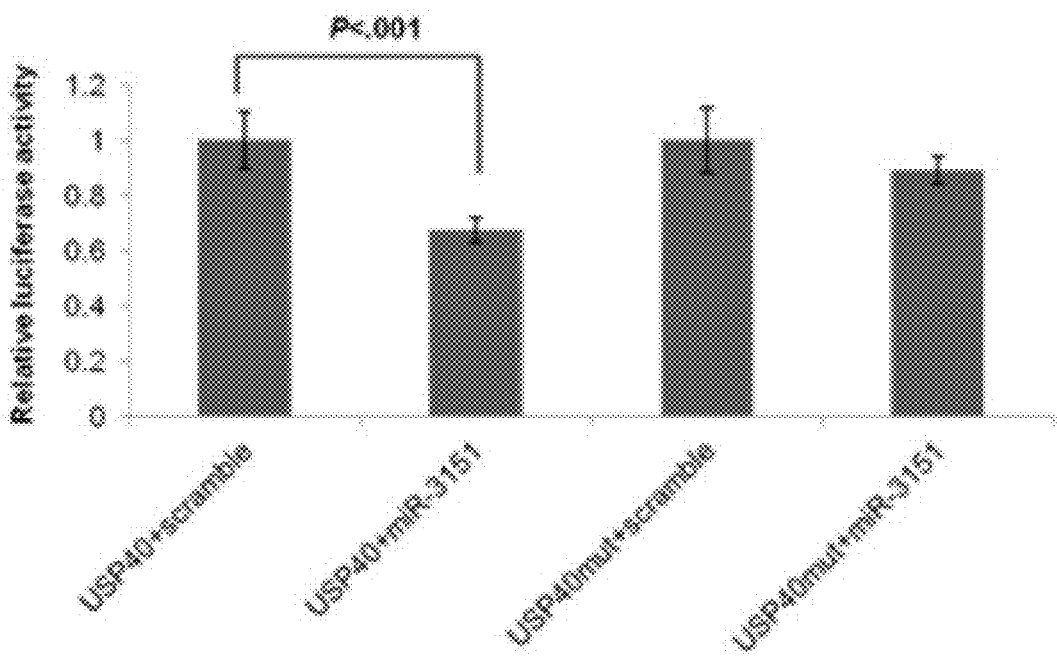

To validate FBXL20 and USP40 as direct targets of miR-3151, the inventors stably overexpressed miR-3151 in KG1 cells using a lentiviral system. Forced expression of miR-3151 resulted in significant downregulation of the FBXL20 and USP40 transcripts (FBXL20: 85% decrease, FIG. 5A; USP40: 66% decrease, FIG. 5B, both $P<0.001$) compared to scramble control.

miR-3151 also downregulated FBXL20 on the protein level (FIG. 5D). However, none of the USP40 antibodies showed a band at the predicted protein size of 140 kD. To demonstrate that FBXL20 and USP40 are direct targets of miR-3151, the respective 3-UTRs of both genes with the sequence containing the predicted miR-3151 binding sites were cloned into luciferase reporter vectors. The luciferase assays demonstrated a 54% and 33% decrease in luciferase activity for the FBXL20 and USP40 constructs, respectively, after addition of miR-3151 compared to scramble control (FIG. 5E and FIG. 5F). The observed downregulations were abrogated after mutation of the seed sequence of the predicted miR-3151 binding sites (FIG. 5E and FIG. 5F). These results demonstrate that FBXL20 and USP40 are direct targets of miR-3151.

Discussion of Example 1

The intronic miR-3151 is as an independent prognostic factor for outcome of older CN-AML patients. Furthermore, miR-3151 acts in concert with its host gene, the established molecular prognostic marker BAALC. The data show that both markers are independently contributing to poor outcome of CN-AML patients.

The inventors discovered that similarly to BAALC, higher expression levels of miR-3151 were associated with poor prognosis. However the hosted miR and the hosting gene have an independent clinical significance and impacted differently on specific outcome endpoints. Whereas miR-3151 expression did not remain an independent predictor in the multivariable model for achievement of CR, BAALC expression remained a strong prognostic factor for CR. This is consistent with the inventors' findings that CR rate is an outcome endpoint strongly affected by aberrant BAALC expression levels. On the other hand, high miR-3151 expression and not BAALC expression was a strong predictor of DFS. Further, both miR-3151 and BAALC expression levels remained important prognostic factors for OS.

Patients overexpressing both miR-3151 and its host gene BAALC had particularly poor outcome for all three outcome endpoints. In contrast, patients exhibiting upregulation of only one of the two markers had a significantly better outcome; their DFS was comparable to that of low miR-3151/low BAALC-expressing patients whereas their OS was intermediate in comparison with OS of both groups of patients who had concordant miR-3151 and BAALC expresser status. These findings show that miR-3151 and BAALC are independently impacting on outcome, thereby possibly creating a synergism to support leukemogenesis.

By deriving a GEP signature comparing high and low miR-3151-expressing patients, the inventors herein now show the biology and the downstream effects of miR-3151 in CN-AML patients. High miR-3151-expressing patients also had upregulation of genes that are prognosticators of worse outcome in AML patients, such as MN1, ID1 and CD200 and the miR-3151 host gene BAALC. Among the downregulated genes associated with high miR-3151 expression, the inventors discovered that several genes implicated in hematopoietic differentiation, including MEIS1, whose absence has been shown to interfere with the normal development of hematopoietic precursors. Also, downregulation of multiple genes encoding ZNF proteins was seen, showing a role of miR-3151 in pre-transcriptional regulation.

Interestingly, pathway analysis of the miR-3151-associated gene-expression signature shows an involvement of miR-3151 in general regulatory processes on both the transcriptional and post-translational level. Identification of direct target genes of miR-3151 belonging to these pathways can be used to pinpoint a root cause for the downstream effects including the pathophysiological consequences seen in high miR-3151-expressing CN-AML patients. For example, the inventors herein were able to validate FBXL20 and USP40 as direct targets of miR-3151. Both genes are involved in the ubiquitination pathway which is known to be important for cell cycle control, cell growth, and a multitude of transcriptional and posttranscriptional regulatory processes. Even though FBXL20 and USP40 are likely only the first of several important miR-3151 targets, their involvement may initiate and direct future research into the understanding of miR-3151's function The miR-3151-associated GEP signature shared some features with a GEP signature associated with BAALC expression in older CN-AML patients, in which we also reported an upregulation of MN1 and CD200 and downregulation of MEIS1. However, changes in expression of other genes were unique to the GEP signature associated with miR-3151 (e.g., upregulation of ID1 and downregulation of ZNFs). Moreover, key components of the BAALC signature (e.g., upregulation of CD34 and PROM1 and downregulation of several HOX gene clusters) were not found in the inventors' miR-3151-associated signature, thus showing important differences in biologic activities of miR-3151 and BAALC.

Regarding the derived MEP signature, the inventors herein identified 14 miRs differentially expressed between high and low miR-3151 expressers. Among these miRs, a key component was downregulation of members of the let-7 family, which are known tumor suppressors and whose downregulation is found in various types of cancer, linking the let-7 family members to the HMGA2 and RAS pathways.

Comparing the derived MEP signature with the signature described to be associated with BAALC expression, the inventors herein discovered interesting similarities but also differences. High BAALC-expressing patients exhibited downregulation of miR-99, miR-100 and let-7b, whereas downregulation of let-7a and let-7c seemed to be uniquely associated with high miR-3151 expression levels. Downregulation of miR-9 was only observed in the signature associated with high BAALC expression levels. Of note, no upregulated microRNA was shared by both MEP signatures.

The fact that we were able to identify miR-3151 as the second microRNA after miR-181a that independently impacts on outcome of CN-AML patients provides further support to the importance of aberrantly expressed microRNAs as prognostic factors in CN-AML. It is noteworthy that miR-3151 is not only a new molecular marker, is now shown herein as an example of how known factors (here BAALC) in AML leukemogenesis may be supported by microRNAs located in the locus itself. In the case of the BAALC gene this finding is of special interest since the gene's function and therefore the reasons for its strong prognostic impact in CN-AML patients are unknown.

Thus, Example 1 shows that high expression of miR-3151 is an independent prognostic factor associated with poor outcome in older CN-AML patients. The partly discordant expresser status of miR-3151 and its host gene BAALC, the independent impact of the two genes on outcome, and the fact that patients overexpressing both miR-3151 and its host have significantly worse outcomes than those exhibiting upregulation of only one of the genes thus show that the two genes contribute to the aggressiveness of the disease through different mechanisms.

Thus, determining the expression levels of miR-3151 at diagnosis is useful to improve the risk-stratification of older CN-AML. Development of therapies targeting miR-3151 upregulation with synthetic inhibitors also provides more effective strategies for personalized treatment of older CN-AML patients.

Example 2

Treatment Protocols

Patients were treated on one of the following intensive cytarabine/daunorubicin-based Cancer and Leukemia Group B (CALGB) frontline treatment protocols: 8525 (n=18), 8923 (n=10), 9420 (n=5), 9720 (n=89), or 10201 (n=57). The analyzed patient subset (n=179) performed similarly to comparable de novo CN-AML patients which have not been included in our dataset [n=151; complete remission (CR): P=0.31, diseasefree survival (DFS): P=0.40, overall survival (OS): P=0.99].

Among these protocols, CALGB 9420, 9720, and 10201 included investigational agents other than chemotherapy. CALGB 9720 was initiated as a phase III trial in untreated acute myeloid leukemia (AML) patients 60 years and older evaluating multidrug resistance (MDR) modulation by valspodar (PSC-833) during induction and consolidation therapy with cytarabine, daunorubicin, and etoposide. The valspodar (PSC-833) arm was closed after randomized assignment of 120 patients because of excessive early deaths. Enrollment on this protocol continued on the chemotherapy-only control arm. CALGB 10201 evaluated the BCL2 antisense, oblimersen sodium (Genasense; G3139) administered with induction and consolidation chemotherapy; preliminary results showed no impact of the antisense on outcome. CALGB 9420 and CALGB 9720 evaluated a subcutaneous IL-2 regimen in older AML patients as maintenance therapy, which was demonstrated to induce no clear benefit. Per the protocols, patients enrolled on these studies did not receive stem cell transplantation in first CR.

Sample Preparation and miR-3151 and BAALC Expression Analyses

Patients enrolled on the aforementioned treatment protocols were also enrolled on the companion protocols CALGB 9665 (Leukemia Tissue Bank) and CALGB 20202 (molecular studies in AML), and gave informed consent for pretreatment marrow and blood collection and their research use in accordance with the Declaration of Helsinki Mononuclear cells from pretreatment blood were enriched by Ficoll-Hypaque gradient and cryopreserved in liquid nitrogen until they were thawed at 37° C. for analysis. DNA and total RNA sample extraction and quality control were performed. Briefly, total RNA was extracted using the Trizol method and complementary DNA was synthesized from total RNA using the MicroRNA Reverse Transcription Kit (Invitrogen, Carlsbad, Calif.) and SuperScript®III (Invitrogen, Carlsbad, Calif.) respectively according to protocol instructions. Custom made RT-PCR primers for miR-3151 were obtained from ABI (Life Technologies Corporation/Applied Biosystems, Carlsbad, Calif.). The TaqMan assays were carried out for each sample in triplicate using Taqman Primer-Probe sets for BAALC and miR-3151 and the respective house-keeping genes 18S and RNU44 (Life Technologies Corporation/Applied Biosystems, Carlsbad, Calif.) according to protocol instructions. To determine the relative levels of expression of miR-3151 and BAALC, the comparative $C_T$ method was used (Life Technologies Corporation/Applied Biosystems, Carlsbad, Calif.). First, the parameter threshold cycle ($C_T$) was determined for miR-3151 and RNU44 as well as for BAALC and 18S, and the cycle number difference (RNU44-miR-3151 and 18S-BAALC=$\Delta C_T$ significance level of 0.001 was used to determine the probe-sets that comprised the signature. A global test of significance based on a permutation procedure was performed to determine whether or not the number of differentially expressed probe sets was more than expected by chance; if not, no signature is reported for the comparison.

MicroRNA Expression Profiling (MEP)

For MEP total RNA was extracted from pretreatment BM or blood mononuclear cells of 135 patients with material available. MicroRNA expression was profiled using The Ohio State University custom microRNA array (OSU_CCC version 4.0). For expression profiling, signal intensities were calculated for each spot, with an adjustment made for local background. Spots that were flagged due to low signal-to-noise ratio on more than 75% of arrays were excluded from analysis. Signal intensities were log-transformed and quantile normalization was performed on arrays using spots for all human and mouse microRNA probes represented on the array. Log-signal intensities from replicate spots (i.e., spots representing the same probe) were averaged. For each microRNA probe, an adjustment was made for batch effects (i.e., differences in expression related to the batch in which arrays were hybridized). Further analysis was limited to 460 unique human probes that passed the filtering criterion. An expression signature was derived by comparing microRNA expression between low and high miR-3151 expressers. A univariable significance level of <0.005 was used to determine the probes that comprised the signature. A global test of significance based on a permutation procedure was performed to determine whether or not the number of differentially expressed probes was more than expected by chance; if not, no signature is reported for the comparison.

Stable Expression of miR-3151

The stemloop of miR-3151 with 200 bp flanking sequence was cloned into the HIV based lentiviral dual promoter vector (pCDH-CMV-MCS-EF1-copGFP+Puro cDNA; System Biosciences, Mountain View, Calif.). As a control, lentiviral scramble control miR was used according to the manufacturer's instructions (miRZiP000, System Biosciences). 4500 µg lentiviral construct was transfected into 293TN cells using 45 µg pPACKH1 and 55 µl PureFrection (System Biosciences). After 48 h and 72 h, the supernatant containing the pseudoviral particles was collected and the virus was precipitated overnight at 4° C. using 7.5 ml PEG-IT virus precipitation solution (System Biosciences). 200 µl Phosphate Buffered Saline and 25 µM Hepes Buffer were used for resuspension of the pelleted virus. 200,000 KG1 cells/ml were infected in triplicate with 20 IU virus, using 5 µl Transdux Infection Reagent (System Biosciences). Ten days later successfully infected cells were selected using Puromycin. To check for successful overexpression of miR-3151, RNA (1 million cells) was harvested on day 14 and reverse transcribed to cDNA using the TaqMan MicroRNA Reverse Transcription Kit (Life Technologies Corporation/Applied Biosystems, Carlsbad, Calif.). To analyze the effect of forced miR-3151 expression on the predicted target genes, the inventors used the Superscript III First-Strand cDNA Synthesis Kit (Life Technologies Corporation/Invitrogen). Both kits were used according to the manufacturer's instructions. Simultaneously, protein (from 4 million cells) was harvested and used for Western Blotting.

Western Blot Analysis

Western blotting was performed using the protein lysates, mixed with (6×) sodium dodecyl sulfate (SDS) loading buffer (125 mM Tris pH 6.8, 4% SDS, 20% glycerol, 200 mM beta-mercaptoethanol, 0.2% [w/v] bromophenol blue) and boiled for 10 minutes. Protein samples were loaded onto a 4-20% Criterion Tris-HCl precast gel (Bio-Rad, Herkules, Calif.) and transferred to 0.45 µm polyvinylidene fluoride (PVDF) membrane. Membranes were blocked using 5% milk and incubated in primary antibody overnight at 4° C. on a rocking platform. Membranes were washed in Tris-Buffered Saline (TBS) buffer containing 0.1% Tween-20 and probed with secondary antibody for 2 h. Following a final wash in TBS buffer containing Tween-20, membranes were incubated in ECL Western blotting detection reagents (GE Healthcare, Piscataway, N.J.) and exposed to film (Denville Scientific, Metuchen, N.J.). Antibodies used were: Actin (sc-1616, 1:1000), FBL20 (sc-242799, 1:200; Santa Cruz Biotechnologies, Santa Cruz, Calif.) and anti-goat HRP-linked.

Luciferase Reporter Assays

To assess the inhibiting potential of miR-3151 on FBXL20 and USP40 gene expression, 500 bp of the respective 3-untranslated regions (UTR) containing the predicted miR-3151 binding sites were cloned into a luciferase reporter vector (pGL4.24; Promega Corporation, Madison, Wis.). Mutation of the predicted binding sites was accomplished using bi-directional mutation primers, exchanging 3 nucleotides of the respective predicted binding sequences. Primer sequences and the corresponding annealing temperatures are listed in FIG. 10.

HEK 293T cells (American Type Culture Collection ATCC, Manassas, Va.) were cultured in DMEM culture medium supplemented with 10% Fetal Bovine Serum, L-glutamine (200 mM), and antibiotic/antimycotic agent (all Life Technologies Corporation/Gibco, Carlsbad, Calif.) and grown at 37° C. with 5% $CO_2$. When the culture reached 80% confluency, the cells were transfected in triplicate with reporter and control constructs (Renilla, pGL4.74; Promega Corporation,) using Lipofectamin 2000 transfection reagent (Life Technologies Corporation/Invitrogen). Cells were co-transfected with 10 pmol of either MIR-3151 (Pre-miR miRNA Precursor, Life Technologies Corporation/Ambion) or scramble control-miR (negative Control Pre-miR #1, Ambion). Transfected cells were incubated for 24 h at 37° C. with 5% $CO_2$ in Opti-MEM II medium containing the Lipofectamine/plasmid combination. Protein lysates were assessed for firefly luciferase and Renilla luciferase activities according to the recommendations detailed in the Dual-Luciferase Reporter Assay System (Promega Corporation). For further analysis, relative expression was normalized using co-transfected Renilla luciferase.

Statistical Analyses

Patients were divided into quartile groups—based on expression levels of miR-3151 and assessed for outcome associations by the trend test for DFS (P=0.03) and OS (P=0.001); based on these results a median cut was used in all statistical analyses. A median cut for BAALC was used in all statistical analyses. For analysis of the ERG expression data, complete case analysis was used to handle missing expression data of the patients.

Definition of Clinical Endpoints

CR was defined as recovery of morphologically normal BM and blood counts (i.e., neutrophils ≥1,500/μl and platelets >100,000/μl), and no circulating leukemic blasts or evidence of extramedullary leukemia. DFS was measured from the date of CR until date of relapse or death, regardless of cause. OS was measured from the date on study until date of death. Patients alive at last follow-up were censored for both DFS and OS.

Multivariable Models

Variables in addition to miR-3151 expression that were considered for univariable analyses for DFS and OS were age, sex, race, hemoglobin, platelet count, WBC, NPM1 (mutated vs wild-type), FLT3-ITD (present vs absent), FLT3-TKD (present vs absent), CEBPA (mutated vs wild-type), ELN Genetic Group (Favorable vs Intermediate-I), TET2 (mutated vs wild-type), ASXL1 (mutated vs wild-type), DNMT3A (mutated vs wild-type), RUNX1 (mutated vs wild-type), MLL-PTD (present vs absent), IDH1 (mutated vs wild-type), IDH2 (mutated vs wild-type), WT1 (mutated vs wild-type) and BAALC and ERG expression (high vs low). Variables considered for inclusion in the logistic models were those significant at $\alpha=0.20$ from the univariable models. Variables remaining in the final models were significant at $\alpha=0.05$.

Variables in addition to miR-3151 expression that were considered for univariable analyses for DFS and OS were age, sex, race, hemoglobin, platelet count, WBC, NPM1 (mutated vs wild-type), FLT3-ITD (present vs absent), FLT3-TKD (present vs absent), CEBPA (mutated vs wild-type), ELN Genetic Group (Favorable vs Intermediate-I), TET2 (mutated vs wild-type), ASXL1 (mutated vs wild-type), DNMT3A (mutated vs wild-type), RUNX1 (mutated vs wild-type), MLL-PTD (present vs absent), IDH1 (mutated vs wildtype), IDH2 (mutated vs wild-type), WT1 (mutated vs wild-type) and BAALC and ERG expression (high vs low). Variables significant at $\alpha=0.20$ from the univariable analyses were considered for multivariable analyses. The proportional hazards assumption was checked for each variable individually. If the proportional hazards assumption was not met for a particular variable, then an artificial time dependent covariate was included in all models that contained that variable.

Therapeutic Methods

Example 3

Intronic miR-3151 and its Host Gene BAALC Support Oncogenesis by Deregulating TP53

Overexpression of the intronic microRNA miR-3151 and its host gene BAALC associate with poor prognosis in acute myeloid leukemia patients. The mechanisms are not fully understood. As described herein, miR-3151 directly down-regulates TP53 while BAALC increases JUN expression, contributing to reduced apoptosis and increased leukemogenesis, respectively in vitro and in vivo. Additionally, as described, both genes are independently regulated by a SP1/NF-κB-transactivating complex and BAALC expression is further affected by RUNX1. The aberrant activation of miR-3151 and BAALC can be reduced by treatment with the proteasome inhibitor bortezomib, providing a useful treatment option for high miR-3151 and BAALC expressing AML patients.

Described herein is the oncogenic potential of the embedded intronic microRNA, miR-3151, and its oncogene host, BAALC. By identifying TP53 as a direct target of miR-3151 and JUN as a downstream effector of BAALC, an interplay of two oncogenes is elucidated, which leads to deregulation of the TP53-associated apoptosis pathway, resulting in increased leukemogenesis in vitro and in vivo. Also shown is how oncogenes may be supported by microRNAs inside the genes themselves. Furthermore, characterization of these upstream regulators potentially provides treatment options for leukemia patients with deregulated miR-3151/BAALC and ultimately TP53 expression levels.

Deregulation of miR-3151 is evident in malignancies including: Acute lymphoblastic leukemia (ALL), Chronic lymphocytic leukemia (CLL), Acute myelogenous leukemia (AML), Chronic myelogenous leukemia (CML), malignant melanoma, neuroblastoma, multiple myeloma (MM), and thyroid cancer.

Deregulation of miR-3151 in human malignancies includes both upregulation, for example in AML, and down-regulation, for example in papillary thyroid carcinoma.

Intronic miR-3151 directly targets TP53 and deregulates the TP53 apoptosis pathway.

The miR-3151 host gene BAALC increases JUN expression, thereby directly and indirectly leading to deregulation of TP53.

Overexpression of miR-3151, alone and in combination with its host gene, leads to increased leukemogenesis in mice.

Both miR-3151 and BAALC are independently regulated by a SP1/NF-κB transactivating complex.

Upregulated miR-3151 and BAALC expression levels may be lowered by treatment with the proteasome inhibitor bortezomib.

Despite progress made in understanding the biology of acute myeloid leukemia (AML), the long-term survival of most patients remains poor. In recent years numerous gene mutations and differential expression levels of leukemia-associated genes have been identified which associate with the prognosis of AML patients. In addition, several microRNAs (miRs) have been found to be important regulators in the complex cascades of various cancer pathways. miR genes are located throughout the genome, but approximately one third reside within introns of "host" genes. However, putative functional interactions between the intronic miRs and their hosts which may have important biological consequences have received relatively little attention.

The BAALC oncogene is mainly expressed in neural cells, undifferentiated hematopoietic cells, and blast cells from AML and acute lymphoblastic leukemia (ALL) patients. In AML overexpression of BAALC has been repeatedly associated with poor prognosis, especially impacting on the achievement of complete remission following induction chemotherapy. In addition, aberrant expression of BAALC has been described in several other malignancies, including malignant melanoma, brain tumors and childhood gastrointestinal stromal tumors. Research shows the involvement of the BAALC locus in general cancer pathways. In melanoma, high expression of BAALC is associated with the presence of BRAF mutations, which reflect a more aggressive disease phenotype. Evidence indicates that BAALC supports leukemogenesis but is not able to cause leukemia on its own. Recently, microRNA miR-3151 was discovered in intron 1 of the BAALC gene.

Analyzing miR-3151 and BAALC expression levels in older cytogenetically normal (CN)-AML patients, showed that high expression levels of miR-3151 independently associate with poor prognosis. Patients with high expression levels of both miR-3151 and its host had the poorest outcome. miR-3151 and BAALC are co-expressed, but only in approximately two-thirds of all patients. Thus, the partly discordant expresser status of miR-3151 and its host gene BAALC, the independent impact of the two genes on outcome, and the fact that patients overexpressing both miR-3151 and its host had significantly worse outcomes than those exhibiting upregulation of only one of the genes, suggested that the two genes contribute to the aggressiveness of the disease through independent mechanisms.

Provided herein are methods and results providing insight into the function and downstream effects of this potential oncomiR and elucidating the functional interplay with its host gene BAALC. Additionally, methods and results to identify the upstream regulator(s) of both genes to understand the mechanisms leading to their deregulated expression patterns are provided. Furthermore, paths are provided for the design of molecular treatment options for high miR-3151 and BAALC expressing patients.

Results miR-3151 Deregulates the TP53 Pathway

As previously discussed, a specific gene expression profile (GEP) associated with miR-3151-expression in 179 CN-AML patients was identified. This GEP was composed of 374 differentially expressed annotated genes with an enrichment of genes involved in differential gene expression/transcriptional regulation. To build upon these findings and to gain further insight into the cancer pathways affected by differential miR-3151 expression, this GEP was used and a canonical pathway analysis was performed. In this analysis, TP53 signaling scored as the top canonical pathway affected by aberrant miR-3151 expression levels (FIG. 26) Online in silico prediction programs identified two putative miR-3151 binding sites in the 3'-untranslated region (UTR) of TP53, indicating TP53 itself as a possible direct miR-3151 target gene.

Since the TP53-pathway has been repeatedly implicated in tumorigenesis, including AML, we hypothesized that increased miR-3151 expression may mediate the observed leukemic effects by directly deregulating this pathway.

Figure 21A:
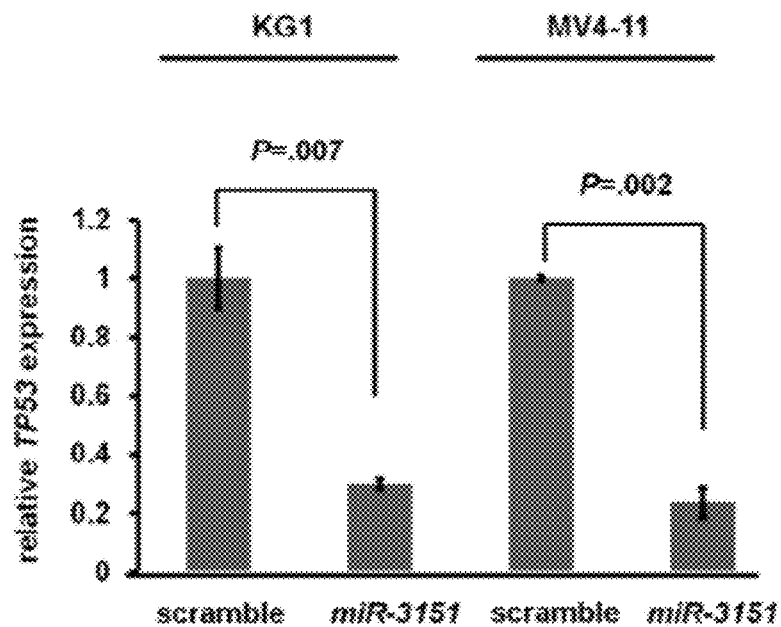
(FIG. 21A) Forced miR-3151 expression led to a decrease of TP53 expression compared to scramble control (KG1 cells: 85% decrease, P=0.007; MV4-11 cells: 41% decrease, P=0.002). All graphs are displayed as mean±standard deviation of at least three independent experiments.
Figure 21B:
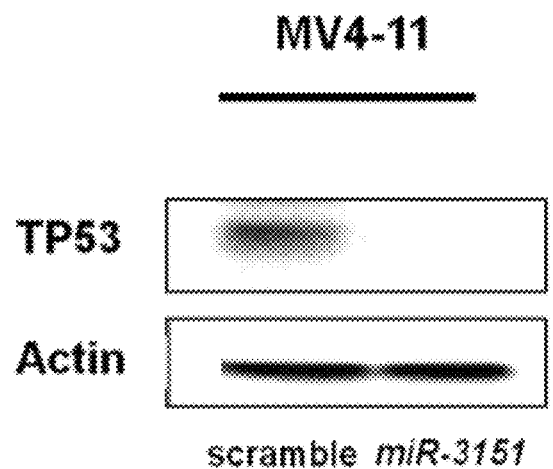
(FIG. 21B) Shown is a Western Blot of TP53 expression comparing miR-3151 infected MV4-11 cells with scramble control. miR-3151 expression resulted in the elimination of TP53 protein.

Indeed, forced expression of miR-3151 led to downregulation of TP53 RNA and TP53 protein in the AML cell lines KG1 and MV4-11 (KG1 cells: 70% decrease, P=0.007; MV4-11 cells: 86% decrease, P=0.002; FIG. 1A) compared to scramble control. Western blotting confirmed the downregulation of TP53 by miR-3151 on the protein level (MV4-11 cells, FIG. 21B).

Figure 19:
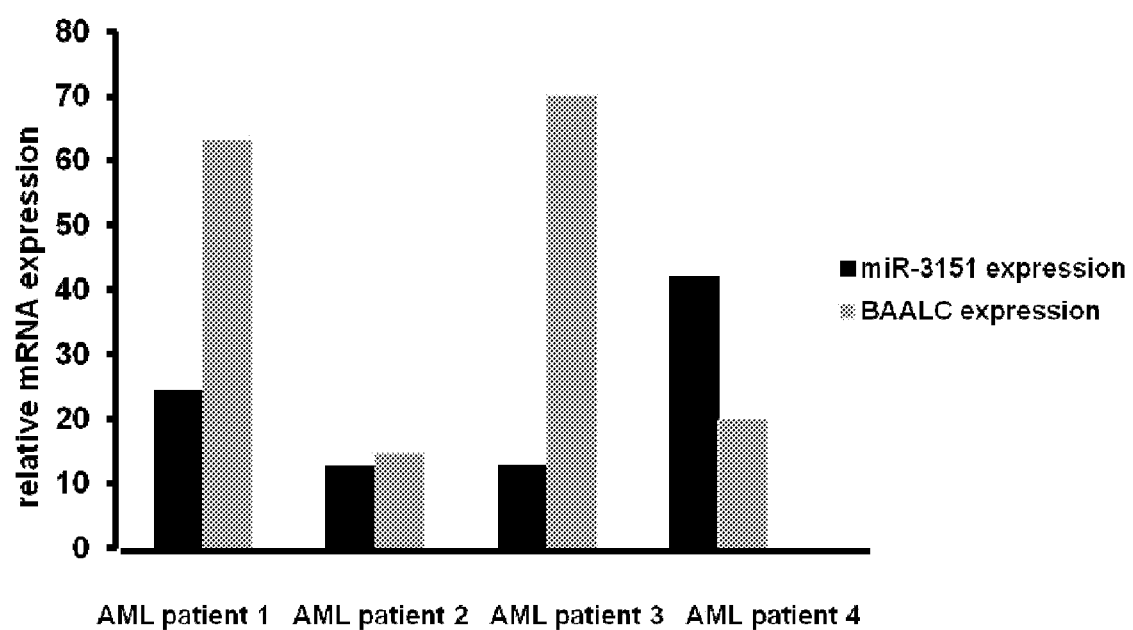
FIG. 19. Expression levels of miR-3151 and BAALC achieved by lentiviral overexpression in primary blasts of four AML patients. The mRNA expression levels were determined by RT-PCR and are displayed relative to miR-3151 and BAALC expression levels infected with scramble control (set as 1).

To determine the effects of miR-3151 expression on the TP53 pathway in AML, primary blasts of four AML patients were infected with either lentiviral miR-3151 expression construct or scramble control. The effects of forced miR-3151 expression were then tested on a panel of 30 TP53 pathway associated genes versus scramble control using RT-PCR TP53-pathway plates (Applied Biosystems). Infection of the primary patient blasts with the miR-3151 expression construct resulted in an average 23-fold (range: 13-42-fold) overexpression of miR-3151 (FIG. 19).

Figure 21C:
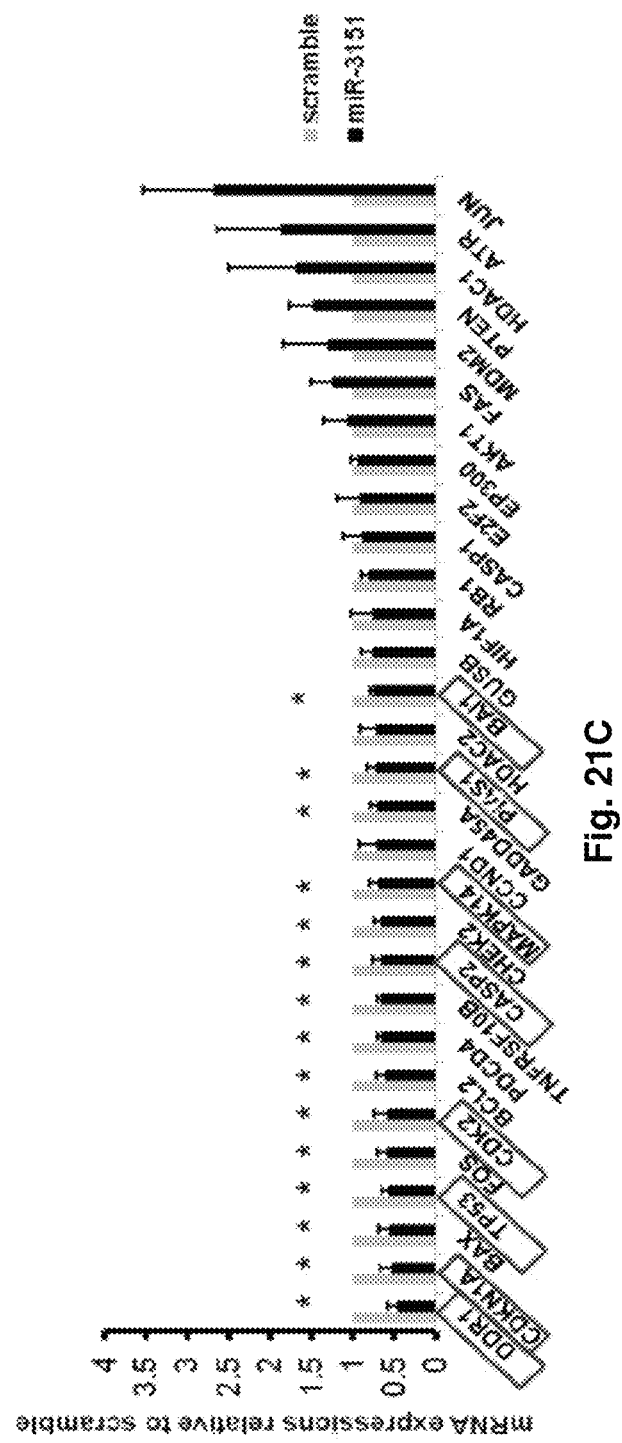
(FIG. 21C) Primary blasts of four AML patients were infected with miR-3151 expression construct vs. scramble control and mRNA expression levels of 30 TP53 pathway members were analyzed using RT-PCR. Forced miR-3151 expression led to a decrease of TP53 expression and to a significantly decreased expression of 15 TP53 key pathway members (* indicates P≤0.05). Red boxes indicate the genes which harbor one or more predicted miR-3151 binding sites in their 3'-UTR. The graphs are displayed as mean±S.E.M.
Figure 21D:
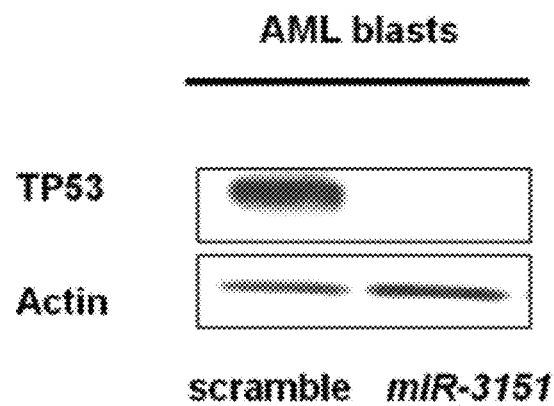
(FIG. 21D) Western Blot of TP53 expression comparing miR-3151 infected patient cells with scramble control. miR-3151 expression resulted in the elimination of the TP53 protein.

Comparing miR-3151 overexpressing patient blasts vs. scramble control, a significant downregulation was observed of 15 of 30 TP53 pathway genes (CASP2 [P=0.02], PIAS1 [P=0.03], BAX [P=0.02], BCL2 [P=0.01], CDKN1A [P=0.01], CDK2 [P=0.04], FOS [P=0.02], GADD45A [P=0.007], MAPK14 [P=0.02], CHEK2 [P=0.007], DDR1 [P=0.005], BAI1 [P=0.001], PDCD4 [P=0.002], TNFRSF10B [P<0.001]) and, of TP53 itself (P=0.007, FIG. 21C). The downregulation of TP53 on the protein level was validated using protein extracted from miR-3151 infected blasts of the aforementioned AML patients (FIG. 21D). In silico analysis of the significantly downregulated genes revealed that, in addition to TP53, 7 of the other 15 genes also harbor putative miR-3151 binding sites in their 3'-UTRs and therefore represent potential direct targets of miR-3151 (DDR1, CDKN1A, CDK2, CASP2, MAPK14, PIAS1, BAI1).

miR-3151 Directly Targets TP53

Figure 21E:
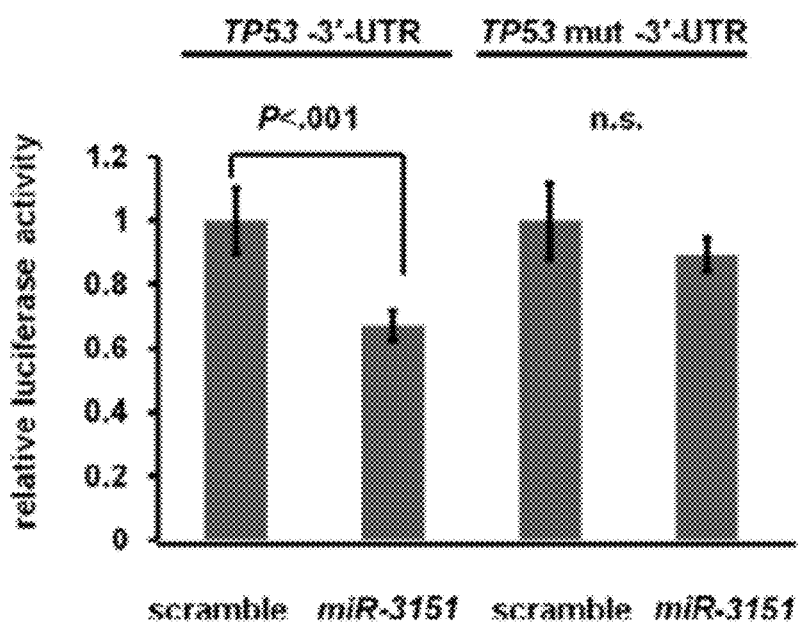
(FIG. 21E) The effect of miR-3151 on luciferase activity is shown for the TP53 3'-UTR (cloned 3' of the luciferase gene). Addition of miR-3151 resulted in a 40% decrease in luciferase activity compared to scramble control. This effect was abrogated after mutation of the respective binding sequences of the predicted miR-3151 binding sites (labeled as TP53 mut-3'-UTR).

It was predicted that miR-3151 binds to the 3'-UTR of TP53, suggesting TP53 as a direct target of miR-3151. To demonstrate that TP53 is a direct target of miR-3151, the 3'-UTR with the sequence containing one of the two predicted miR-3151 binding sites was cloned 3' of the luciferase gene into a luciferase reporter vector (pGL4.24). The luciferase assay demonstrated a 40% decrease in luciferase activity for the TP53 construct after addition of miR-3151 compared to scramble control (FIG. 21E). The observed downregulation was abrogated after mutation of the seed sequence of the predicted miR-3151 binding site (FIG. 21E). Thus, TP53 is a direct target of miR-3151.

Example 4

BAALC Upregulates JUN Expression and Further Increases the TP53 Repression Caused by miR-3151

Figure 22A:
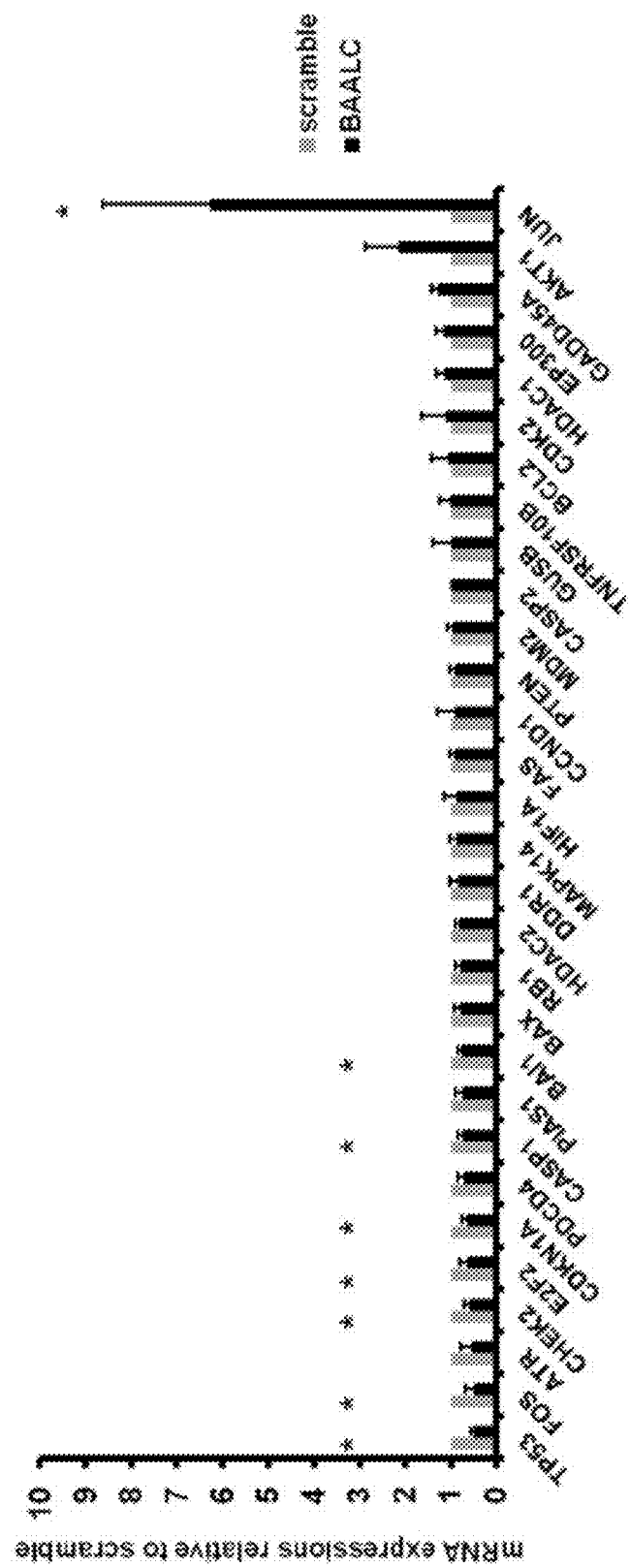
(FIG. 22A) Primary blasts of four AML patients were infected with BAALC expression construct vs. scramble control and mRNA expression levels of 30 TP53 pathway members were analyzed using RT-PCR. Forced BAALC expression led to an increase of JUN expression levels, a decrease of TP53 expression, and to significantly decreased expression of six other TP53 pathway members (* indicates P≤0.05). The graphs are displayed as mean±S.E.M.
Figure 22B:
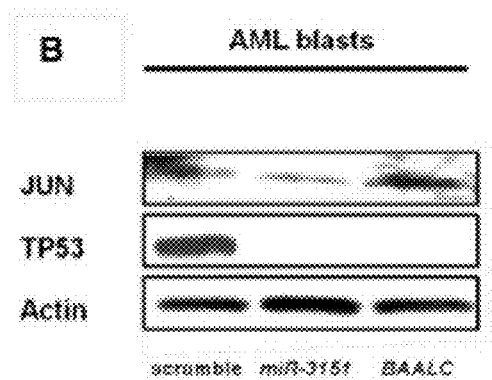
(FIG. 22B) Western Blot of JUN expression comparing BAALC infected patient cells with scramble control. High BAALC expression results in an increase of the JUN protein and an elimination of TP53.

To investigate and substantiate that miR-3151 and its host gene BAALC affect the same pathway but through distinct mechanisms, the effects of forced BAALC expression on the mRNA levels of the TP53-associated gene panel in the same set of four AML patients vs. scramble control were tested. Interestingly, the predominant effect observed after forced BAALC expression was an upregulation of the oncogene JUN (mean: 5.5 [standard error: ±2.2]-fold upregulation, FIG. 22A). Using protein extracts from the same infection, this upregulation could also be validated on the protein level (FIG. 22B). As part of the AP1 transactivating complex, JUN has been shown to be overexpressed in several human malignancies, including AML. The transcriptional activation of numerous targets leads to increased proliferation and decreased apoptosis of cancer cells. In addition, JUN has been found to directly lead to a transcriptional repression of TP53. Thus BAALC may deregulate the TP53 pathway by increasing JUN expression which in turn might repress TP53 expression.

In addition to the upregulation of JUN, a significant downregulation was observed of CASP1 (P=0.04), FOS (P=0.03), CDKN1A (P=0.01), E2F2 (P=0.003), CHEK2 (P=0.01), BAI1 (P=0.02), and also TP53 itself (P<0.001). The downregulation of TP53 was also validated at the protein level of the infected AML patient blasts (FIG. 22B).

Figure 22C:
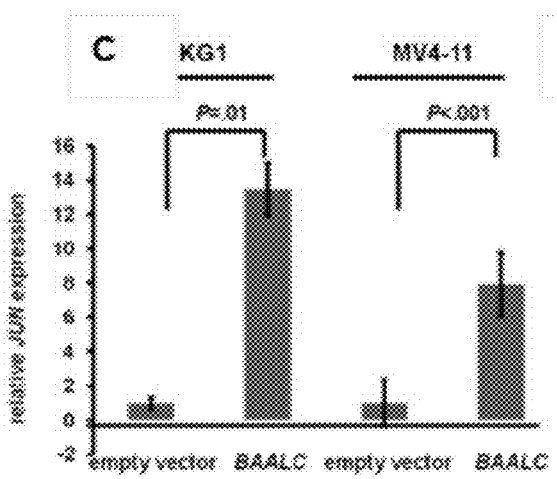
(FIG. 22C) Forced expression of BAALC resulted in upregulation of JUN expression (MV4-11 cells: 7.5-fold upregulation, KG1 cells: 13.5-fold upregulation).
Figure 22D:
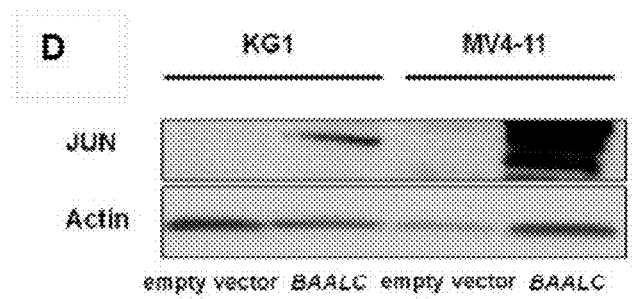
(FIG. 22D) The upregulation of JUN was validated on the protein level for both cell lines.
Figure 22E:
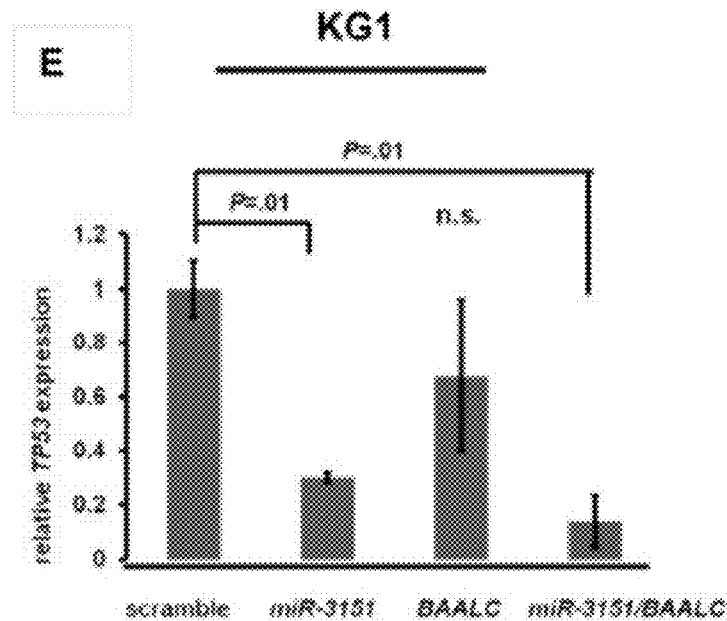
(FIG. 22E) and (FIG. 22F) While miR-3151 alone downregulated TP53, forced BAALC expression did not lead to a significant downregulation of TP53 in KG1 and MV4-11 cells. Co-infection of BAALC and miR-3151 further enhanced the downregulation of TP53 when compared to miR-3151 alone.
Figure 22F:
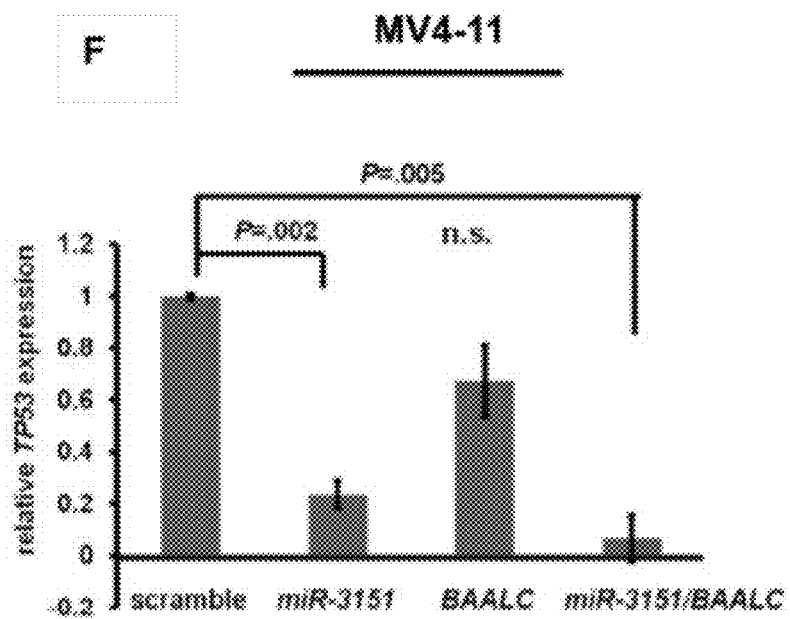
FIG. 22. BAALC upregulates JUN expression.

Next, to validate these findings, the JUN expression levels were measured in stably BAALC expressing MV4-11 and KG1 cells vs. scramble control. An upregulation of JUN expression was found (MV4-11 cells: 9.6-fold upregulation, KG1 cells: 13.5-fold upregulation, FIG. 22C). This upregulation was validated at the protein level in both cell lines (FIG. 22D). Since JUN has been shown to directly downregulate TP53 expression, whether forced expression of both miR-3151 and BAALC potentiates the downregulation of TP53, as compared to forced expression of miR-3151 alone, was analyzed. KG1 and MV4-11 cells were co-infected with the expression constructs of both genes and analyzed the resulting TP53 expression levels. Indeed, the combination of miR-3151 and BAALC led to an 86% (KG1) and 93% (MV4-11) decrease of TP53 expression compared to scramble control (FIGS. 22E and F) Unlike to the effects of forced BAALC expression observed in the primary patient blasts, only a mild downregulation of TP53 expression levels caused by sole BAALC overexpression was observed, which did not reach statistical significance (KG1 cells: P=0.27, MV4-11 cells: P=0.08; FIGS. 22E and F).

These results supported the hypothesis that both miR-3151 and its host gene BAALC affect the TP53-pathway, by either directly targeting TP53 (in the case of miR-3151) or indirectly repressing TP53 expression via upregulation of JUN (in the case of BAALC).

Example 5

Forced miR-3151 Expression Leads to Increased Growth of AML Cells which is Enhanced by Co-Infection with its Host Gene BAALC Since higher expression levels of miR-3151 are associated with a shorter disease-free and overall survival in CN-AML patients, whether changes in miR-3151 expression levels impact on the growth of leukemia cells was evaluated. Additionally, since patients with high expression levels of both miR-3151 and its host gene BAALC had the shortest survival of all patients, whether simultaneous overexpression of both genes might additionally add to the effects on leukemia cell proliferation was analyzed.

Figure 23A:
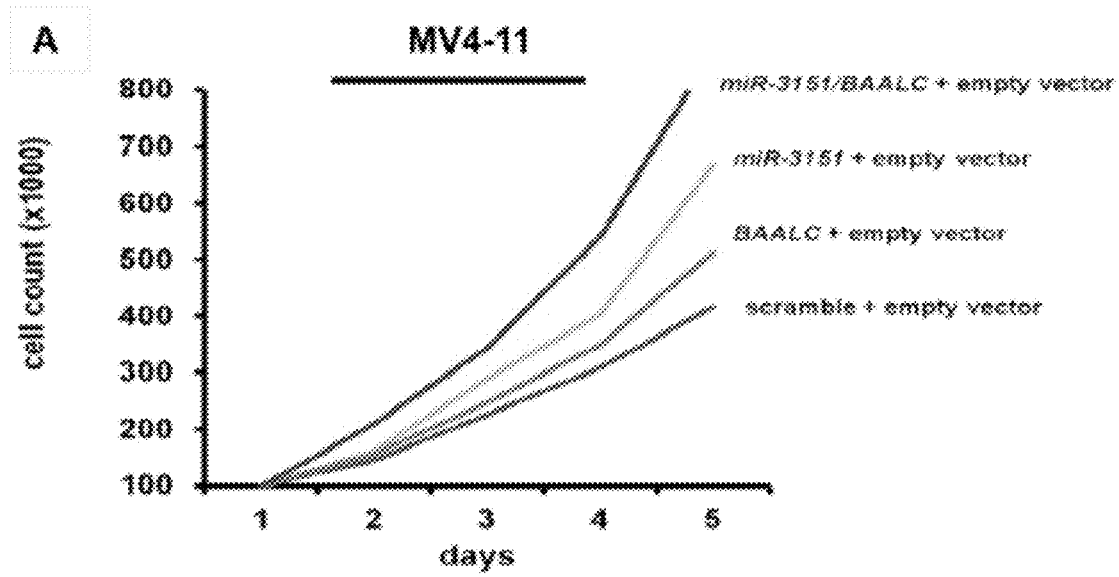
(FIG. 23A) MV4-11 cells were infected with miR-3151, BAALC, scramble or both miR-3151 and BAALC expression constructs. Successfully infected cells were transfected with empty vector construct (to allow comparison to forced TP53 expression, as displayed in FIG. 23B) and counted for five consecutive days to compare the cell growth. Forced expression of miR-3151 increased the cell growth of low miR-3151 expressing MV4-11 cells. miR-3151/BAALC expressing cells showed the fastest growth.
Figure 23B:
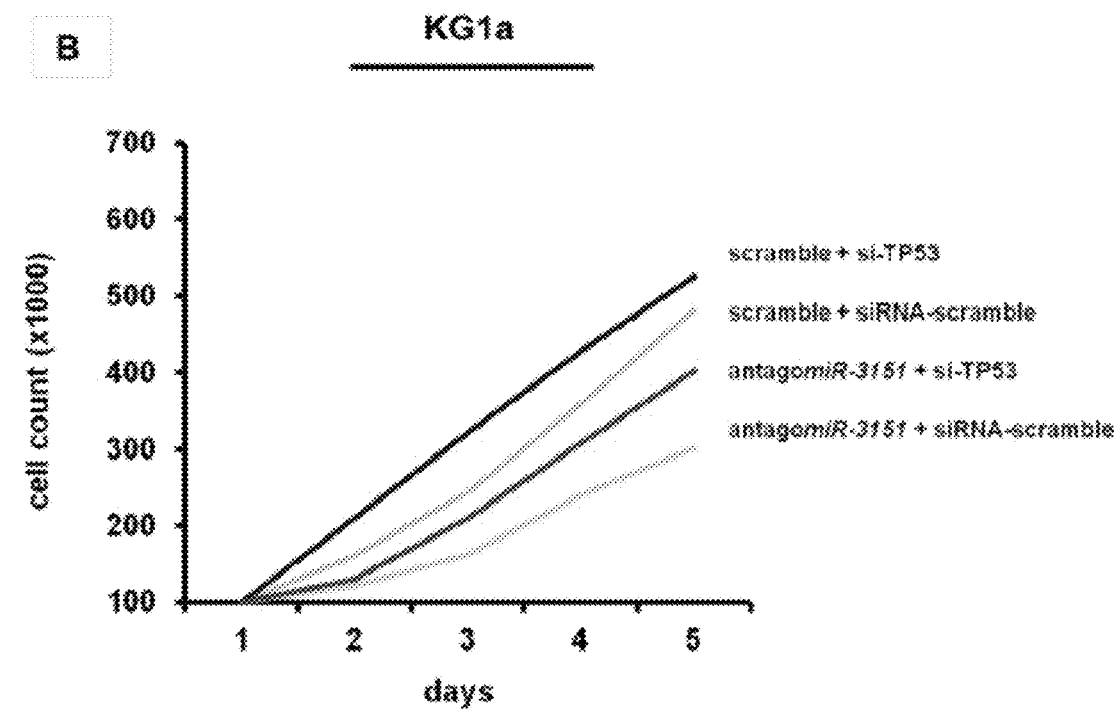
(FIG. 23B) KG1a cells were infected with antagomiR-3151, or scramble expression constructs. Successfully infected cells were transfected with either siRNA against TP53 or siRNA scramble control. Cells were counted for five consecutive days to compare the cell growth. Downregulation of miR-3151 in KG1a cells led to reduced cell growth compared to scramble control. Knock-down of TP53 using siRNA could in part rescue the observed growth reduction of antago-miR-3151 expressing cells.
Figure 23C:
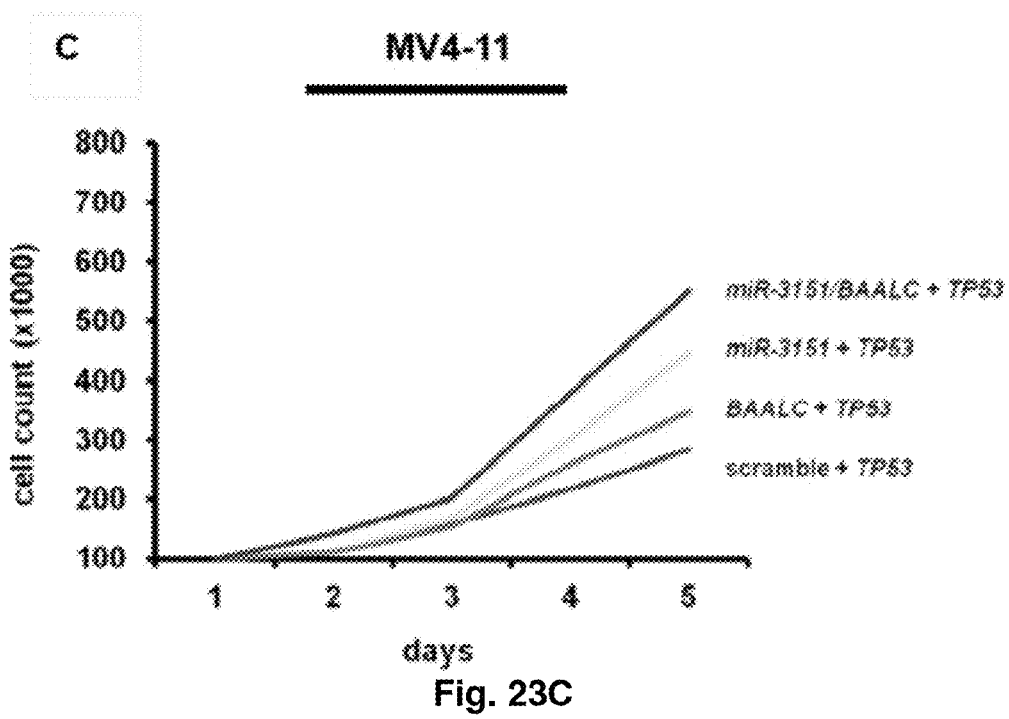
(FIG. 23C) In MV4-11 cells stably expressing miR-3151, BAALC, scramble or both miR-3151 and BAALC, the growth advantage caused by miR-3151 can be partly reduced by re-introduction of TP53. miR-3151/BAALC expressing cells still showed the fastest growth, but the absolute cell counts were reduced by 50% when compared to cells co-transfected with empty vector (displayed in FIG. 23A).

Using low miR-3151 expressing MV4-11 cells for overexpression and high miR-3151 expressing KG1a cells for knock-down, forced expression of miR-3151 increased cell growth (FIG. 23A), while downregulation of miR-3151 led to reduced cell growth (FIG. 23B). While cell growth of BAALC overexpressing cells was less than the miR-3151 induced growth, cells overexpressing both miR-3151 and BAALC had the fastest growth rates of all experimental setups (FIGS. 23A and B).

Having validated TP53 as a target gene of miR-3151, whether forced expression of TP53 reduces the growth advantage caused by miR-3151 overexpression was tested. Indeed, co-transfection of TP53 into stably miR-3151 expressing MV4-11 cells reduced cell growth, while co-transfection with TP53-siRNA increased the growth of stably antagomiR-3151 expressing KG1a cells (FIGS. 23B and C).

Example 6 miR-3151 and BAALC Inhibit Apoptosis of AML Cells and Primary AML Patient Blasts It was analyzed that, given the effect of miR-3151 and BAALC on TP53 and JUN expression levels, the observed growth advantage of miR-3151 and especially miR-3151/BAALC overexpressing cells may be caused by disruption of the apoptosis pathways downstream of TP53 and JUN. Therefore, chemiluminescent assays were performed to assess the activities of CASP3 and 7 as the ultimate downstream effectors of both apoptosis cascades.

Figure 14A:
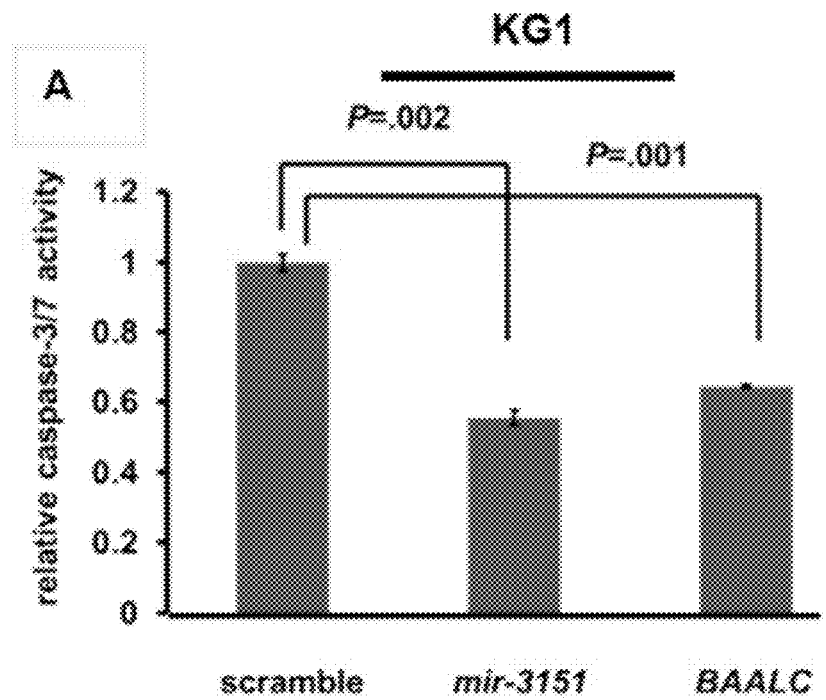
(FIG. 14A) Shown are caspase 3/7 chemiluminescent assays of AML cells after infection with miR-3151, BAALC and scramble control. The results show a decrease of caspase activities (and consequently apoptosis) in the miR-3151 and BAALC overexpressing cells(KG1: miR-3151 vs. scramble: P=0.002, BAALC vs. scramble: P=0.001). All graphs are displayed as mean±standard deviation.
Figure 14B:
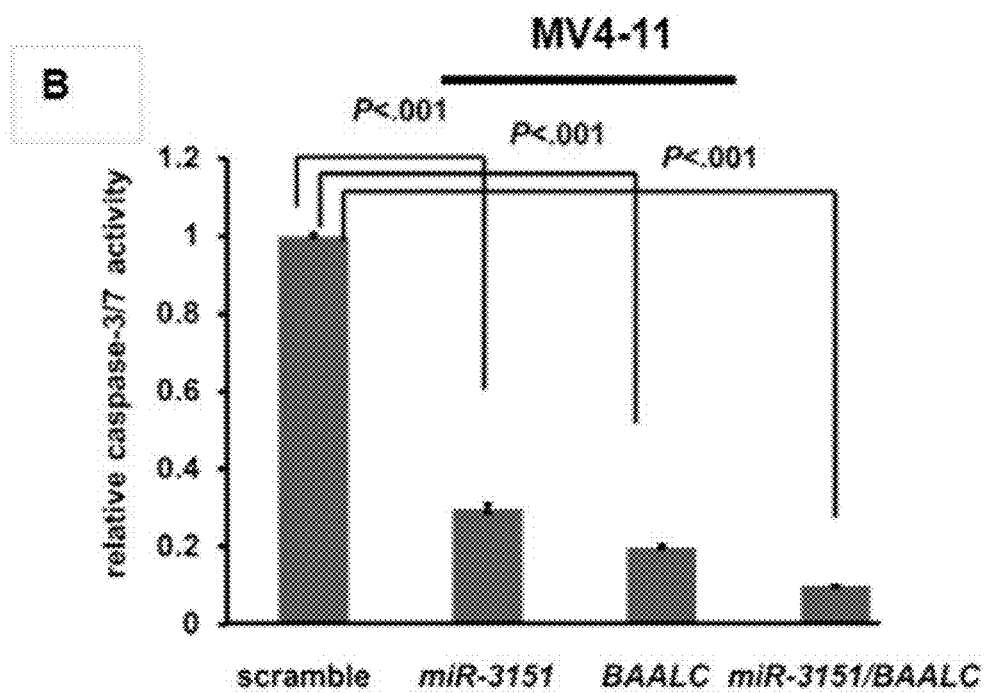
(FIG. 14B) Caspase assays of MV4-11 cells show reduced activity caused by miR-3151 and BAALC. (both P<0.001). Co-infection of the MV4-11 cells with both miR-3151 and BAALC further enhanced the apoptosis inhibition (P<0.001).
Figure 14C:
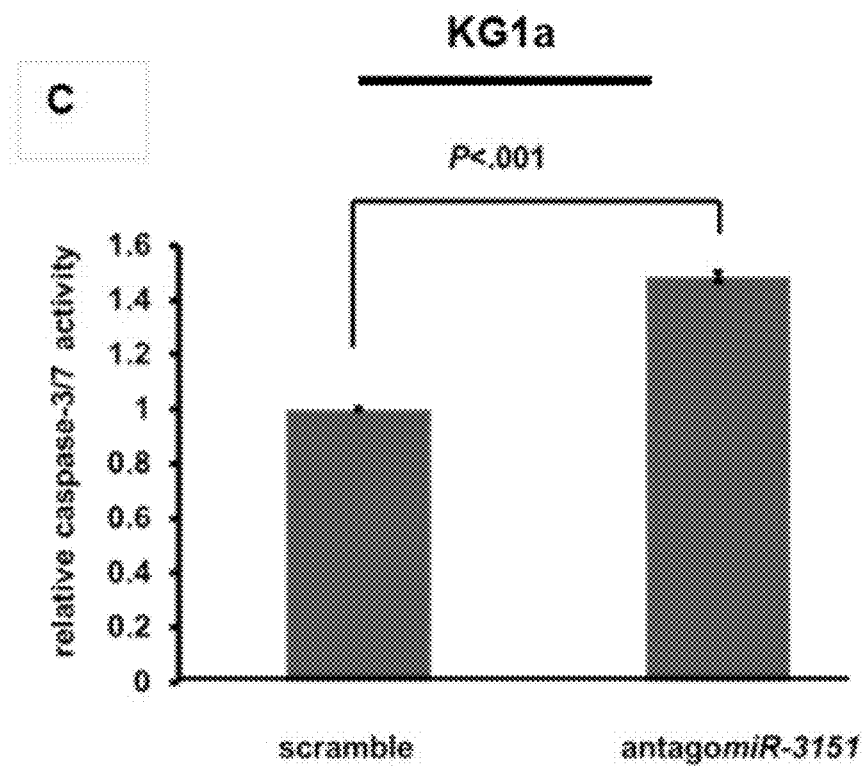
(FIG. 14C) Caspase activity of high miR-3151 expressing KG1a cells was increased by antagomiR-3151 (P<0.001).
Figure 14D:
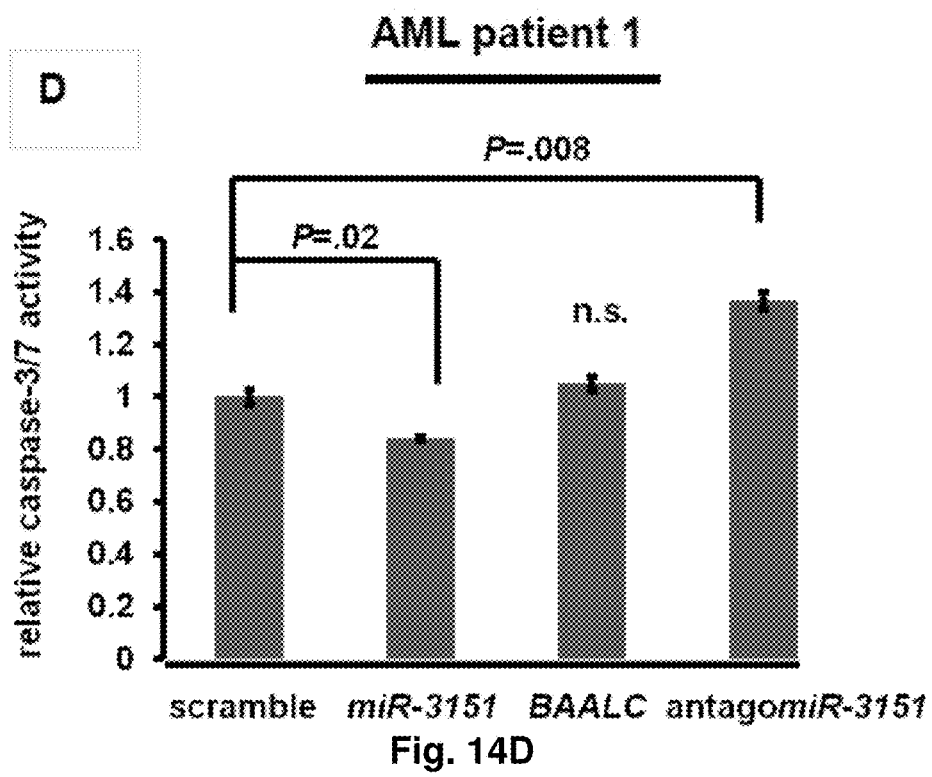
(FIG. 14D) and (FIG. 14E) Caspase activities of infected blasts of AML patients. AML patient1 and 2 (low intrinsic miR-3151 expression levels) responded to both miR-3151 overexpression and knock-down. In AML patients 2 forced BAALC expression induced an increase in caspase activity.

Analysis of the caspase activities of MV4-11 cells, KG1 and KG1a cells infected with the gene expression and/or knock-down constructs showed a significant decrease in caspase activities after 72 h (and consequently apoptosis) in all miR-3151 overexpressing cells (KG1: miR-3151 vs. scramble: 0.44-fold [±0.02] decrease, P=0.002; BAALC vs. scramble: 0.36-fold [±0.004] decrease, P<0.001; MV4-11: miR-3151 vs. scramble: 0.70-fold [±0.009] decrease, P<0.001; BAALC vs. scramble: 0.80-fold [±0.002] decrease, P<0.001; FIG. 14A). Consequently, knock-down of miR-3151 in high miR-3151 expressing KG1a cells led to an increase of caspase activity (antagomiR-3151 vs. scramble: 1.4-fold [±0.02] increase, P<0.001; FIG. 14C).

Figure 14E:
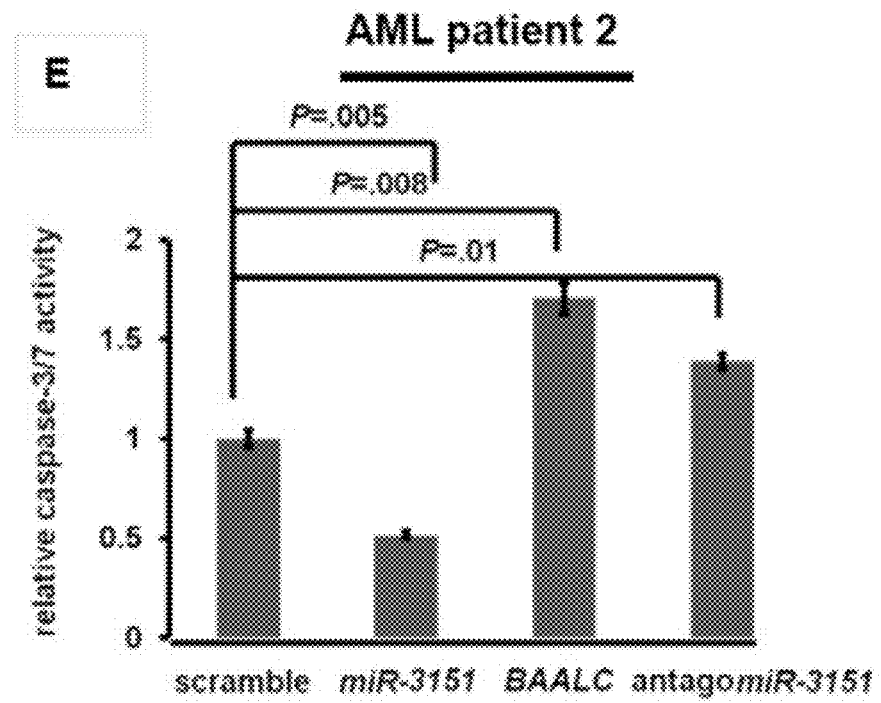
FIG. 14. miR-3151 and BAALC inhibit apoptosis of AML cells and primary AML patient blasts.
(FIG. 14F) and (FIG. 14G) AML patient 3 and AML patient 4 (high intrinsic miR-3151 expression levels) showed an increase of caspase activity upon miR-3151 knock-down. In patient 4, forced expression of BAALC led to a decrease in caspase activity.
(FIG. 14H) Western Blots detecting changes in the apoptosis cascade caused by forced miR-3151 expression. miR-3151 led to a decrease of TP53 and a reduction of both cleaved caspase 3 and cleaved PARP compared to scramble, thereby indicating reduced apoptosis.
(FIG. 14I) AntagomiR-3151 treatment of KG1a cells led to an increase of apoptosis parameters, as indicated by increases of both cleaved caspase 3 and cleaved PARP proteins.
Figure 14F:
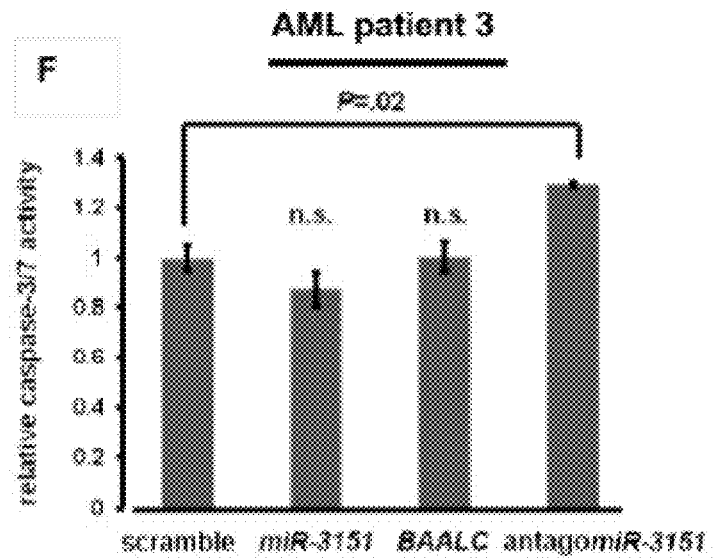
Figure 14G:
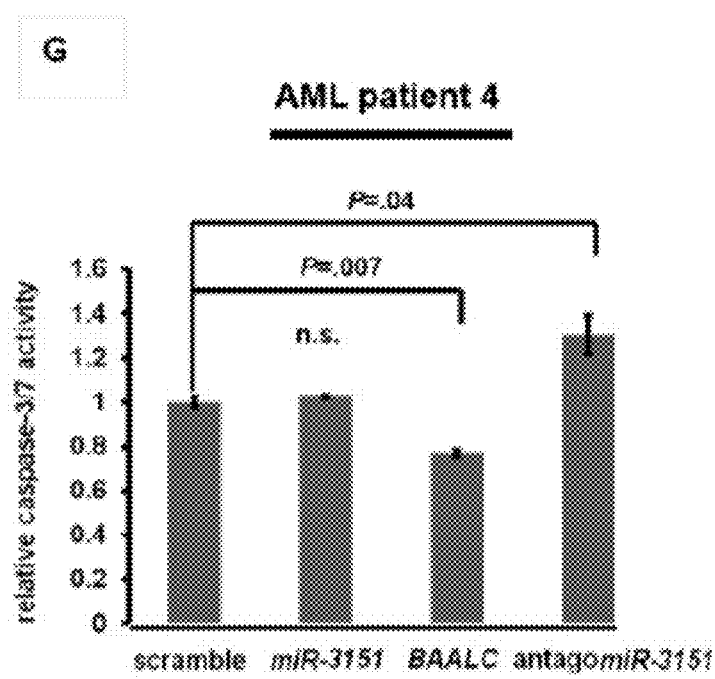

Also, the primary patient blasts responded to miR-3151 overexpression and/or knock-down with changes in their caspase activity. AML patient 1 and AML patient 2, who had relatively low intrinsic miR-3151 expression levels, responded to both miR-3151 overexpression and knock-down (AML patient 1: miR-3151: 0.16-fold [±0.02] reduction, P=0.02, antagomiR-3151: 1.37-fold [±0.008] increase; AML patient 2: miR-3151: 0.48-fold [±0.02] reduction, P=0.005, antagomiR-3151: 1.38-fold [±0.03] increase, P=0.01; FIGS. 14 D and E). AML patient 3 and AML patient 4, who had higher intrinsic miR-3151 expression levels only showed a significant increase of caspase activity upon miR-3151 knock-down (AML patient 3: 1.30-fold [±0.01] increase, P=0.02; AML patient 4: 1.30-fold [±0.09] increase, P=0.04; FIGS. 14F and G). In AML patients 2 and 4, forced expression of BAALC also led to changes in caspase activity (AML patient 2: 1.7-fold [±0.002] increase, P=0.008; AML patient 4: 0.23-fold [±0.01] reduction, P=0.007; FIGS. 14E and G).

Figure 14H:
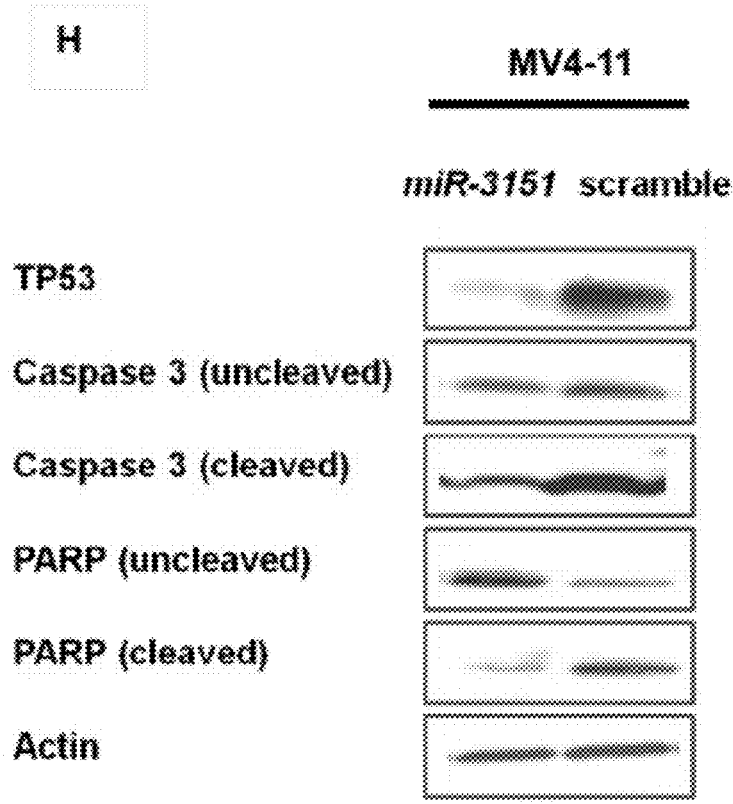
Figure 14I:
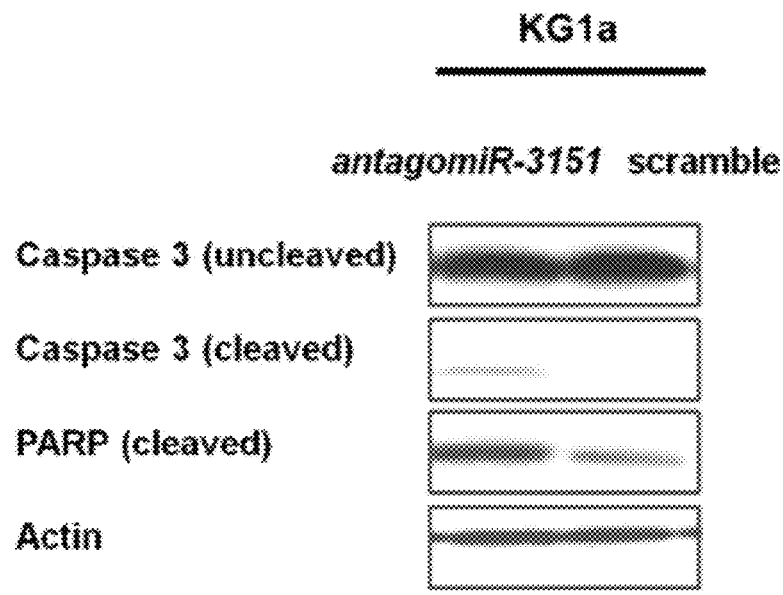

To further validate the effect of forced miR-3151 expression on CASP3, Western blotting was performed to quantify both the cleaved and uncleaved CASP3 proteins, with an increase in cleaved CASP3 indicating active apoptosis. In addition, Western blotting was performed for cleaved and uncleaved PARP protein which is affected by CASP3. As indicated by the chemiluminescent assays, forced miR-3151 expression resulted in a reduction of cleaved CASP3 and PARP1 proteins in MV4-11 cells (FIG. 14G); while the antagomiR-3151-mediated knock-down resulted in an increase of cleaved CASP3 and PARP1 levels in KG1a cells (FIG. 14H).

Example 7

Figure 20:
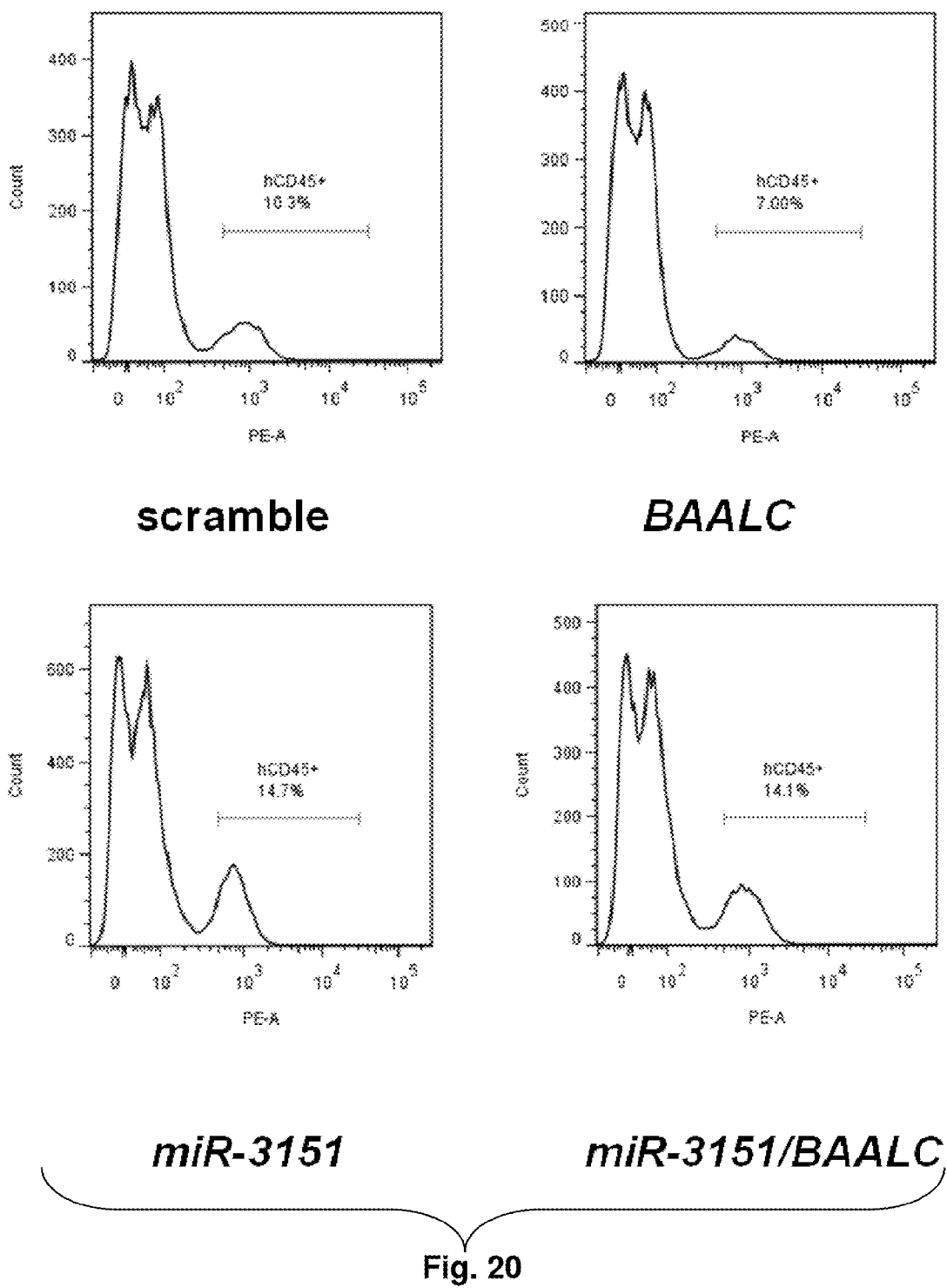
FIG. 20. Flow cytometric determination of CD45 expression in the peripheral blood of NSG mice. As a proof-of-principle, one mouse per group was bled at d+37 and CD45 positivity was measured. All mice showed an invasion of leukemic cells of human origin in the peripheral blood.
Figure 24A:
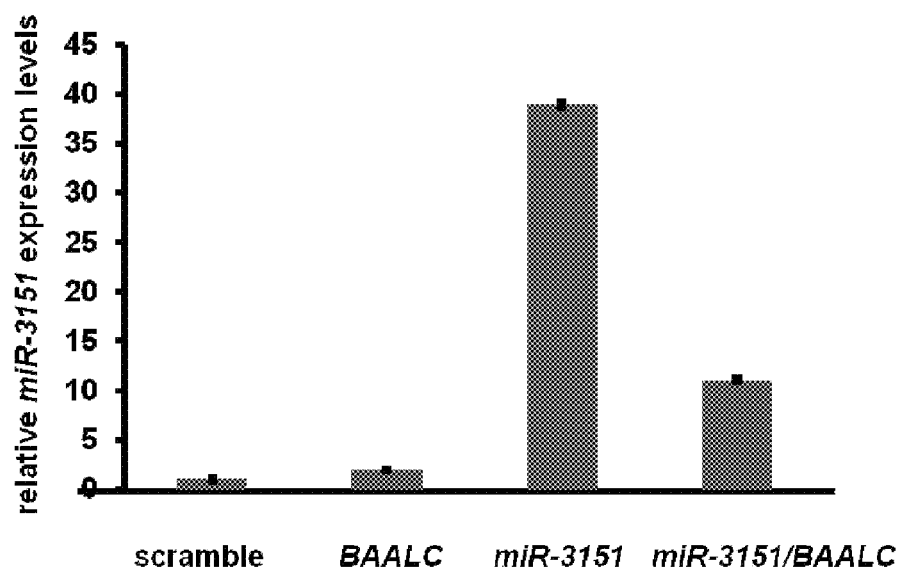
FIG. 24A-D. Determination of miR-3151, BAALC, TP53 and JUN expression in the peripheral blood of NSG mice. To validate the successful overexpression of miR-3151 and BAALC, mRNA expression levels were determined via RT-PCR in one mouse/group at d+37. All mice presented with the expected phenotype (FIG. 24A and FIG. 24B). Also, miR-3151 and miR-3151/BAALC overexpressing mice showed a downregulation of TP53 expression levels (FIG. 24C), while BAALC overexpressing mice presented with increased JUN expression (FIG. 24D).
Figure 24B:
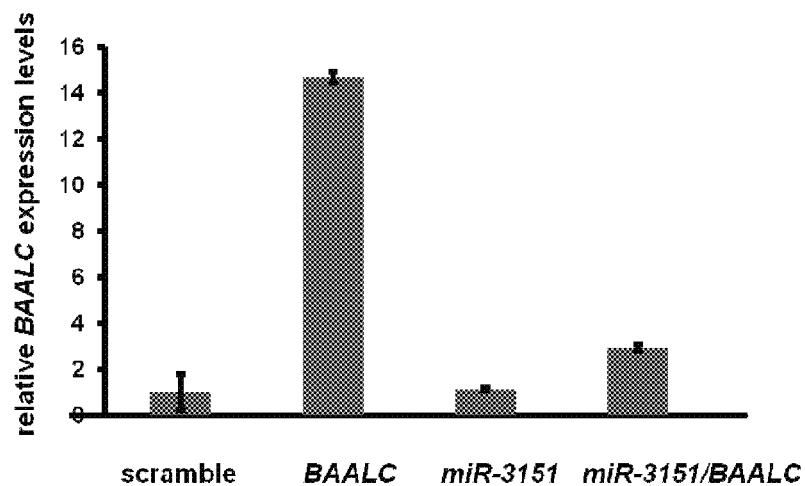

Overexpression of miR-3151, Alone and in Combination with BAALC, Causes Increased Leukemogenesis In Vivo To test whether forced miR-3151 and BAALC expression would also lead to an increase in leukemia cell growth reflected by a more aggressive disease phenotype in vivo, the inventors stably overexpressed miR-3151, BAALC and the combination of both genes in murine adapted MV4-11 cells which were injected in NOD scid gamma knock-out (NSG) mice (n=6 mice/group). Depending on the number of cells injected, these mice develop an aggressive leukemia 2-6 weeks after injection. Engraftment of the MV4-11 cells was validated by flow cytometric determination of CD45 positivity at d+37 (FIG. 20A). Successful overexpression of the genes in the peripheral blood of mice bled at d+37 was determined using RT-PCR (FIGS. 24A and B). The survival of mice within the groups was then compared between the groups and vs. scramble expressing controls.

Figure 15A:
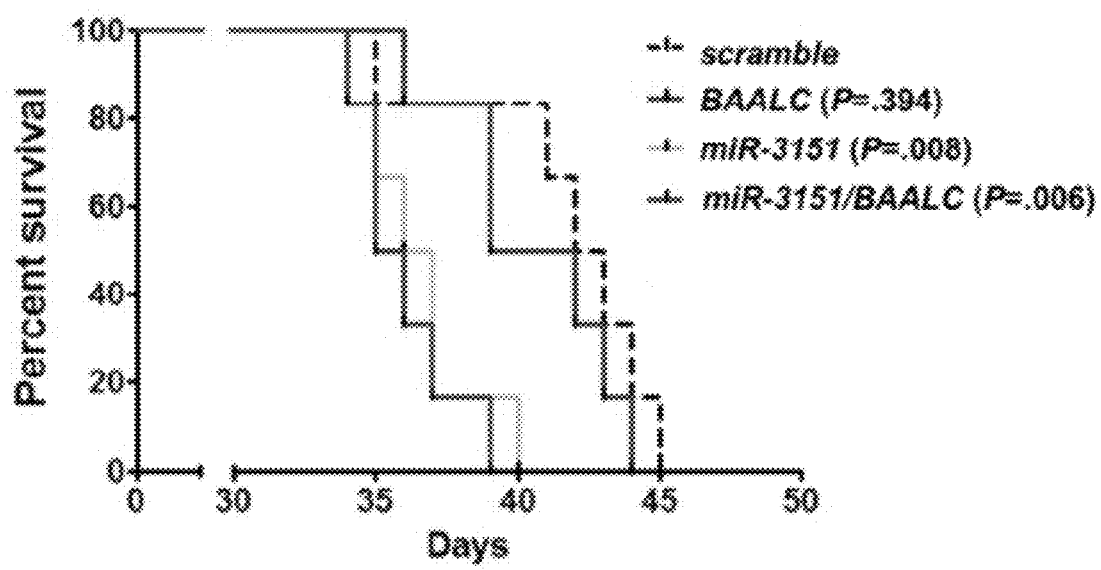
FIG. 15. miR-3151 increases leukemogenesis in vivo (FIG. 15A) Survival of NSG mice after injection of MV4-11 cells overexpressing miR-3151, BAALC, miR-3151/BAALC or scramble control (n=6 mice/group). Both high expression of miR-3151 alone or in combination with BAALC led to a significantly shorter survival of the mice compared to scramble control (miR-3151/BAALC: median survival: 35.5 days, P=0.006; miR-3151: median survival: 36.5 days, P=0.008; log rank test). The median survival of BAALC overexpressing mice did not differ from the survival of scramble controls (BAALC: median survival 41.5 days, scramble: median survival 44.5 days; BAALC vs. scramble: P=0.40).
(FIG. 15B) Macroscopic appearance of livers collected post mortem from NSG mice. miR-3151 overexpressing mice appeared to have a more severe hepatomegaly (P=0.009), while the liver weight of BAALC overexpressing mice was similar to that of scramble control. miR-3151/BAALC overexpressing mice also tended to have liver enlargements, although it did not reach statistical significance. The bar graphs display the corresponding liver weight (in g) relative to scramble control.
(FIG. 15C) Macroscopic appearance of spleens collected post mortem of NSG mice. BAALC overexpressing mice had larger spleens compared to miR-3151 expressing mice and scramble control. miR-3151/BAALC overexpressing mice had enlarged livers compared to scramble control, but the weight difference again did not reach statistical significance. The bar graphs display the corresponding spleen weights (in g) relative to scramble control.
(FIG. 15D) Hematoxylin-Eosin staining of livers and spleens of the mice. Histopathological analysis showed leukemic blast infiltration (blue staining) of livers and spleens in all compared groups. The hepatic blast infiltration was especially pronounced in the miR-3151 and miR-3151/BAALC mice and was predominantly seen around the liver vessels.

Strikingly, miR-3151-overexpressing mice—both alone and in combination with its host gene—showed the shortest survival of all mice (miR-3151/BAALC: median survival: 35.5 days, P=0.006; miR-3151: median survival: 36.5 days, P=0.008 [both vs. scramble], log-rank test; FIG. 15A). To the contrary, the median survival of BAALC overexpressing mice did not differ from the survival of scramble controls (BAALC: median survival 41.5 days, scramble: median survival 44.5 days; BAALC vs. scramble: P=0.40; FIG. 15A).

Figure 15B:
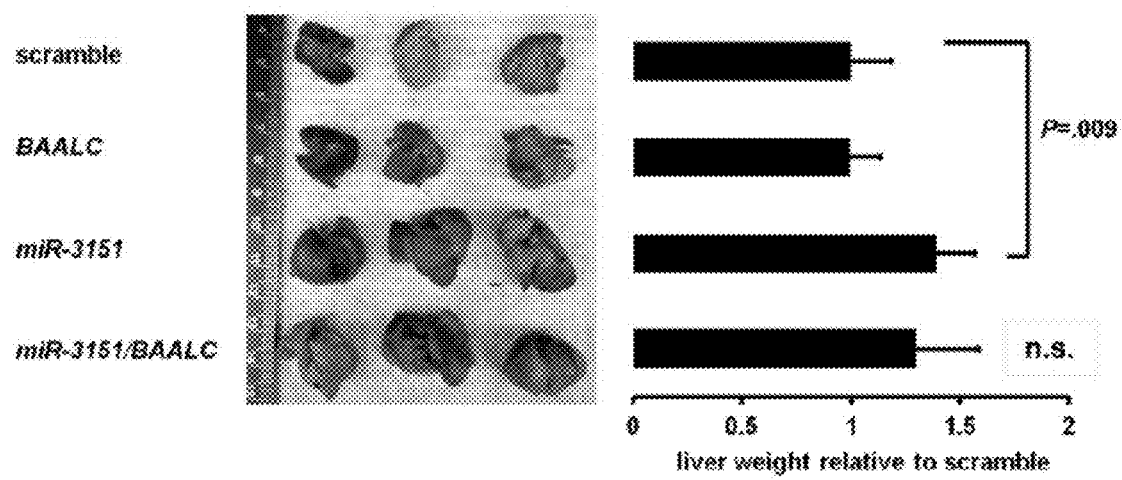
Figure 15C:
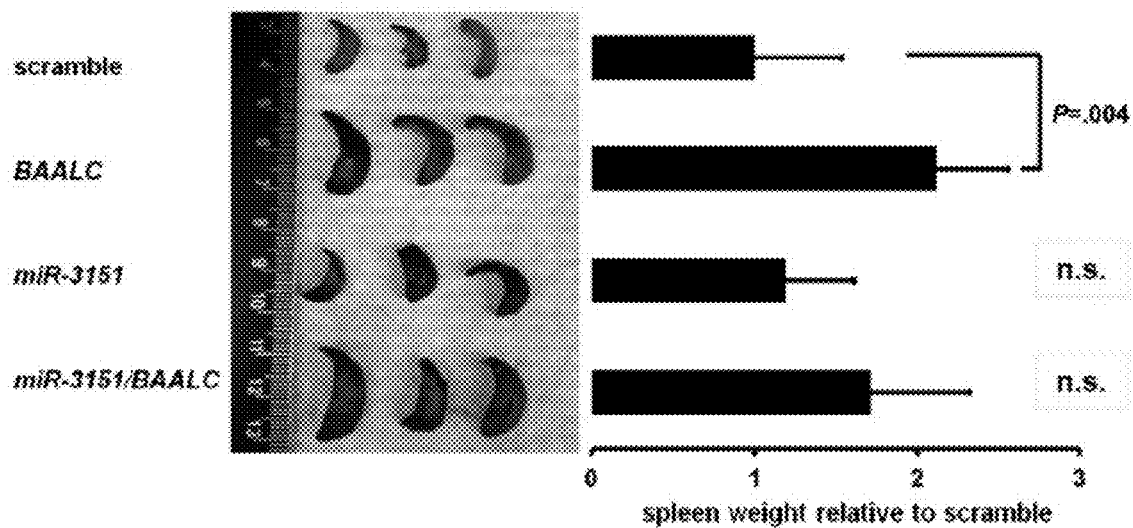
Figure 15D:
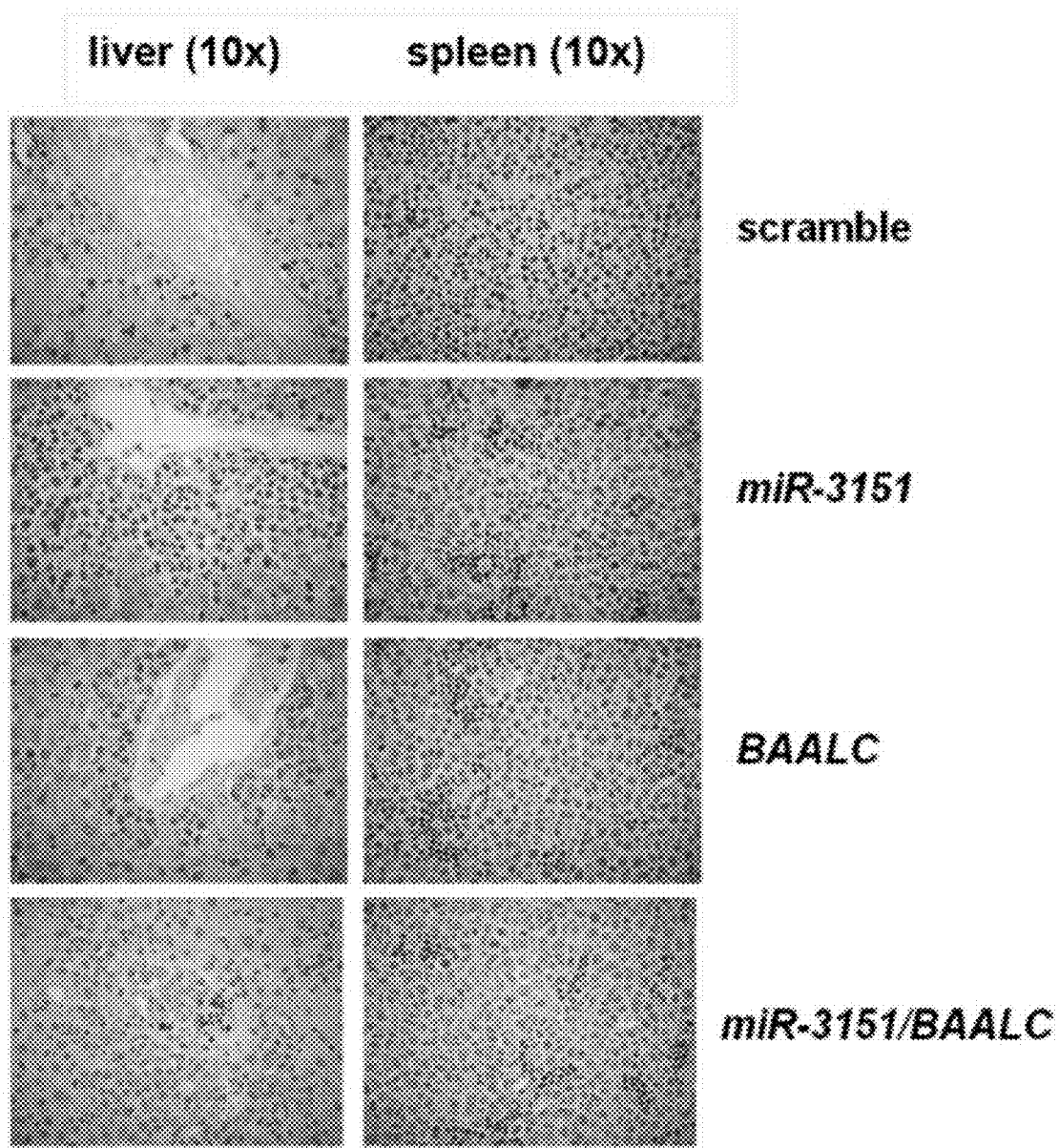

Organs were collected from every mouse post mortem and analyzed both macroscopically and histopathologically. Interestingly, while miR-3151 overexpressing mice appeared to have a more severe hepatomegaly (P=0.009, vs. scramble; FIG. 5B) but small spleens, BAALC overexpressing mice presented with large spleens (P=0.004, vs. scramble; FIG. 15C) but comparatively small livers. miR-3151/BAALC overexpressing mice seemed to share the features of both groups with both liver and spleen enlargements, even though it did not reach statistical significance (FIGS. 15B and C). Histopathological analysis (Hematoxylin-Eosin staining) showed leukemic blast infiltration of livers and spleens in all groups (FIG. 15D). The hepatic blast infiltration was especially seen in the miR-3151 and miR-3151/BAALC mice (FIG. 15D). This is in line with the observed hepatomegaly in those two groups.

Figure 24C:
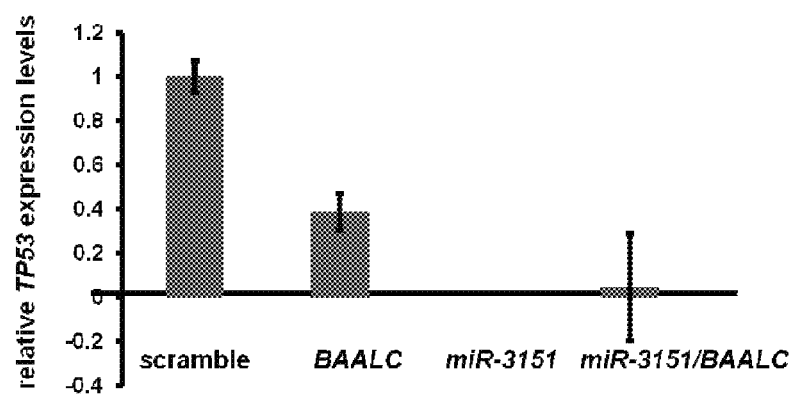
Figure 24D:
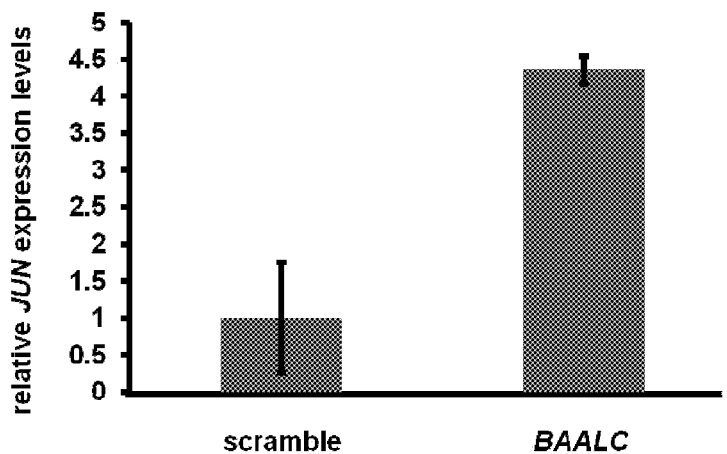
Figure 25:
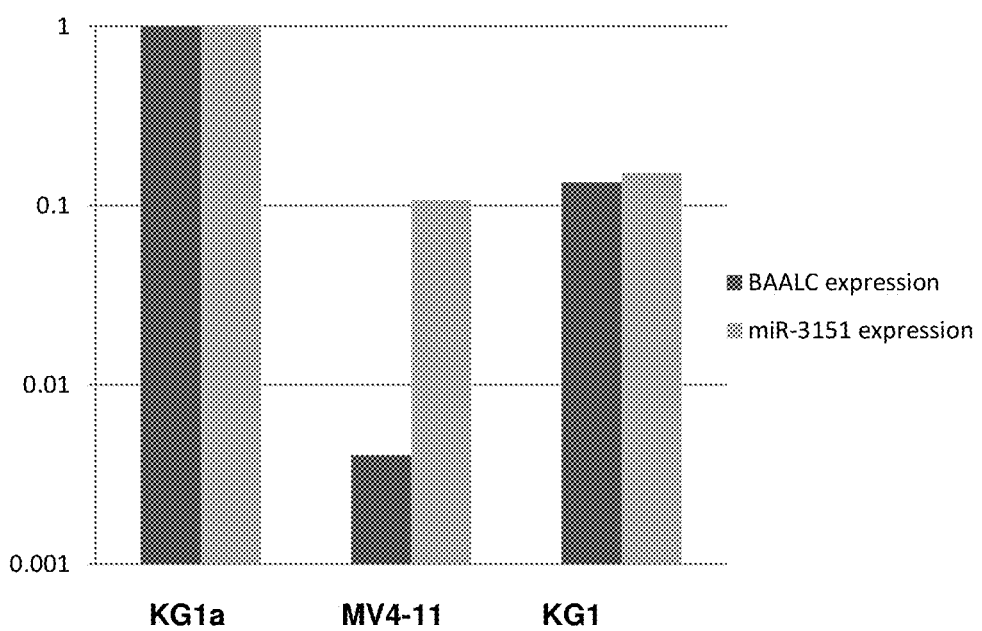
FIG. 25. Endogenous miR-3151 and BAALC expression levels in KG1a, MV4-11 and KG1 cells as determined by RT-PCR. Expression levels have been normalized to the housekeeping genes RNU44 and 18S, respectively and are displayed relative to KG1a expression levels.

When determining TP53 and JUN expression levels in the peripheral blood of mice at d+37 after injection, no TP53 could be detected in the miR-3151 overexpressing mouse and a 95% reduction of TP53 could be observed in the miR-3151/BAALC mouse (FIG. 24C). Also, a 4.4-fold increase in JUN expression levels could be observed in the BAALC mouse compared to scramble control (FIG. 24D).

Example 8

AntagomiR-3151 Increases TP53 Expression Levels and Increases Apoptosis of Melanoma Cells High miR-3151 and BAALC expression correlate with BRAF mutations in malignant melanoma. BRAF mutations are one of the most important drivers of melanoma, and specific inhibitors against hyperactive BRAF are therapeutic targets. Thus, miR-3151 inhibition is of enhanced potential benefit in patients with BRAF mutations.

Since miR-3151 was initially identified by deep sequencing of melanoma samples and since high BAALC expression levels have been reported as a key feature of BRAF mutated melanoma cells, we hypothesized that high expression level of both genes may also be important in the cascades of melanoma carcinogenesis. To validate the association of BRAF mutations with high BAALC expression levels and to test whether the same association is true for miR-3151 expression levels, tumor RNA was obtained from 20 malignant melanoma patients (Asterand) and their miR-3151 and BAALC expression levels were determined using RT-PCR. In addition, all patients were screened for the presence of BRAF mutations. The BRAF V600 mutation was detected in 5 of 20 patients. Comparing the miR-3151 and BAALC expression levels of BRAF mutated patients vs. BRAF wild type patients, BRAF mutated patients presented with significantly higher expression levels of both genes (miR-3151: 4.85-fold [±3.90] higher expression, P=0.002; BAALC: 13.6-fold [±7.43] higher expression, P<0.001).

Figure 16A:
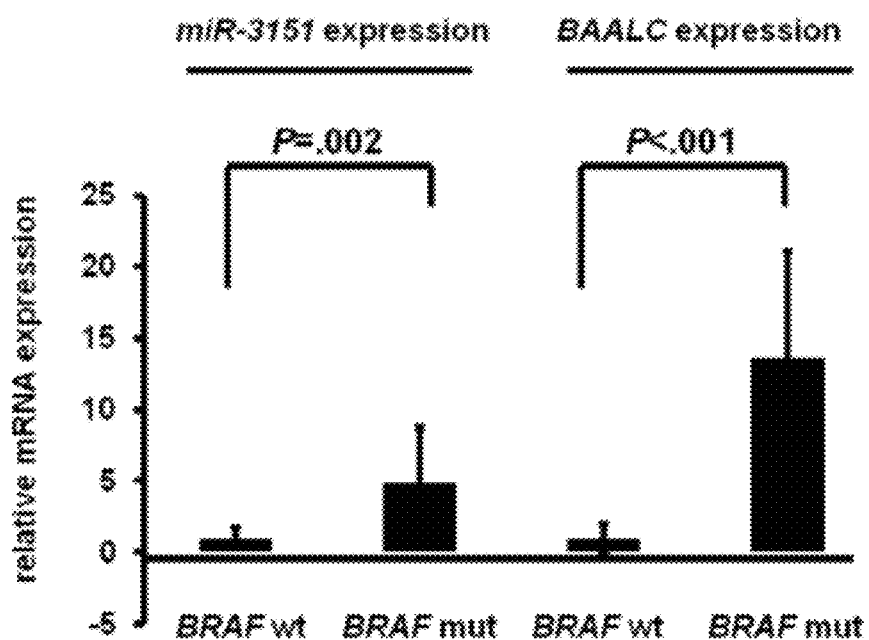
(FIG. 16A) miR-3151 and BAALC expression levels of malignant melanoma patients (n=20) according to their BRAF mutation status. BRAF mutated melanoma patients (n=5) had significantly higher levels of miR-3151 (P=0.002) and BAALC (P<0.001) compared to BRAF wild type patients (n=15, mRNA expression levels of wild type patients is set to 1). All graphs are displayed as mean±standard deviation.
Figure 16B:
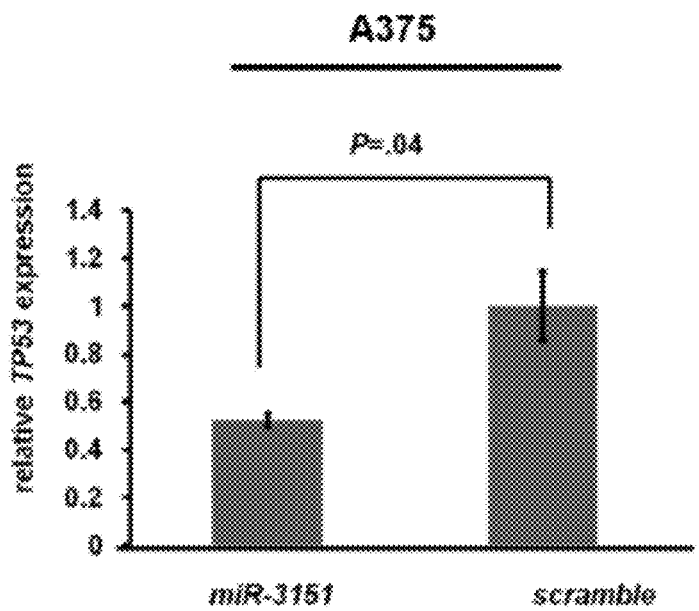
(FIG. 16B) and (FIG. 16C) Forced miR-3151 expression led to a decrease of TP53 expression compared to scramble control (A375 cells: 48% decrease, P=0.04; MeWo cells: 58% decrease, P=0.06).
Figure 16C:
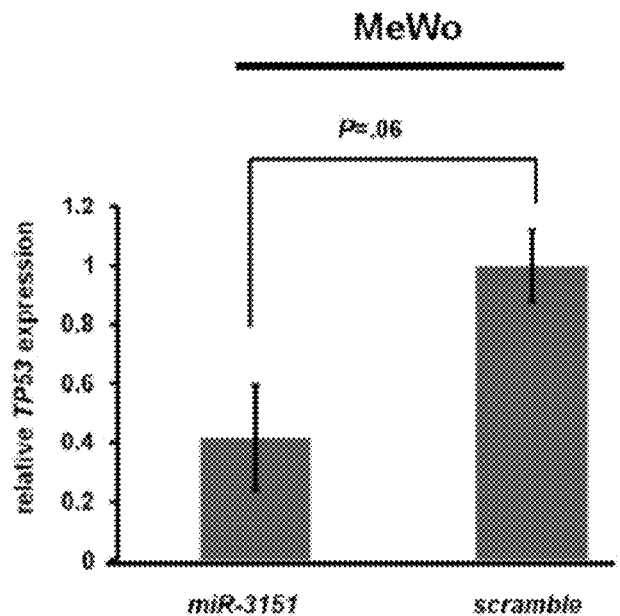
FIG. 16. Effect of miR-3151 on malignant melanoma cells.
(FIG. 16D) Western Blot of TP53 expression comparing miR-3151 infected A375 and MeWo cells with scramble control. Forced miR-3151 expression resulted in downregulation of the TP53 protein.
(FIG. 16E) and (FIG. 16F) Caspase 3/7 chemiluminescent assays of A375 (E) and MeWo (F) cells after infection with scramble control, miR-3151 and antagomiR-3151. The results show a decrease of caspase activities (and consequently apoptosis) in all miR-3151 overexpressing cells and an increase in antagomiR-3151 expressing cells (A375: miR-3151 vs. scramble: P<0.001, antagomiR-3151 vs. scramble: P<0.001; MeWo: miR-3151 vs. scramble: P=0.02, antagomiR-3151 vs. scramble: P<0.001).
Figure 16D:
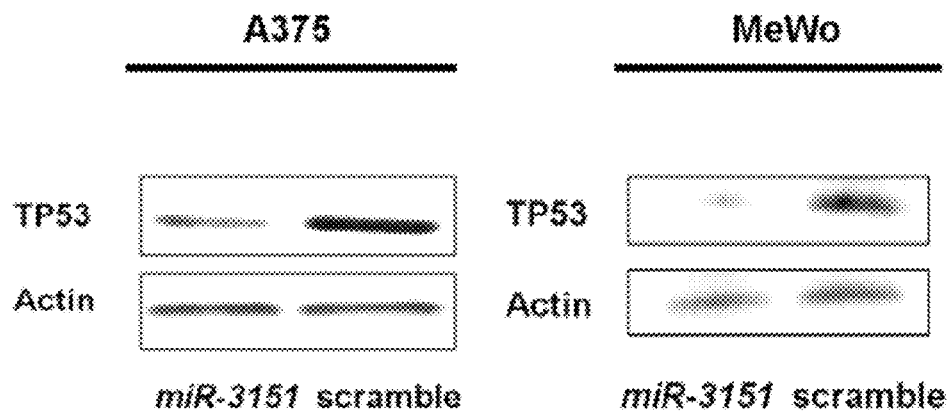
Figure 16E:
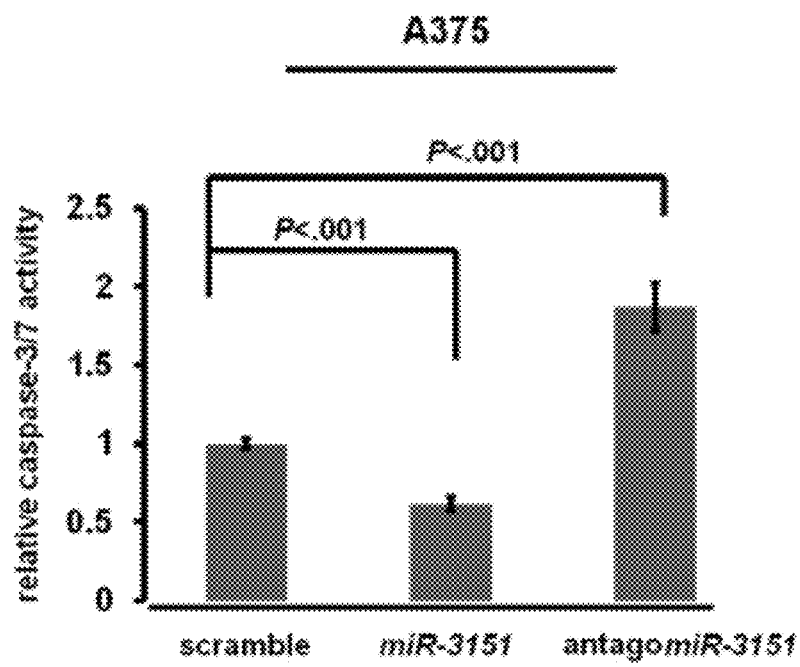
Figure 16F:
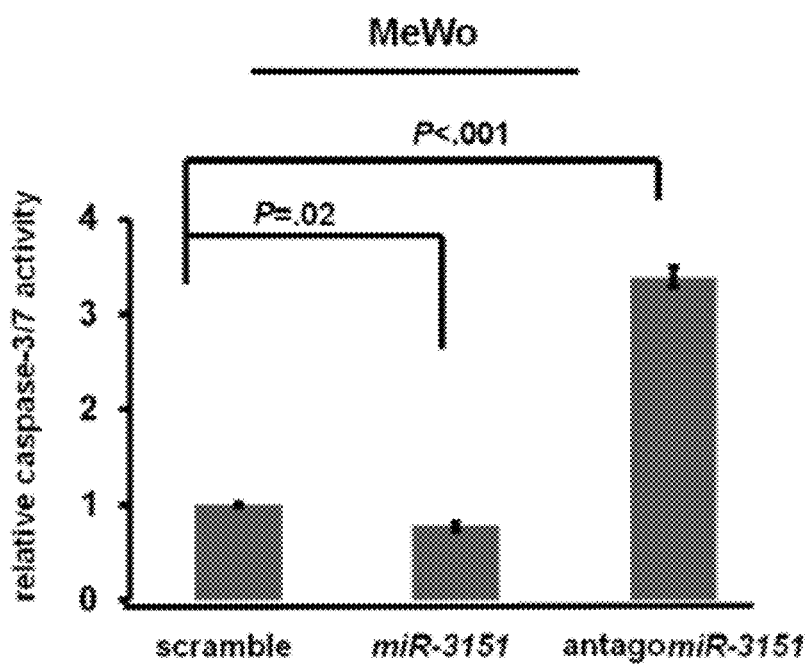

To test whether TP53 is also a direct miR-3151 target in the context of malignant melanoma, A375 cells (BRAF mut) and MeWo cells (BRAF wild type) were infected with miR-3151, antagomiR-3151, BAALC and scramble expression constructs. In both cell lines a decrease of TP53 expression levels was observed with the miR-3151 construct (A375 cells: 48% decrease, P=0.04, FIG. 16A; MeWo cells: 58% decrease, P=0.06, FIGS. 16A and B) compared to scramble control. This downregulation of TP53 by miR-3151 could also be validated on the protein level for both cell lines (FIGS. 16D and E). Next, tested was whether a decrease of miR-3151 expression levels would also result in increased apoptosis rates of melanoma cells as determined by chemiluminescent caspase-3 and caspase-7 assays. Following previous observation in AML cells, antagomiR-3151 treatment led to a significant increase of caspase activity (A375 cells: 1.8-fold increase, P<0.001, FIGS. 16E and F; MeWo cells: 3.4-fold increase, P<0.001; FIG. 16F), while forced miR-3151 expression further reduced the caspase activity of the melanoma cells (A375 cells: 41% reduction; P<0.001; MeWo cells: 12% reduction, P=0.02, FIGS. 16F and G). The results show that the repression of TP53 by miR-3151 occurs in melanoma and may apply to other human solid malignancies. The identification of this pathway provides a therapeutic target for melanoma.

Example 9 miR-3151 Harbors its Own Promoter and is Regulated by a SP1/NF-κB Transactivation Complex Association analyses revealed that despite a relatively strong correlation of miR-3151 and BAALC expression levels overall about one-third of the patients exhibited a discordant expresser status of the two genes. This led us to hypothesize that miR-3151 might harbor its own regulatory element which enables BAALC-independent expression of miR-3151.

Figure 17A:
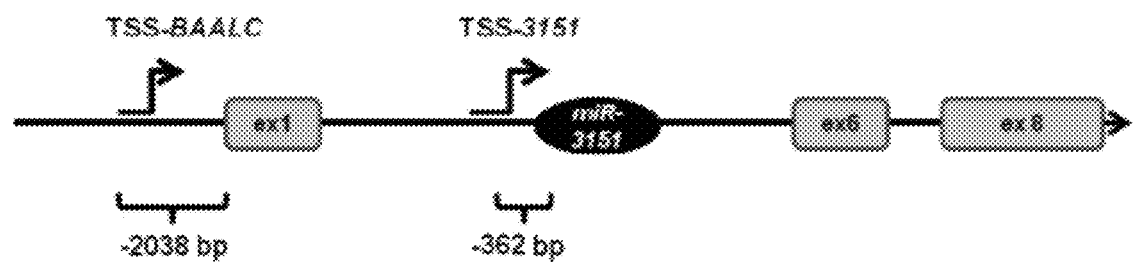
FIG. 17. Upstream regulation of miR-3151 and BAALC (FIG. 17A) Predicted transcription start sites for miR-3151 and BAALC, which are located 362 bp upstream of the stem-loop of miR-3151 (TSS-3151) and 2038 bp upstream of the ATG of BAALC (TSS-BAALC), respectively (illustration not drawn to scale). The transcription start sites were both predicted to be activated by the SP1/NF-κB complex.
(FIG. 17B) Luciferase assays of TSS-3151 with co-transfection of SP1, NF-κB and RUNX1. SP1 and NF-κB resulted in an increase of luciferase activity for TSS-3151 (SP1: 4-fold, NF-κB: 1.8-fold). To the contrary, RUNX1 did not change the luciferase activity of TSS-3151. The graphs are displayed as mean±standard deviation.
(FIG. 17C) Luciferase assays of TSS-BAALC with co-transfection of SP1, NF-κB and RUNX1. SP1 and NF-κB resulted in an increase of luciferase activity (SP1: 5-fold, NF-κB: 1.8-fold). TSS-BAALC can additionally be activated by RUNX1 (4.8-fold).
(FIG. 17D) Electrophoretic mobility shift assay (EMSA) of TSS-3151. Addition of nuclear extract from KG1a cells created the expected shift of SP1/NF-κB (well 2), which could be abrogated by addition of either SP1 (well 3) or NF-κB (well 4) antibody, or both (well 5).
(FIG. 17E)-(FIG. 17G) Effect of SP1 and NF-κB overexpression in MV4-11 cells on miR-3151 (FIG. 15E), BAALC (FIG. 15F) and TP53 expression levels (FIG. 15G).
(FIG. 17H) BAALC expression could additionally be regulated by overexpression of RUNX1.
(FIG. 17I) and (FIG. 17J) High miR-3151 and BAALC expressing KG1a cells were treated with the proteasome inhibitor bortezomib. This treatment led to a decrease in the expression levels of both genes (miR-3151 expression, FIG. 16A; BAALC expression, FIG. 16B). The graphs are displayed as mean±standard deviation.
(FIG. 17K) EMSA of TSS-3151. The shifting has been performed with nuclear extracts (NE) of DMSO (D) and bortezomib (B) treated KG1a cells. While the DMSO treated cells showed the known binding of SP1 to TSS-3151 (well 2), this binding was inhibited by treatment with bortezomib after 3 h (well 3). After 24 h of bortezomib treatment, the binding reoccurred (well 4). The SP1 shift in the DMSO treated cells could be abrogated by addition of SP1 antibody (well 5) or unlabeled competition (well 8).
(FIG. 17L) EMSA of TSS-BAALC. The experiment has been performed with nuclear extracts (NE) of DMSO (D) and either 50 μg/ml or 100 ug/ml bortezomib (B) treated KG1a cells. The extract usage is indicated on the bottom of the wells. While 100 μg/ml bortezomib (B) almost completely abrogated the binding, DMSO treated cells showed the known binding of SP1 to the predicted binding site to BAALC-TSS. Well 5 demonstrates the abrogation of the SP1 binding after addition of SP1 antibody.
Figure 17B:
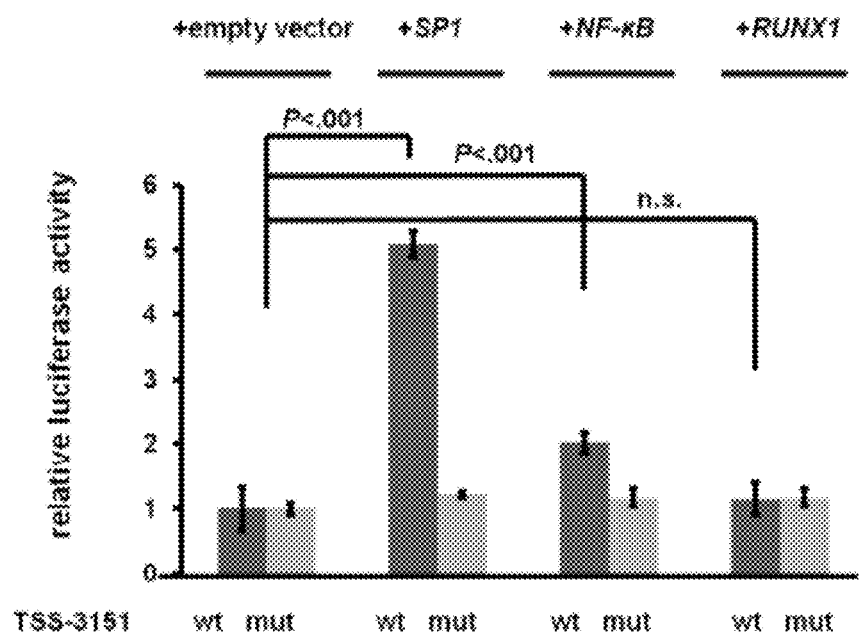
Figure 17C:
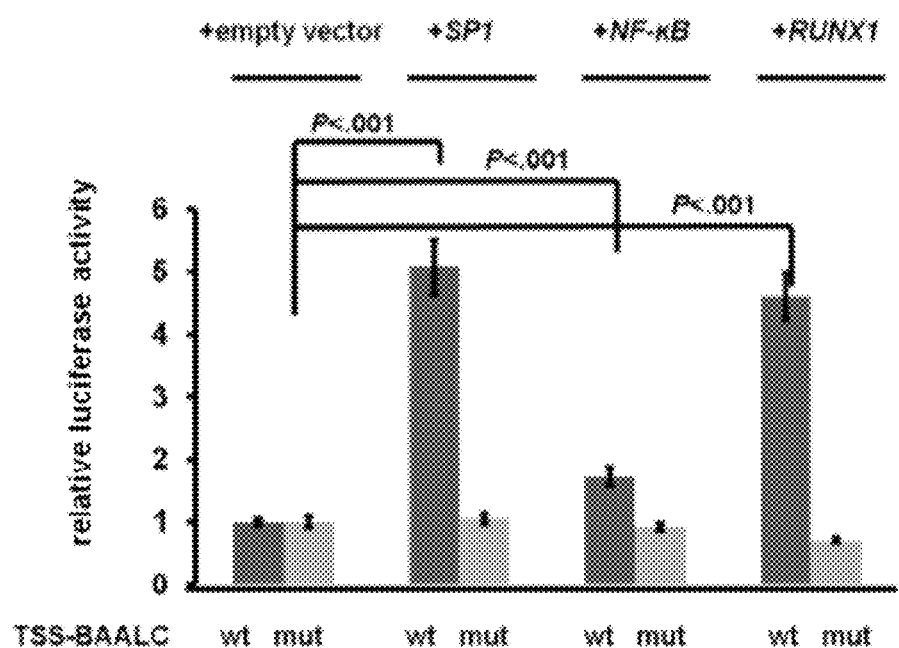

Using online available prediction tools a possible transcription start site (TSS-3151) was identified for miR-3151 located 362 bp upstream of the stemloop of miR-3151 and another transcription start site located 2038 bp upstream of the ATG of BAALC (TSS-BAALC, FIG. 17A). SP1 was predicted to be the transcription factor predominantly responsible for targeting both TSS-3151 and TSS-BAALC. The predicted TSS-BAALC was, in addition, predicted to harbor a binding site for the transcription factor RUNX1. Since SP1 has been shown to act as a transactivating complex together with NF-κB and both transcription start sites also showed a lower scoring NF-κB binding site, the inventors next co-transfected TSS-3151 with SP1- or NF-κB- and TSS-BAALC with SP1-, NF-κB- and RUNX1-expression constructs. Addition of the SP1-construct and to a lesser extent also of the NF-κB-construct resulted in an increase in luciferase activity for both transcription start sites, with TSS-BAALC in addition showing the predicted responsiveness to RUNX1 co-transfection (TSS-3151: SP1: 4.9-fold [±0.2], NF-κB: 2-fold [±0.15], RUNX1: 1.2-fold [±0.25]; TSS-BAALC: SP1: 5-fold [±0.44], NF-κB: 1.8-fold [±0.13], RUNX1: 4.7-fold [±0.37]; FIGS. 17B and C).

Figure 17D:
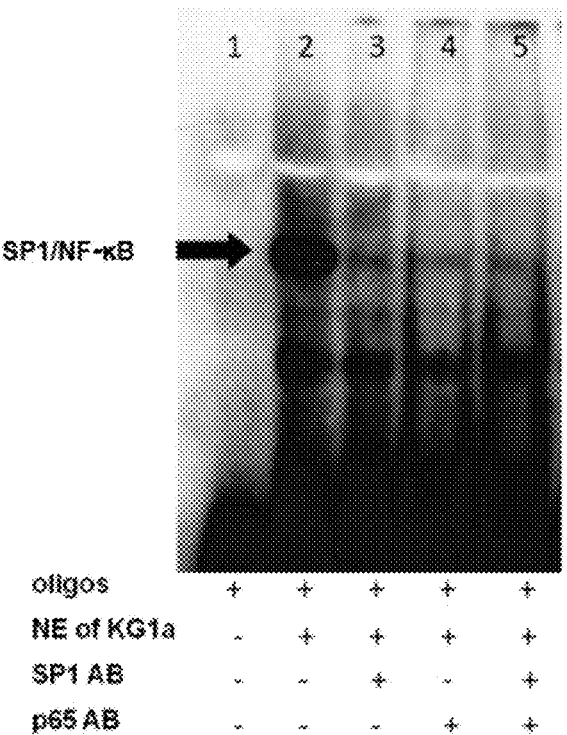

Utilizing Electrophoretic Mobility Shift Assays (EMSA), the SP1 and NF-κB binding to TSS-3151 was confirmed. Addition of SP1 and NF-κB antibodies led to an abrogation of the binding (FIG. 17D).

Example 10

Figure 17E:
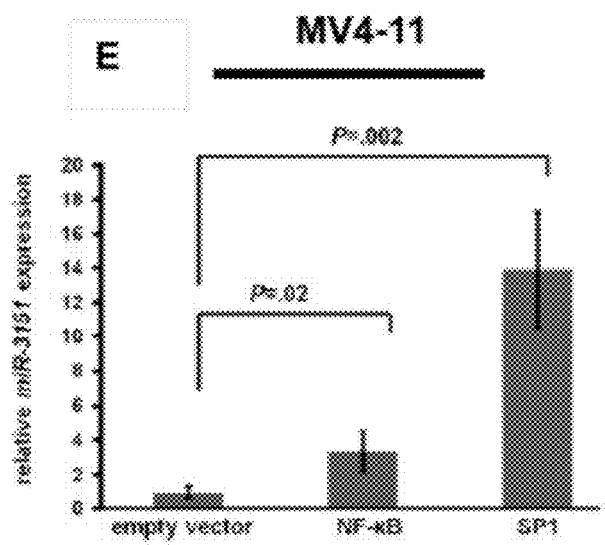
Figure 17F:
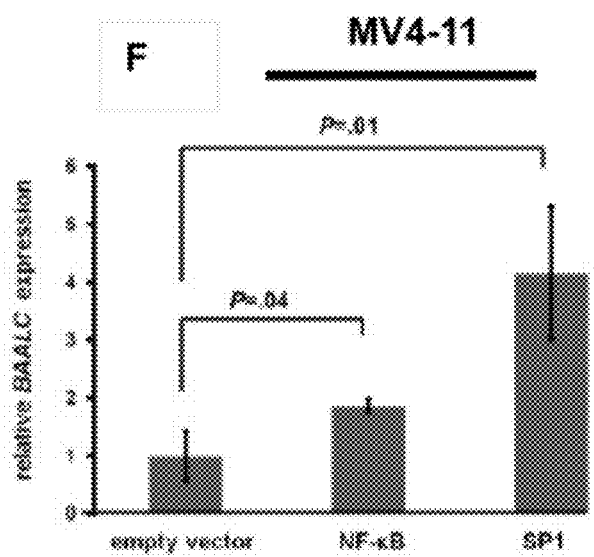
Figure 17G:
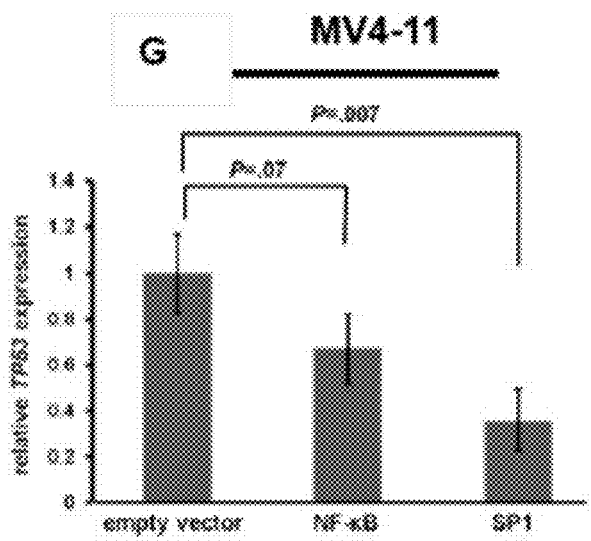
Figure 17H:
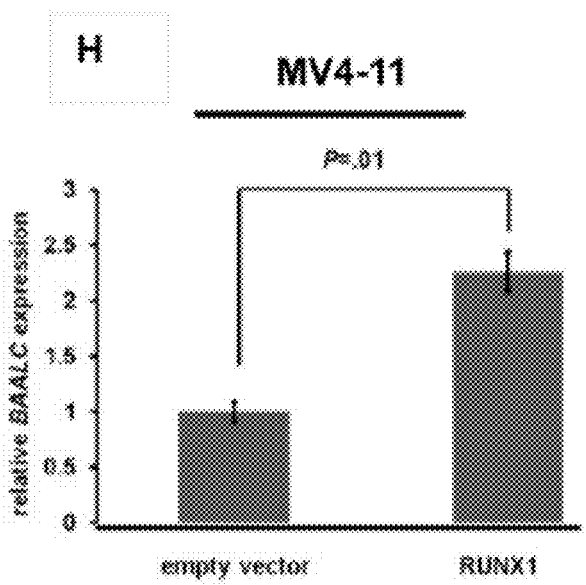

SP1 and NF-κB Overexpression Increase miR-3151 and BAALC Expression Levels and RUNX1 Additionally Increases BAALC Expression Next, the inventors transfected MV4-11 cells with SP1 and NF-κB expression constructs. Forced expression of SP1 led to a 13.7-fold increase of miR-3151 (P=0.002) and a 3.8-fold increase of BAALC expression levels (P=0.01), while forced expression of NF-κB led to a 2.5-fold increase of miR-3151 (P=0.02) and a 1.8-fold increase of BAALC expression levels (P=0.04, FIGS. 17E and F). Consequently, SP1 and NF-κB overexpression also led to a decrease of TP53 expression levels (SP1: P=0.007, NF-κB: P=0.07; FIG. 17G). Forced expression of RUNX1 led to a 2.2-fold increase of BAALC, but not of miR-3151 expression (FIG. 17H). Taken together, the results confirm the SP1/NF-κB transactivating complex as an important regulator of miR-3151 and BAALC expression levels and RUNX1 as an additional "fine-tuner" of BAALC expression regulation.

Example 11 miR-3151 and BAALC Overexpression are Targetable with Bortezomib

Figure 17I:
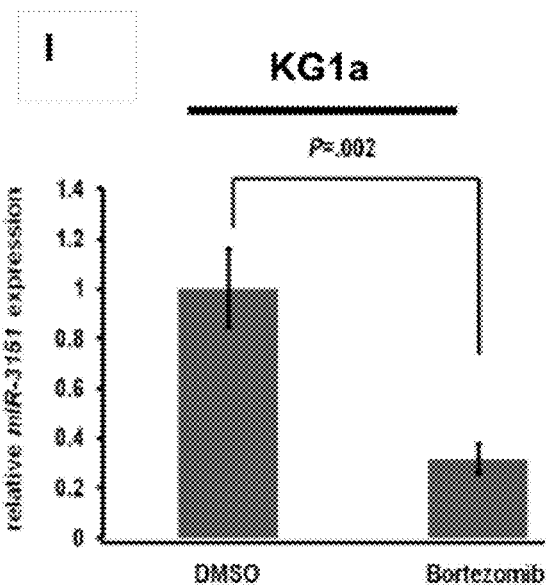
Figure 17J:
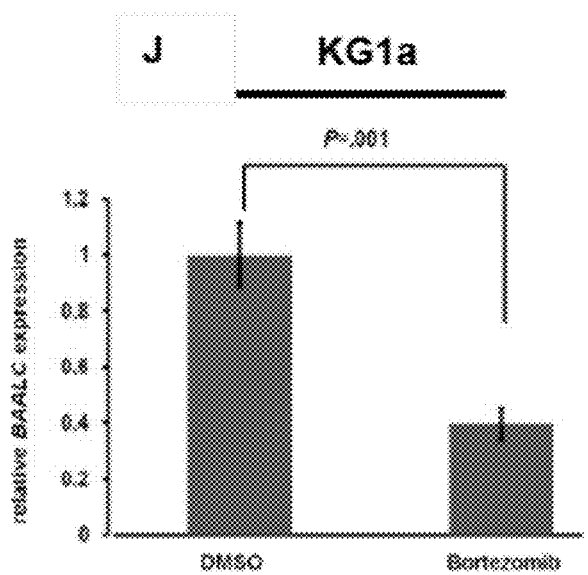
Figure 17K:
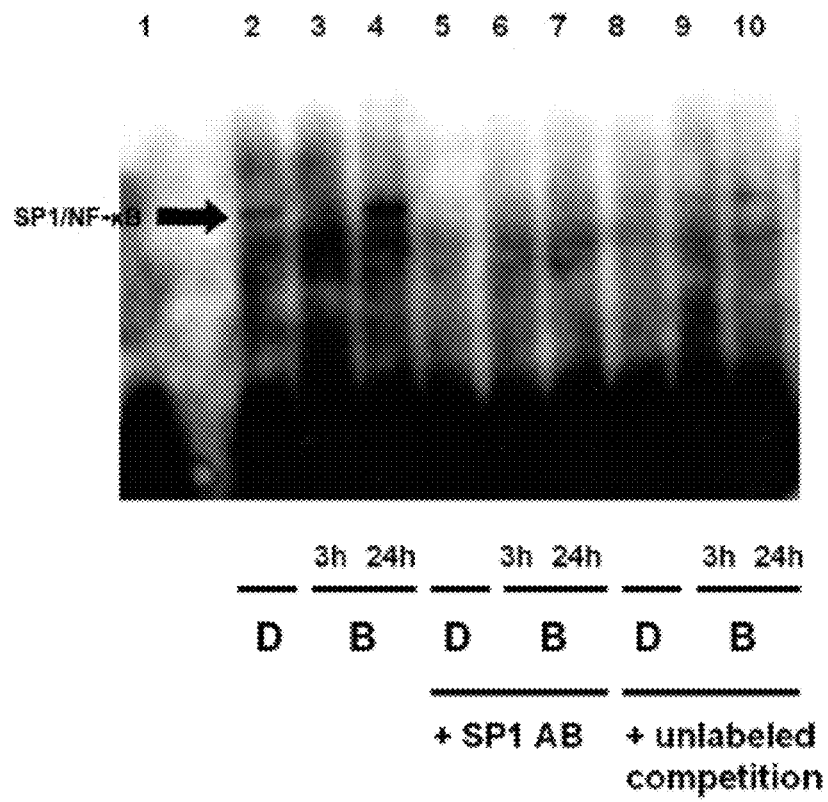
Figure 17L:
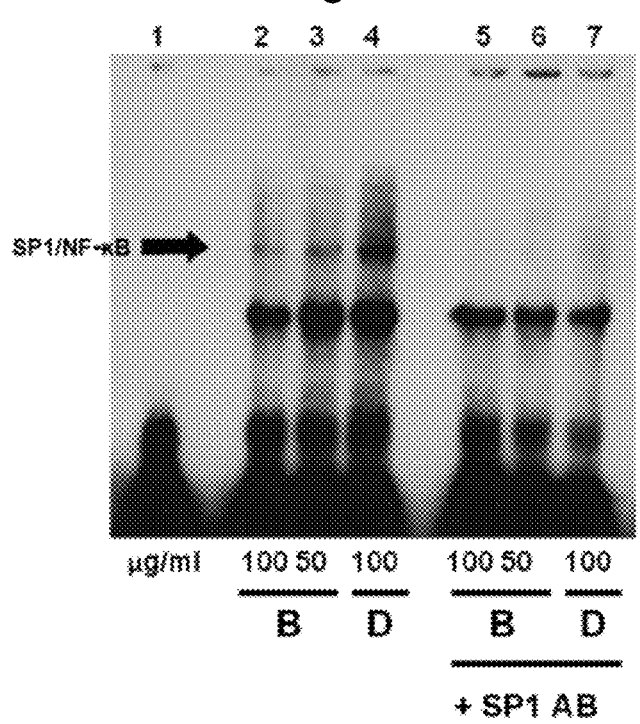
Figure 18:
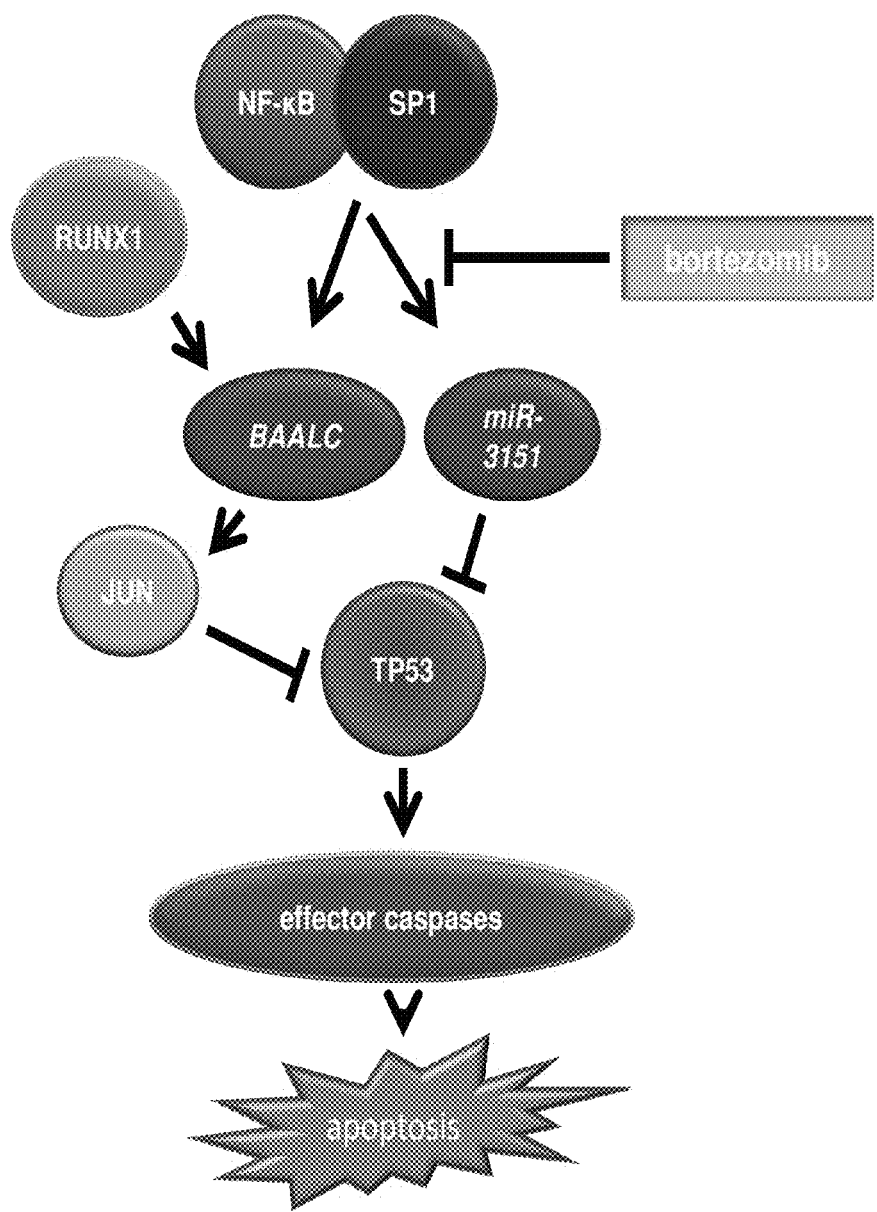
FIG. 18 A graphical representation of interactions—Intronic miR-3151 directly targets TP53 and deregulates the TP53 apoptosis pathway. The miR-3151 host gene BAALC increases JUN expression, thereby directly and indirectly leading to deregulation of TP53. Both miR-3151 and BAALC are independently regulated by a SP1/NF-κB transactivating complex. Upregulated miR-3151 and BAALC expression levels may be lowered by treatment with the proteasome inhibitor bortezomib.

Evidence shows that the proteasome inhibitor bortezomib abrogates SP1/NF-κB binding to their targeted sequences. Consequently it was tested whether the same mechanism might be applicable to miR-3151 and BAALC expression and therefore have the potential of reducing increased expression levels of both genes in AML patients. High miR-3151 expressing KG1a cells were treated with either 100 μg/ml bortezomib or vehicle (DMSO), and miR-3151, BAALC, TP53 and JUN expression levels were measured by RT-PCR 3 h after treatment. A decrease of miR-3151 and BAALC expression levels and an increase of TP53 expression levels could be observed compared to vehicle treated control (KG1a cells: miR-3151 expression: −70%, P=0.002; BAALC expression: −62%, P=0.002; FIGS. 17I and J). To show whether the decrease of the expression levels was caused by the disruption of SP1/NF-κB binding to the gene promoters, an additional EMSA of TSS-3151 and TSS-BAALC was performed, this time using nuclear extract harvested after bortezomib (100 μg/ml vs. vehicle) treatment. Bortezomib treatment inhibited the binding of SP1/NF-κB to the respective transcription start sites (FIGS. 17K and L). This observation further supports the hypothesis that both miR-3151 and BAALC are targeted by the SP1/NF-κB complex and that this activation can be inhibited by treatment with bortezomib.

Example 12 miR-3151 is Deregulated in Papillary Thyroid Carcinoma

Figure 30:
FIG. 30. miR-3151 expression in 10 paired papillary thyroid carcinoma (PTC) samples, the graph shows relative miR-3151 expression: T=tumor sample, N=non-tumor sample. PTC tumor has on average 85% less miR-3151 expression when compared to paired normal tissue.

Papillary thyroid carcinoma (PTC) is the most common type of thyroid cancer, representing 75% to 85% of all thyroid cancer cases. Approximately a third to a half of papillary thyroid carcinomas harbor point mutations in the BRAF oncogene, activating the MAPK/ERK pathway. miR-3151 is deregulated in papillary thyroid carcinoma. As shown in FIG. 30, it is downregulated in cancerous samples. PTC tumor has on average 85% less miR-3151 expression when compared to paired normal tissue.

DISCUSSION

Much remains to be learned about the interaction of intronic miRs and their host genes. Even though it is believed that in many cases both the miR and host gene may impact on the same or similar pathways, thereby directly and/or indirectly supporting each other's functions, most genes harboring miR genes in their introns are still studied without considering their intronic counterparts.

In the case of BAALC, the discovery and subsequent assessment of an intronic miR which independently impacts on the clinical outcome of AML patients led to the characterization of two pathways that converge in their downstream effects.

Analysis was performed on the GEP of 179 CN-AML patients identified the TP53 pathway as the major affected one, with TP53 itself being an in-silico predicted target of miR-3151. TP53 was validated as a direct target gene of miR-3151. Evidence shows that the basis of the leukemogenic effect of high miR-3151 expression levels relates to its impairment of TP53 expression. Furthermore, it is shown that BAALC causes the upregulation of the JUN proto-oncogene, which in turn further represses TP53 expression.

Even though mutations of the TP53 gene are a common event in many human malignancies, they only occur in approximately 10% of all AML cases. Recently, the impairment of TP53 received special attention in AML patients with a complex karyotype. Besides impairment caused by TP53 mutations, quantitative differences in the expression of TP53 are known to affect resistance to chemotherapeutic treatment while low expression of TP53 may support leukemia cell growth in vitro and in vivo. Recently, it was shown that TP53 is targeted by the tumor suppressor miRs miR-15 and miR-16 in chronic lymphocytic leukemia (CLL) in a feedback circuit, promoting apoptosis and ultimately leading to a less aggressive phenotype of CLL patients. As described herein, there is a leukemogenic cycle involving the oncogenes miR-3151 and BAALC, as well as the transcription factors SP1, NF-κB and RUNX1.

The leukemogenic effects of BAALC may rely on impaired TP53 function. An increase in the growth of leukemia cells infected with BAALC after siRNA mediated knockdown of TP53 was shown. This growth advantage was also increased compared to the one observed after sole knockdown of TP53. The strongest effect on growth and viability was seen in cells with forced expression of both miR-3151 and BAALC. Without wishing to be bound by theory, the combined effect of both genes may be in part caused by the miR-3151-mediated impairment of TP53, which in turn induces BAALC to acquire an enhanced oncogenic function-an in-vitro observation that supports the effects seen in vivo in leukemia patients.

Taken together, the impairment of TP53 by miR-3151 may be not only a crucial downstream effector of miR-3151 but constitutively enable the miR-3151 host gene BAALC to promote leukemogenesis. Of note, while miR-3151 overexpression was on its own able to increase leukemogenesis in our MV4-11 NSG mouse model, overexpression of BAALC alone did not shorten the survival compared to scramble control.

Of special interest was the analysis of the upstream regulatory machinery of the miR-3151/BAALC locus. The TSS of miR-3151 and BAALC was characterized, which can regulate the expression of the two genes independently. Both are regulated by a SP1/NF-κB transactivating complex and this activation can be abrogated by treatment with the proteasome inhibitor bortezomib.

The SP1/NF-κB transactivating complex causes high expression of the tyrosine kinases KIT and FLT3 in AML, which when aberrantly activated are both associated with poor prognosis of AML patients. The fact that both the intronic miR-3151 and its host gene BAALC are regulated by this complex, highlights the importance of the SP1/NF-κB cascade as a therapeutic target. The results support the application of the proteasome inhibitor bortezomib as a treatment option for some high-risk AML patients.

The use of bortezomib also represents a potential treatment option for high miR-3151/BAALC expressing malignant melanoma patients.

BAALC expression is additionally regulated by the transcription factor RUNX1. This may explain the partly discordant expresser status of the two genes, since RUNX1 has no effect on miR-3151 expression levels. The significance of RUNX1 as a strong regulator of BAALC expression levels is in line with the recent finding that BAALC expression is associated with the presence of rs62527607 [T], a heritable polymorphism in the BAALC promoter region, which creates a binding site for RUNX1. In contrast to its host, miR-3151 expression levels are not associated with the presence of the risk-allele of rs62527607[T].

Experimental Procedures

Tissue Culture Experiments

KG1, KG1a and MV4-11 cells were obtained from the American Type Culture Collection (ATCC). Cells were cultured in RPMI medium supplemented with 20% Fetal Bovine Serum (FBS) and 1% Antibiotic-Antimycotic (Gibco). KG1 and MV4-11 cells were chosen for miR-3151 and BAALC overexpression experiments because of their low endogenous miR-3151 and BAALC expression levels. KG1a cells were chosen for miR-3151 knock-down, transcription factor siRNA and bortezomib treatment experiments because of their high endogenous miR-3151 and BAALC expression levels. The endogenous miR-3151 and BAALC expression levels of the cell lines are displayed in FIG. 24. Primary AML blasts from leukapheresis samples collected from 4 patients with de novo disease were obtained from the Ohio State University (OSU) Leukemia Tissue Bank. All patients provided written informed consent according to the Declaration of Helsinki to store and use of their tissue for discovery studies according to the OSU institutional guidelines under protocols approved by the OSU Institutional Review Board. Cells were cultured in StemSpan media (Stemcell Technologies) without additional supplements.

Validation of Genes Affected by miR-3151 and BAALC Expression

For stable expression of miR-3151, the miR-3151 stem-loop and the open-reading frame of BAALCs main transcript variant (containing exons 1, 6 and 8) were cloned into two lentiviral expression vectors as described, using lentiviral miR-scramble (for miR-3151) and empty vector (for BAALC) as the respective controls. To analyze the effects of forced miR-3151 and BAALC expression on the predicted target genes, the mRNA expression levels were assessed and compared to the effects of cells infected with scramble control using Real-Time PCR. Western blotting to test the effects of miR-3151 and BAALC on protein levels was performed as described. The 3'-UTR binding site of TP53 was cloned into a luciferase reporter vector (wild-type vs. mutated miR-3151 binding sequence) and luciferase activity was assessed. To show the physical interaction to the target gene in a luciferase assay, an antagomiR was used that contained the complementary sequence to miR-3151.

Leukemogenesis in NOD/SCID Gamma Knock-Out Mice 10-week-old male NOD/SCID mice (The Jackson Laboratory) were i.v. injected through a tail vein with 1.5×10⁵ murine adapted MV4-11 cells. Engraftment was validated by flow cytometric measurement of CD45 at d+37. Organ samples were harvested from all mice and processed for RNA and cDNA. Real-Time PCR was performed on all samples as described above. These studies were performed in accordance with OSU institutional guidelines for animal care and under protocols approved by the OSU Institutional Animal Care and Use Committee.

MIR3151 and BAALC Promoter Analysis

Luciferase reporter constructs containing the predicted transcription start sites (or their mutated counterparts) for miR-3151 and BAALC were cloned into the multiple cloning site of a promoterless luciferase reporter vector (pGL4.11, Promega). Luciferase assays were performed in triplicate, co-transfecting the luciferase reporter constructs with the overexpression constructs of the predicted activating transcription factors SP1, NF-κB or RUNX1 according to the recommendations detailed in the Dual-Luciferase Reporter Assay System (Promega). For further analysis, relative expression was normalized using co-transfected Renilla luciferase. All primer sequences are listed in FIG. 28.

Caspase Assays

Apoptosis changes in primary AML patient blasts infected with lentiviral miR-3151, antagomiR-3151, BAALC and scramble were analyzed using the chemiluminescent Capase-3/7 assay (Promega) 72 h after infection, using 20,000 cells in duplicate, according to the manufacturer's instructions. MV4-11, KG1 and KG1a cell lines were analyzed in duplicate 72 h after Puromycin selection.

Electrophoretic Mobility Shift Assay (EMSA)

Nuclear proteins were extracted from KG1a cells 3 h after treatment with 100 µg/ml bortezomib (sc-217785, Santa Cruz Biotechnology), or vehicle (100 µg/ml DMSO) using the Nuclear Extract Kit (Active Motif) according to the manufacturer's instructions.

For EMSA performance, the Thermo Scientific LightShift Chemiluminescent EMSA Kit (Pierce/Thermo Fisher Scientific) was used according to the manufacturer's instructions. Oligonucleotide sequences are provided in FIG. 29.

Statistical Methods

Data were represented as mean±standard deviation (s.d.) of at least three independent experiments unless otherwise indicated and analyzed by the two-tailed Student's t-test. The means and s.d. were calculated and displayed in bar graphs as the height and the corresponding error bar, respectively. Mouse survival was calculated using the Kaplan-Meier method, and survival curves were compared by the log-rank test. A P<0.05 was considered statistically significant.

Stable Expression of miR-3151 and BAALC

The stemloop of miR-3151 with 200 bp flanking sequence and the open-reading frame of BAALC's main transcript variant (containing exons 1, 6 and 8) were cloned into HIV based lentiviral dual promoter vectors (pCDH-CMV-MCS-EF1-copGFP+Puro cDNA and pCDH-CMV-MCS-EF1-Puro; both System Biosciences). The specific insert having the sequence: GGATCCGGGTGGGGTAATGGGATAA-GATCTTCCTGTCAGACCTGATCCCATTGCCCCAC CTTTTTGAATTC (SEQ ID NO. 35). It contains a hairlooppin structure including miR-3151 sense (tggactaggg-taacggggtgg) (SEQ ID NO. 36) and antisense (acctgatcccat-tgccccac) (SEQ ID NO. 37) nucleotides with provoked mismatches to the actual sequence.

As a control, lentiviral scramble control miR was used according to the manufacturer's instructions (miRZiP000, System Biosciences). 4500 µg lentiviral construct was transfected into 293TN cells using 45 µg pPACKH1 and 55 µl PureFection (System Biosciences). After 48 h and 72 h, the supernatant containing the pseudoviral particles was collected and the virus was precipitated overnight at 4° C. using 5 ml PEG-IT virus precipitation solution (System Biosciences). 200 µl Phosphate Buffered Saline and 25 µM Hepes Buffer were used for resuspension of the pelleted virus. 200,000 cells/ml were infected in triplicate with 20 IU virus, using 5 µl Transdux Infection Reagent (System Biosciences). Ten days later successfully infected cells were selected using Puromycin. To check for successful overexpression of miR-3151 and BAALC and to analyze the effect of forced miR-3151 expression on the predicted target genes, RNA (1 million cells) was harvested on day 14 and reverse transcribed to cDNA using the TaqMan MicroRNA Reverse Transcription Kit (Life Technologies Corporation/Applied Biosystems) or the Superscript III First-Strand cDNA Synthesis Kit (Life Technologies Corporation/Invitrogen). Both kits were used according to the manufacturer's instructions.

Simultaneously, protein (from 4 million cells) was harvested and used for Western blotting.

For simultaneous overexpression of both miR-3151 and BAALC, Puromycin-selected miR-3151 overexpressing cells were infected with GFP-labeled BAALC-expressing pseudoviral particles (pCDH-CMV-MCS-EF1-copGFP+Puro). GFP-positive cells were then selected using the ARI-AIII cell sorter.

For infection of primary patient blasts 600,000 cells/ml were infected in triplicate with 20 IU virus, using 5 µl Transdux Infection Reagent (System Biosciences). Due to the high infection efficiency of >80%, RNA was harvested after 48 and 72 h without further selection procedures.

Luciferase Reporter Assays

To assess the inhibiting potential of miR-3151 on TP53 expression, 250 bp of the respective 3'-UTR containing the predicted miR-3151 binding sites were cloned 3' of the luciferase gene into a luciferase reporter vector (pGL4.24; Promega) using the EcoRI-restriction site. Mutation of the predicted binding site was accomplished using bi-directional mutation primers, exchanging 3 nucleotides of the respective predicted miR-3151 binding sequences. Primer sequences and the corresponding annealing temperatures are listed in FIG. 27. HEK 293T cells obtained from ATCC were cultured in DMEM culture medium supplemented with 10% FBS, L-glutamine (200 mM), and antibiotic/antimycotic agent (all Life Technologies Corporation/Gibco) and grown at 37° C. with 5% $CO_2$. When the culture reached 80% confluency, the cells were transfected in triplicate with 250 ng reporter construct and 100 ng control construct (Renilla, pGL4.74; Promega) using Lipofectamin 2000 transfection reagent (Life Technologies Corporation/Invitrogen). Cells were co-transfected with 10 pmol of either MIR-3151 (Pre-miR miRNA Precursor, Life Technologies Corporation/Ambion) or scramble control-miR (negative Control Pre-miR #1, Life Technologies Corporation/Ambion). Transfected cells were incubated for 12 h at 37° C. with 5% $CO_2$ in Opti-MEM II medium containing the Lipofectamine/plasmid combination. Protein lysates were assessed for firefly luciferase and Renilla luciferase activities according to the recommendations detailed in the Dual-Luciferase Reporter Assay System (Promega). For further analysis, relative expression was normalized using co-transfected Renilla luciferase.

MiR-3151 and BAALC Promoter Analysis

Luciferase reporter constructs (~50 bp genomic sequence) containing the predicted transcription start sites for miR-3151 and BAALC were cloned into the multiple cloning site of the promoterless luciferase reporter vector (pGL4.11, Promega) using the KpnI and SacI restriction sites. Next, the predicted binding sequences of the respective transcription factors were mutated using bi-directional mutation primers (all primer sequences used for cloning and mutation introduction are listed in FIG. 26). Expression constructs for the potential activating transcription factors SP1, NF-κB and RUNX1 were constructed by cloning the respective open reading frame (ORF) into the CMV-driven expression vector pIRES2-EGFP (Clontech). The primer sequences for the cDNA-based cloning PCR are listed in FIG. 26. HEK293 cells were then transfected in triplicate with 250 ng luciferase reporter construct and 100 ng control construct (pGL4.74, Promega) and co-transfected with 50 ng of the different expression constructs or empty pIRES2-EGFP vector control. Transfected cells were incubated for 24 h at 37° C. with 5% $CO_2$ in Opti-MEM II medium containing the Lipofectamine/plasmid combination. Protein lysates were assessed for firefly luciferase and Renilla luciferase activities according to the recommendations detailed in the Dual-Luciferase Reporter Assay System (Promega). For further analysis, relative expression was normalized using co-transfected Renilla luciferase.

TP53 Overexpression and Knock-Down for Cell Growth Analysis

The open reading frame of TP53 was cloned into the CMV-driven expression vector pIRES2-EGFP (Clontech). The primer sequences for the cDNA-based cloning PCR are listed in FIG. 26. KG1 and MV4-11 cells stably overexpressing miR-3151, BAALC, miR-3151/BAALC and scramble control were transfected with either 1 µg TP53 expression construct or empty vector control using Purefection transfection reagent according to the manufacturer's instructions (System Biosciences). KG1a cells stably expressing antagomiR-3151 and scramble control were transfected with a siRNA pool against TP53 (sc-29435) or siRNA-scramble control (sc-37007) using Purefection transfection reagent. After 12 h, 100,000 cells were seeded in duplicate for growth curve measurements.

Cells were counted for 5 consecutive days using bromphenol-blue staining for detection with a hemocytometer.

Transient Overexpression of SP1, NF-κB and RUNX1

For transient overexpression, 3 µg of the aforementioned overexpression constructs of SP1, NF-κB, and RUNX1 (all cloned in pIRES2-EGFP vector, Clontech) were transfected in duplicate into 3 million MV4-11 and KG1 cells using electroporation (Amaxa) according to the manufacturer's instructions.

For knock-down of SP1 and NF-κB, siRNA pools against both genes and siRNA scramble control were obtained from Thermo Scientific and transfected in duplicate into high miR-3151 and BAALC expressing KG1a cells using Purefection reagent (System Biosciences), following the manufacturer's instructions.

In summary, the complex interplay of an oncomiR and its oncogenic host gene is shown leading to deregulation of one of the most important cancer pathways. The interaction is not only present in the downstream effects but also in the upstream regulation. These mechanisms are of special importance in the context of treatment options when targeting genes that harbor intronic miRs. For example, in some instances, even if a treatment is known to inhibit the expression levels of the host gene, additional targeted treatment would be necessary to inhibit the activity of the intronic miR. This type of interaction is among the numerous examples of miR-host gene combinations in the human genome.

The invention illustratively described herein suitably can be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification, thus indicating additional examples, having different scope, of various alternative embodiments of the invention. Also, the terms "comprising", "including", containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed.

Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention All publications, including patents and non-patent literature, referred to in this specification are expressly incorporated by reference herein. Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A method of treating a subject having or suspected of having a cancer having an increased expression of miR-3151, the method comprising:
   administering to the subject an effective amount of a miR-3151 inhibitor sufficient to modulate expression of miR-3151, wherein the levels of miR-3151 are decreased after administration, thereby treating the subject;
   wherein the cancer is cytogenetically normal acute myeloid leukemia (CN-AML).

2. A method of treating a patient having acute myelogenous leukemia (AML) or acute lymphoblastic leukemia (ALL) comprising:
   measuring the expression of at least one biomarker in a biological sample from a patient, wherein the at least one biomarker is selected from the group consisting of: gene products of BAALC and miR-3151;
   comparing the expression of the at least one biomarker to a corresponding control;
   determining whether the expression of either BAALC or miR-3151 is high;
   administering antagomiR-3151 if the expression of either BAALC or miR-3151 is high, in an amount sufficient to modulate expression of one or more of BAALC and miR-3151; wherein the levels of one or more of BAALC and miR-3151 are decreased after administration, thereby treating the subject.

3. The method of claim 2 further comprising: monitoring the expression of the at least one biomarker subsequent to the step of administering the antagomiR-3151.

4. A method of inhibiting miR-3151 expression in a subject undergoing treatment for acute myeloid leukemia (AML) comprising:
   administering to a subject undergoing treatment for ALL, in which at least miR-3151 gene product is upregulated in cancer cells of the subject, an effective amount of at least one compound for inhibiting expression of the at least one miR-3151 gene product in an amount sufficient to modulate expression of miR-3151; wherein the levels of miR-3151 are decreased after administration, thereby inhibiting miR-3151 expression in the subject.

5. A method of inhibiting a leukemia in a subject who has acute myeloid leukemia (AML), comprising:
   determining the amount of at least one miR-3151 gene product in cancer cells from a subject;
   altering the amount of miR-3151 gene product expressed in the cancer cells by administering to the subject an effective amount of at least one compound for inhibiting expression of the at least one miR-3151 gene product, if the amount of the miR-3151 gene product expressed in the cancer cells is greater than the amount of the miR-3151 gene product expressed in control cells; and
   inhibiting AML in the subject.

6. The method of claim 5 wherein the compound comprises antagomiR-3151.

\* \* \* \* \*